(12) United States Patent
Spits et al.

(10) Patent No.: US 11,136,407 B2
(45) Date of Patent: Oct. 5, 2021

(54) THERAPEUTIC ANTI-CD9 ANTIBODY

(71) Applicant: AIMM Therapeutics B.V., Amsterdam Zuidoost (NL)

(72) Inventors: Hergen Spits, Amsterdam Zuidoost (NL); Paula Maria Wilhelmina Van Helden, Amsterdam Zuidoost (NL); Remko Schotte, Amsterdam Zuidoost (NL); Wouter Pos, Amsterdam Zuidoost (NL); Christien Fatmawati, Amsterdam Zuidoost (NL); Daniël Michiel Go, Amsterdam Zuidoost (NL); Koen Wagner, Amsterdam Zuidoost (NL); Julien Christian Villaudy, Amsterdam Zuidoost (NL)

(73) Assignee: AIMM Therapeutics B.V., Amsterdam Zuidoost (NL)

( * ) Notice: Subject to any disclaimer, the term of this patent is extended or adjusted under 35 U.S.C. 154(b) by 0 days.

(21) Appl. No.: 16/068,742

(22) PCT Filed: Jan. 6, 2017

(86) PCT No.: PCT/NL2017/050003
§ 371 (c)(1),
(2) Date: Jul. 9, 2018

(87) PCT Pub. No.: WO2017/119811
PCT Pub. Date: Jul. 13, 2017

(65) Prior Publication Data
US 2019/0023803 A1 Jan. 24, 2019

(30) Foreign Application Priority Data
Jan. 8, 2016 (EP) .................................. 16150698

(51) Int. Cl.
*C07K 16/28* (2006.01)
*G01N 33/574* (2006.01)
*A61P 35/00* (2006.01)
*C07K 14/705* (2006.01)
*A61K 39/00* (2006.01)

(52) U.S. Cl.
CPC .......... *C07K 16/2896* (2013.01); *A61P 35/00* (2018.01); *C07K 14/70596* (2013.01); *C07K 16/2818* (2013.01); *G01N 33/57492* (2013.01); *A61K 2039/505* (2013.01); *A61K 2039/507* (2013.01); *C07K 2317/21* (2013.01); *C07K 2317/34* (2013.01); *C07K 2317/54* (2013.01); *C07K 2317/73* (2013.01); *C07K 2317/732* (2013.01); *C07K 2317/734* (2013.01); *G01N 2333/70596* (2013.01)

(58) Field of Classification Search
CPC combination set(s) only.
See application file for complete search history.

(56) References Cited

U.S. PATENT DOCUMENTS

| 7,473,531 B1 * | 1/2009 | Domon ............ G01N 33/57438 435/7.1 |
| 8,969,526 B2 | 3/2015 | Baehner et al. |
| 9,127,251 B2 | 9/2015 | Spits et al. |
| 2009/0068182 A1 | 3/2009 | Young et al. |
| 2010/0158801 A1 | 6/2010 | Young et al. |
| 2015/0010913 A1 | 1/2015 | Ohta et al. |
| 2016/0025739 A1 * | 1/2016 | Lim ................... G01N 33/6893 424/697 |

FOREIGN PATENT DOCUMENTS

| EP | 0508417 B1 | 7/1999 |
| EP | 1974017 B1 | 11/2013 |
| EP | 2803673 A1 | 11/2014 |
| JP | H05276981 A | 10/1993 |
| WO | 19950033823 | 12/1995 |
| WO | 20040007685 A2 | 1/2004 |
| WO | 20040077062 A2 | 9/2004 |
| WO | 2008/084410 A2 | 7/2008 |
| WO | 20090023955 A1 | 2/2009 |
| WO | 20090120039 A2 | 10/2009 |
| WO | 2009/157623 A1 | 12/2009 |
| WO | 2010/054007 A1 | 5/2010 |
| WO | 20100087994 A2 | 8/2010 |
| WO | 20130099925 A1 | 7/2013 |
| WO | 20140145940 A1 | 9/2014 |

OTHER PUBLICATIONS

Kabat, Elvin A., et al., "Sequences of Proteins of Immunological Interest" National Institutes of Health (U.S.), vols. 1-3, 5th ed., NLM ID:9210532; NIH Publication No. 91-3242 (1991).
Bartolomé, et al., "The Chemokine Receptor CXCR4 and the Metalloproteinase MT1-MMP are Mutually Required during Melanoma Metastasis to Lungs.", The American Journal of Pathology, vol. 174, No. 2, pp. 602-612, Feb. 2009.
Chen, Y., et al., "Selection and Analysis of an Optimized Anti-VEGF Antibody: Crystal Structure of an Affinity-matured Fab in Complex with Antigen", (1999) J. Mol Biol 293:865-881.
Garcia-Espana, et al., "Appearance of new tetraspanin genes during vertebrate evolution.", Genomics 91 (2008) 326-334.
Yang, et al., "Contrasting Effects of EWI Proteins, Integrins, and Protein Palmitoylation on Cell Surface CD9 Organization.", The Journal of Biological Chemistry, vol. 281, No. 18, pp. 12976-12985, May 5, 2006.
de Jong, et al., "A Novel Platform for the Potentiation of Therapeutic Antibodies Based on Antigen-Dependent Formation of IgG Hexamers at the Cell Surface.", PLoS Biol. Jan. 6, 2016;14(1).

(Continued)

*Primary Examiner* — Laura B Goddard
(74) *Attorney, Agent, or Firm* — Verrill Dana, LLP

(57) ABSTRACT

The present invention provides novel binding compounds and therapeutic applications thereof.

31 Claims, 35 Drawing Sheets
Specification includes a Sequence Listing.

(56) References Cited

OTHER PUBLICATIONS

Gouy, et al., "SeaView version 4: A multiplatform graphical user interface for sequence alignment and phylogenetic tree building." Mol Biol Evol. Feb. 2010;27(2):221-224.

Hanly, et al., "Review of polyclonal antibody production procedures in mammals and poultry.", ILAR Journal (1995); vol. 37, No. 3: 93-118.

Hattori, et al., "Downregulation of rheumatoid arthritis-related antigen RA-A47 (HSP47/colligin-2) in chondrocytic cell lines induces apoptosis and cell-surface expression of RA-A47 in association with CD9.", J.Cell Physiol. (2005); 202(1): 191-204.

Huang, et al., "Correlation of reduction in MRP-1/CD9 and KAI1/CD82 expression with recurrences in breast cancer patients.", Am J Pathol. Sep. 1998;153(3):973-983.

Iwai, et al., "Abundant expression of tetraspanin CD9 in activated osteoclasts in ovariectomy-induced osteoporosis and in bone erosions of collagen-induced arthritis.", Rheumatol.Int. (2008); 28(3): 225-231.

Jin, et al., "Statins decrease lung inflammation in mice by upregulating tetraspanin CD9 in macrophages.", PLoS One (2013); Sep 9; 8(9): e73706.

Schlothauer, et al., "Novel human IgG1 and IgG4 Fc-engineered antibodies with completely abolished immune effector functions.", PEDS Advance Access published Aug. 29, 2016, 1-10.

Kawakatsu, et al., "Antithrombotic effect of an anti-glycoprotein IIB/IIIA antibody in primate lethal thrombosis.", Thromb Res. May 1, 1993;70(3):245-254.

Kwakkenbos, MJ, et al., "Generation of stable monoclonal antibody-producing B cell receptor-positive human memory B cells by genetic programming.", Nat Med. 2010. 16(1):123-128.

Lee, E.C., et al., "Complete humanization of the mouse immunoglobulin loci enables efficient therapeutic antibody discovery." Nature Biotechnology (2014); 32(4): 356-363.

Lefranc, MP, "Unique database numbering system for immunogenetic analysis", Immunology Today, 18, 509 (1997). PMID: 9386342.

Lefranc, MP, "The IMGT unique numbering for immunoglobulins, T cell Receptors and Ig-like domains", The Immunologist. 1999; 7, 132-136.

Lefranc, MP, et al. "IMGT unique numbering for immunoglobulin and T cell receptor variable domains and Ig superfamily V-like domains", Dev. Comp. Immunol., 27, 55-77 (2003).

Musunuri, et al., "Increased Levels of Extracellular Microvesicle Markers and Decreased Levels of Endocytic/Exocytic Proteins in the Alzheimer's Disease Brain.", J Alzheimers Dis. Oct. 18, 2016;54(4):1671-1686.

Rajendra, et al., "A high cell density transient transfection system for therapeutic protein expression based on a CHO GS-knockout cell line: process development and product quality assessment." Biotechnol Bioeng. May 2015;112(5):977-986.

Seigneuret, et al., "Complete predicted three-dimensional structure of the facilitator transmembrane protein and hepatitis C virus receptor CD81: conserved and variable structural domains in the tetraspanin superfamily.", Biophys J. Jan. 1, 2006;90(1):212-227.

Takeda, et al., "Preventive role of tetraspanin CD9 in systemic inflammation of COPD. Am.J.Respir.", Cell Mol Biol. (2015); 53(6):751-760.

Van Lent, et al., "In vivo modulation of gene expression by lentiviral transduction in "human immune system" Rag2-/- gamma c -/- mice." Methods Mol Biol. 2010;595:87-115.

Verdegaal, et al., "Successful treatment of metastatic melanoma by adoptive transfer of blood-derived polyclonal tumor-specific CD4+ and CD8+ T cells in combination with low-dose interferon-alpha.", Cancer Immunol Immunother (2011); 60(7): 953-963.

Vidarsson, et al., "IgG subclasses and allotypes: from structure to effector functions.", Front Immunol. Oct. 20, 2014;5:520.

Wagner, et al., "Budesonide treatment of patients with collagenous colitis restores normal eosinophil and T-cell activity in the colon.", Inflamm.Bowel Dis. (2010); 16(7); 1118-1126.

Wagner, et al., "Bispecific antibody generated with sortase and click chemistry has broad antiinfluenza virus activity.", Proc Natl Acad Sci U S A. Nov. 25, 2014;111(47):16820-16825.

Yang, et al., "Protein Structure and Function Prediction Using I-TASSER.", Curr Protoc Bioinformatics. Dec. 17, 2015;52:5.8.1-15.

Zimmerman, et al., "Crystal Structure of a Full-Length Human Tetraspanin Reveals a Cholesterol-Binding Pocket.", Cell. Nov. 3, 2016;167(4):1041-1051.e11.

Van de Bovbenkamp, et al., "The Emerging Importance of IgG Fab Glycosylation in Immunity.", J Immunol 2016; 196:1435-1441.

Charrin, et al., "Tetraspanins at a glance.", J Cell Science (2014) 127, 3641-3648.

Hemler. "Tetraspanin proteins promote multiple cancer stages.", Nature Reviews Cancer, vol. 14, Jan. 2014, 49-60.

Murayama, et al., "Novel CD9-targeted therapies in gastric cancer." World J Gastroenterol Mar. 21, 2015; 21(11): 3206-3213.

Rubinstein, et al., "Anti-Platelet Antibody Interactions with FCγ Receptor.", Seminars in Thrombosis and Hemostasis, vol. 21, No. 1, 1995, 10-22.

J. Menendez, et al., "506 POSTER the apogenic anti-CD9 antibody, AR40A746.2.3, inhibits tumor growth in breast and pancreatic cancer and targets cancre stem cells in acute myeloid leukemia", European Journal of Cancer, Supplement, Oct. 1, 2008, vol. 6, No. 12., p. 161.

J Menendez, et al., "Anti-CD9 antibody, AR40A746.2.3, inhibits tumor growth in pancreatice and breast cancer models and recognizes CD9 on CD34+CD38-leukemic cancer stem cells", [American Association for Cancer Research, Proceedings of the Annual Meeting, Cancer Research, Apr. 2004, vol. 64, Issue 7, Supplement], American Institute for Cancer Research, Apr. 12, 2008, vol. 49, p. 949.

Kurzeder, C. et al., "CD9 promotes adeno-associated virus type 2 infection of mammary carcinoma cells with low cell surface expression of heparan sulphate proteoglycans", International Journal of Molecular Medicine, Feb. 2007;19: pp. 325-333.

* cited by examiner

Figure 2

CD9 sequence (UNIPROT) (SEQ ID NO: 19)

```
         10         20         30         40         50
    MPVKGGTKCI KYLLFGFNFI FWLAGIAVLA IGLWLRFDSQ TKSIFEQETN
         60         70         80         90        100
    NNNSSFYTGV YILIGAGALM MLVGFLGCCG AVQESQCMLG LFFGFLLVIF
        110        120        130        140        150
    AIEIAAAIWG YSHKDEVIKE VQEFYKDTYN KLKTKDEPQR ETLKAIHYAL
        160        170        180        190        200
    NCCGLAGGVE QFISDICPKK DVLETFTVKS CPDAIKEVFD NKFHIIGAVG
        210        220
    IGIAVVMIFG MIFSMILCCA IRRNREMV
```

Figure 3

NB: CDR numbering according to Kabat et al (1991)

AT14-012 (2H15-1A10)
Isotype IgG, Subtype IgG3, Light chain kappa

Variable region heavy chain

Recombined from gene segments:
IGHV3-9*01
IGHD3-3*01
IGHJ4*02

AMINO ACID:
FW1 EVQVVESGGGLVQPGRSLRLSCAASGFTFD (SEQ ID No: 59)
CDR1 DYAMH (SEQ ID No: 2)
FW2 WVRQAPGKGLEWVS (SEQ ID No: 61)
CDR2 GISWNSGSIVYADSVKG (SEQ ID No: 4)
FW3 RFTISRDNAKNSLYLQLNSLRAEDTAFYYCAK (SEQ ID No: 63)
CDR3 AVSGYYPYFDY (SEQ ID No: 6)
FW4 WGQGILVTVSS (SEQ ID No: 65)

NUCLEOTIDE:
FW1 gaa gtg cag gtg gtg gag tct ggg gga ggc ttg gta cag cct ggc agg tcc ctg aga ctc tcc tgt gca gcc tct gga ttc acc ttt gat (SEQ ID No: 58)

CDR1 gat tat gcc atg cac (SEQ ID No: 1)

FW2 tgg gtc cgg caa gct cca ggg aag ggc ctg gag tgg gtc tca (SEQ ID No: 60)

CDR2 ggt att agt tgg aat agt ggt agc ata gtc tat gcg gac tct gtg aag ggc (SEQ ID No: 3)

FW3 cga ttc acc atc tcc aga gac aac gcc aag aac tcc ctg tat ctg caa ctg aac agt ctg aga gct gag gac acg gcc ttc tat tac tgt gca aaa (SEQ ID No: 62)

CDR3 gcc gtg agt ggt tat tat ccc tac ttt gac tac (SEQ ID No: 5)

FW4 tgg ggc cag gga att ttg gtc acc gtc tcc tca (SEQ ID No: 64)

Variable region light chain

Recombined from gene segments:
IGKV4-1*01
IGKJ5*01

AMINO ACID:
FW1 DIVMTQSPDSLSVSLGERATINC (SEQ ID No: 67)
CDR1 KSSQSVLYSSNNKNYLG (SEQ ID No: 8)
FW2 WYQQKPGQPPKLLIY (SEQ ID No: 69)
CDR2 WASTRES (SEQ ID No: 10)
FW3 GVPDRFSGSGSGTDFTLTISSLQAEDVAVYYC (SEQ ID No: 71)
CDR3 QQYYTTP (SEQ ID No: 12)
FW4 STFGQGTRLEIK (SEQ ID No: 73)

NUCLEOTIDE:
FW1 gac atc gtg atg acc cag tct cca gac tcc ctg tct gtg tct ctg ggc gag agg gcc acc atc aac tgc (SEQ ID No: 66)

CDR1 aag tcc agc cag agt gtt tta tac agc tcc aac aat aag aac tac tta ggt (SEQ ID No: 7)

FW2 tgg tac cag cag aaa cca gga cag cct cct aag ctg ctc att tac (SEQ ID No: 68)

CDR2 tgg gca tct acc cgg gaa tcc (SEQ ID No: 9)

FW3 ggg gtc cct gac cga ttc agt ggc agc ggg tct ggg aca gat ttc act ctc acc atc agc agc ctg cag gct gaa gat gtg gca gtt tat tac tgt (SEQ ID No: 70)

CDR3 cag caa tat tat act act cct (SEQ ID No: 11)

FW4 tcc acc ttc ggc caa ggg aca cga ctg gag att aaa (SEQ ID No: 72)

- = AT10-002
+ = AT14-012

Figure 9E-G
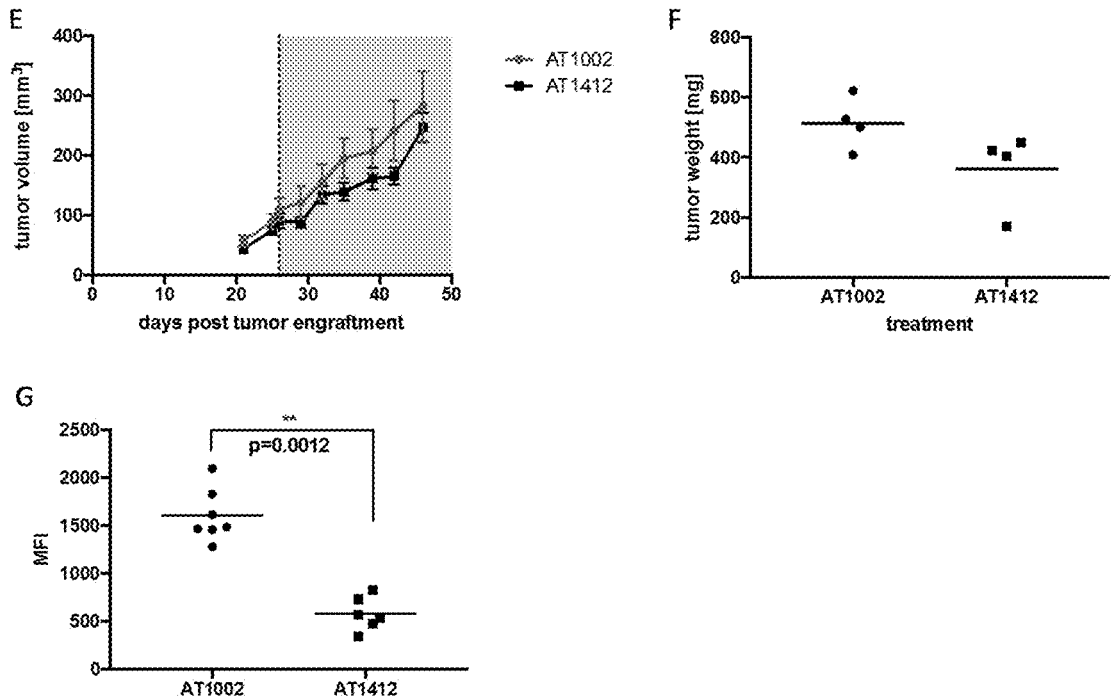
Figure 10A
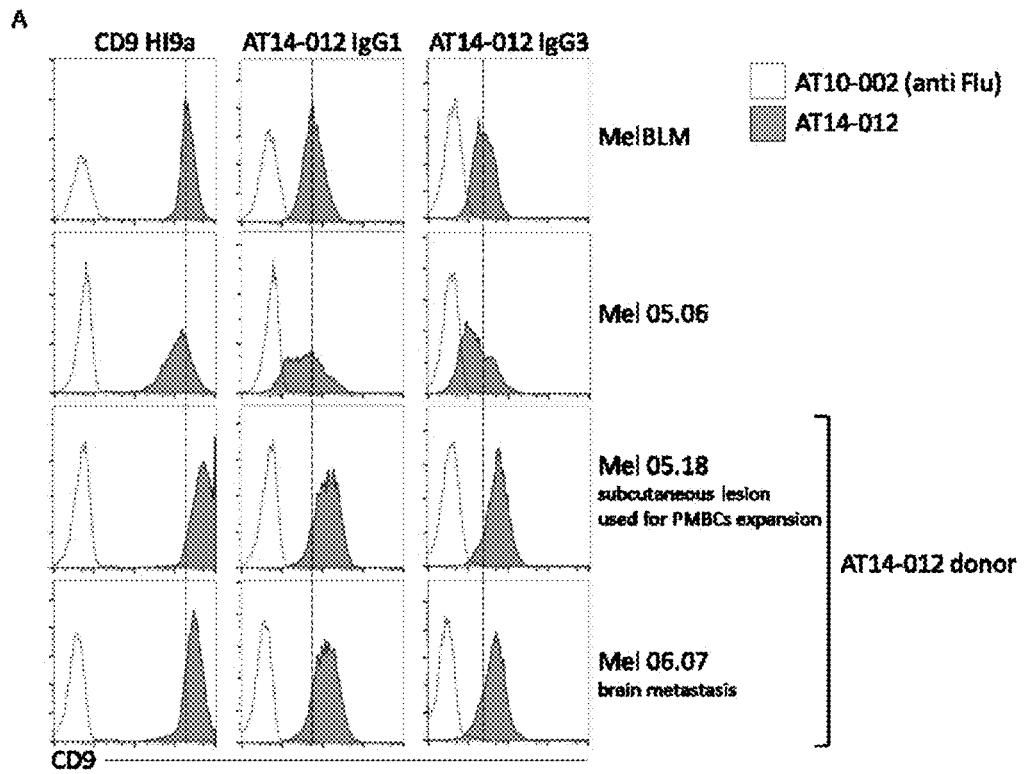

Figure 16A
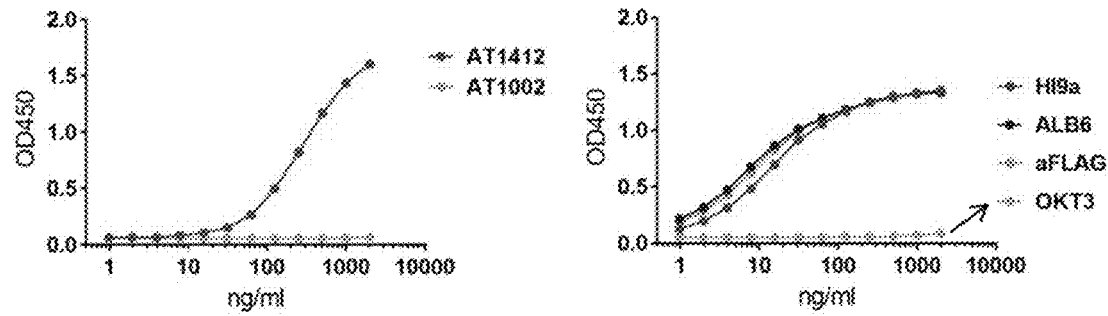
Figure 16B
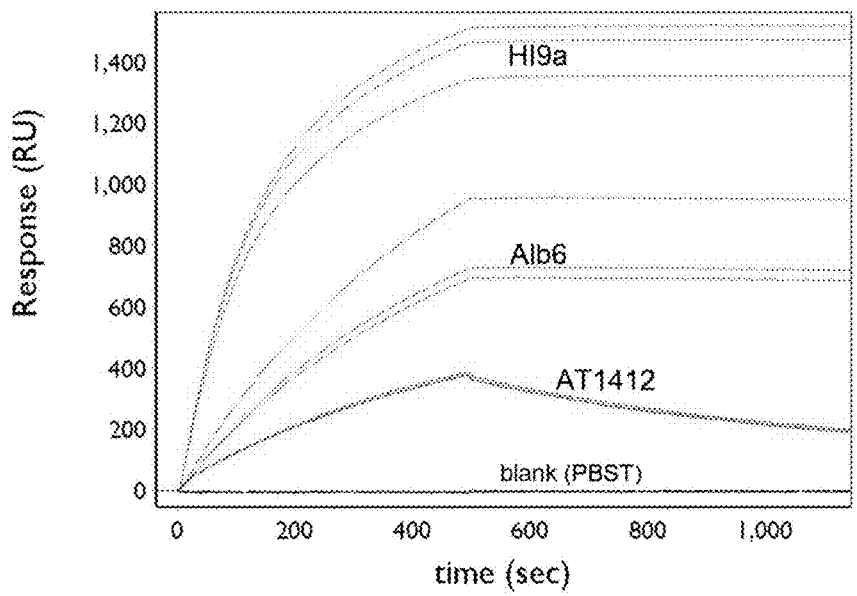
Figure 16C
| Antibody: | $k_a$ | $k_d$ | $K_D$ |
|---|---|---|---|
| AT1412 | 1.62 (± 0.52) | 71.0 (± 20.6) | 44,300 (± 1,500) |
| HI9a | 43.0 (± 2.1) | *0.1 \ | 2.33 (± 0.11)** |
| ALB6 | 15.1 (± 1.3) | 2.16 (± 0.30) | 145 (± 8) |

Figure 17B

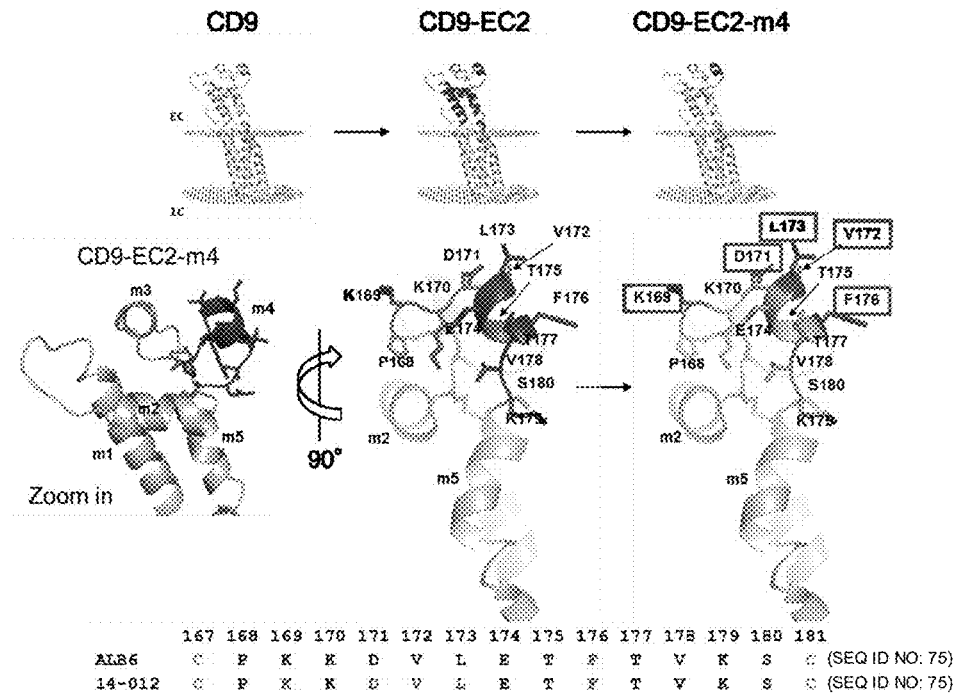

Figure 17C

```
            23         33         43         53         63         73         83
Human       LAGIAVLAIG LWLRFDSQTK SIFEQETNNN NSSFYTGVYI LIGAGALMML VGFLGCCGAV QESQCMLGLF
Gibbon      .......... .......... .......... .......... .......... .......... ..........
Gorilla     .......... .......... .......... .......... .......... .......... ..........
Orangutan   .......... .......... .......... .......... .......... .......... ..........
Chimpansee  .......... .......... .......... .......... .......... .......... ..........
Macaque     .......... .......... .......... .......... .......... .......... ..........
Baboon      .......... .......... .......... .......... .......... .......... ..........
Rabbit      .......... ......DK.. -......... .......... .......... .......... ..........
Mouse       .......... .......... ......--.. H......... .......... .......... ..........

93        103        113        123        133        143        153
Human       FGFLLVIFAI EIAAAIWGYS HKDEVIKEVQ EFYKDTYNKL KTKDEPQRET LKAIHYALNC CGLAGGVEQF
Gibbon      .......... .......... .......... .......... .......... .......... ..........
Gorilla     .......... .......... .......... .......... .....L.... .......... ..........
Orangutan   .......... .......... .......... .......... .......... .......... ...V......
Chimpansee  .......... .......... .......... .......... .......... .......... ..........
Macaque     .......... .......... .......... .......... .......... ........D. ..........
Baboon      .......... .......... .......... .......... .......... ........D. .....A....
Rabbit      .S........ ..T....... .......... .......... .N........ ........D. ..M.......
Mouse       .......... .....V..T. .......L.. ........Q. RS........ .....M..D. ..I..PL...

163        173        183        193        203        213        223
Human       ISDIFPKDV FETTVKSSP DAIKEVFDNK FHIIGAVGIG IAVVMIFGMI FSMILCCAIR RNREMV  (SEQ ID NO: 76)
Gibbon      .......... .......... .......... .......... .......... .......... ......  (SEQ ID NO: 76)
Gorilla     .......... .......... .......... .......... .......... .......... ......  (SEQ ID NO: 77)
Orangutan   ......C... .......... .......... .......... .......... .......... ......  (SEQ ID NO: 78)
Chimpansee  ......C... .......... .......... .......... .......... .......... ......  (SEQ ID NO: 79)
Macaque     .......... .I........ .......... .......... .......... .......... ......  (SEQ ID NO: 80)
Baboon      .......... .I.P..A... .......... .......... .......... .......... ......  (SEQ ID NO: 81)
Rabbit      .......1.. S.Q....E.. ......V... .......... .......... .S........ ......  (SEQ ID NO: 82)
Mouse       ...T...Q.. S.Q..P..E. .S...N.... .......... .......... .S........ ......  (SEQ ID NO: 83)
```

Figure 18C

| Group 1: faster association (ka), slower dissociation (kd) | | | | Mutations: | |
|---|---|---|---|---|---|
| | ka | kd | KD | Heavy chain | Light chain |
| 1D5 | 281.8E+3 | 6.41E-04 | 2.3E-9 | H40Y | - |
| 1F5 | 232.8E+3 | 8.36E-04 | 3.8E-9 | Y112F | - |
| 4H10 | 190.3E+3 | 1.06E-03 | 6.1E-9 | H40Y | L120V |
| 10B9 | 267.6E+3 | 6.67E-04 | 2.5E-9 | H40Y - A45V (+silent) | - |
| 10D1 | 230.9E+3 | 9.04E-04 | 3.9E-9 | H40Y | - |

| Group 2: faster association (ka), faster dissociation (kd) | | | | Mutations: | |
|---|---|---|---|---|---|
| | ka | kd | KD | Heavy chain | Light chain |
| 2D12 | 896.5E+3 | 4.6E-3 | 5.2E-9 | D116H | - |
| 4D4 | 99.5E+3 | 1.6E-3 | 15.9E-9 | - | T66I - L94P |
| 6E10 | 498.0E+3 | 3.1E-3 | 10.5E-9 | T29N | - |
| 9E5 | 925.4E+3 | 6.1E-3 | 6.7E-9 | D116H | S28N |

| Group 3: no clear difference | | | | Mutations: | |
|---|---|---|---|---|---|
| | ka | kd | KD | Heavy chain | Light chain |
| 1C9 | 52.7E+3 | 2.2E-3 | 41.9E-9 | Q3P | - (+silent) |
| 2H10 | 60.7E+3 | 2.1E-3 | 33.9E-9 | A24T | - |
| 9A9 | 48.4E+3 | 2.1E-3 | 43.4E-9 | G27R | - |
| 9D12 | 42.7E+3 | 1.1E-3 | 26.0E-9 | S64N - V66I | - |

| 2H15 similar | | | | Mutations: | |
|---|---|---|---|---|---|
| | ka | kd | KD | Heavy chain | Light chain |
| 1G2 | 33.4E+3 | 2.4E-3 | 73.0E-9 | - | - |
| 1G3 | 33.4E+3 | 2.4E-3 | 73.0E-9 | - | - |
| 1G4 | 33.4E+3 | 2.4E-3 | 73.0E-9 | - | - |
| 1G5 | 33.4E+3 | 2.4E-3 | 73.0E-9 | A96G (+silent) | - |

| disPROVE | | | | Mutations: | |
|---|---|---|---|---|---|
| | ka | kd | KD | Heavy chain | Light chain |
| 1E3 | - | - | - | V108L | - |
| 1E4 | - | - | - | Y37C - (+silent) - A45V - K85R - G110A - G121A | - |
| 1E5 | - | - | - | Y117C | - |
| 1F12 | - | - | - | S62T | - |
| 2A3 | - | - | - | (+silent) - G110D | - (+silent) |
| 5B1 | - | - | - | G55S - (+silent) - A96V - T125I | - |

```
                                        CDR1                              CDR2
                 1        12       20   26---------40   45       50   55 --------67
1412-WT          EVQVVESGGG LVQPGRSLRL SCAASGFTFD DYAMHWVRQA PGKGLEWVSG ISWNSGSIYY
H40Y             .......... .......... .......... ....Y..... .......... ..........
Y112F            .......... .......... .......... .......... .......... ..........
H40Y-Y112F       .......... .......... .......... ....Y..... .......... ..........
D116H            .......... .......... .......... .......... .......... ..........
T29N             .......... .......... ......N... .......... .......... ..........
D116H-T29N       .......... .......... ......N... .......... .......... ..........
H40Y-Y112F-D116H-T29N .......... .......... ......N... ....Y..... .......... ..........
G110D            .......... .......... .......... .......... .......... ..........

CDR3
                  70        80       90       100 104---------------120       128
1412-WT           ADSVKGRFTI SRDNAKNSLY LQLNSLRAED TAFYYCAKAV SGYYPYFDYW GQGILVTVSS  (SEQ ID NO: 14)
H40Y              .......... .......... .......... .......... .......... ..........  (SEQ ID NO: 84)
Y112F             .......... .......... .......... ...F...... .......... ..........  (SEQ ID NO: 85)
H40Y-Y112F        .......... .......... .......... ...F...... .......... ..........  (SEQ ID NO: 86)
D116H             .......... .......... .......... .......... ....H..... ..........  (SEQ ID NO: 87)
T29N              .......... .......... .......... .......... .......... ..........  (SEQ ID NO: 88)
D116H-T29N        .......... .......... .......... .......... ....H..... ..........  (SEQ ID NO: 89)
H40Y-Y112F-D116H-T29N .......... .......... .......... ...F...... ....H..... ..........  (SEQ ID NO: 90)
G110D             .......... .......... .......... .D........ .......... ..........  (SEQ ID NO: 91)
```

Figure 19C
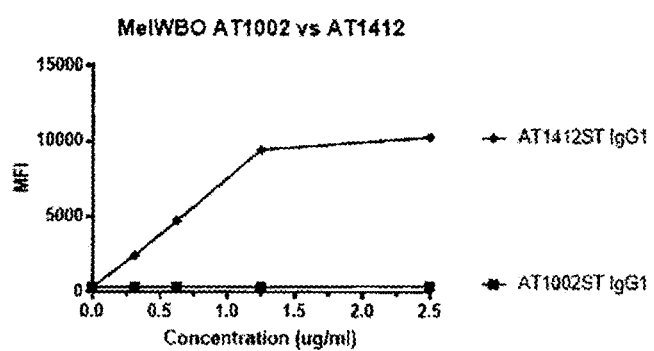
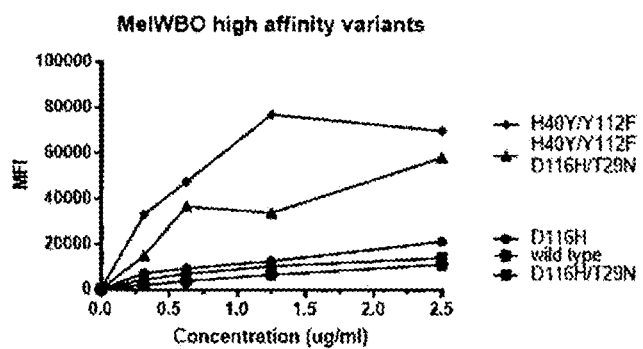

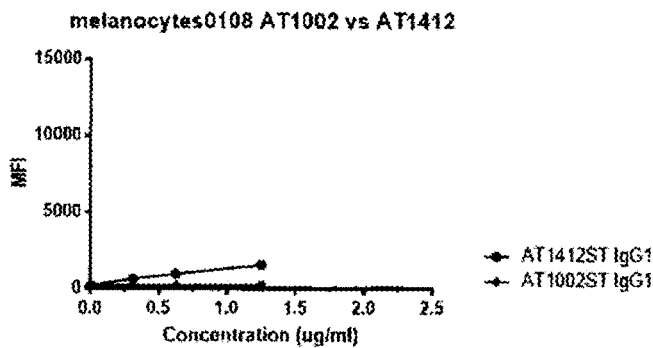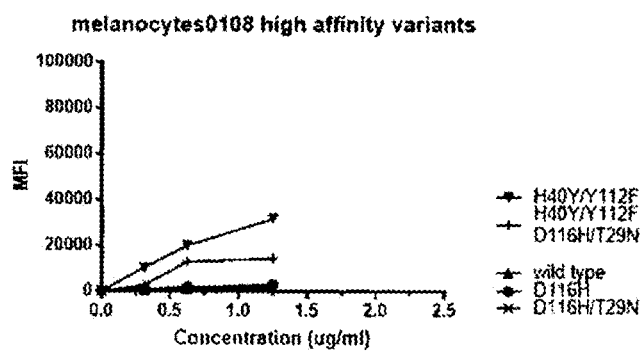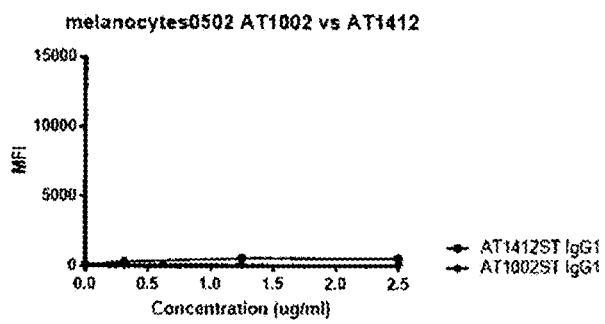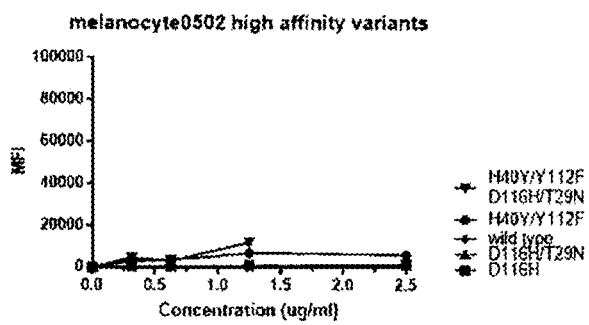
Figure 19C continued

SEQUENCE LISTING

```
<160> NUMBER OF SEQ ID NOS: 103

<210> SEQ ID NO 1
<211> LENGTH: 15
<212> TYPE: DNA
<213> ORGANISM: Artificial Sequence
<220> FEATURE:
<223> OTHER INFORMATION: heavy chain CDR1
<220> FEATURE:
<221> NAME/KEY: CDS
```

```
<222> LOCATION: (1)..(15)

<400> SEQUENCE: 1 gat tat gcc atg cac                                               15
Asp Tyr Ala Met His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Tyr Ala Met His
1               5

<210> SEQ ID NO 3
<211> LENGTH: 51
<212> TYPE: DNA
<213> ORGANISM: Artificial Sequence
<220> FEATURE:
<223> OTHER INFORMATION: heavy chain CDR2
<220> FEATURE:
<221> NAME/KEY: CDS
<222> LOCATION: (1)..(51)

<400> SEQUENCE: 3 ggt att agt tgg aat agt ggt agc ata gtc tat gcg gac tct gtg aag   48
Gly Ile Ser Trp Asn Ser Gly Ser Ile Val Tyr Ala Asp Ser Val Lys
1               5                   10                  15 ggc                                                               51
Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Gly Ile Ser Trp Asn Ser Gly Ser Ile Val Tyr Ala Asp Ser Val Lys
1               5                   10                  15

Gly

<210> SEQ ID NO 5
<211> LENGTH: 33
<212> TYPE: DNA
<213> ORGANISM: Artificial Sequence
<220> FEATURE:
<223> OTHER INFORMATION: heavy chain CDR3
<220> FEATURE:
<221> NAME/KEY: CDS
<222> LOCATION: (1)..(33)

<400> SEQUENCE: 5 gcc gtg agt ggt tat tat ccc tac ttt gac tac                       33
Ala Val Ser Gly Tyr Tyr Pro Tyr Phe Asp Tyr
1               5                   10

<210> SEQ ID NO 6
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 6

Ala Val Ser Gly Tyr Tyr Pro Tyr Phe Asp Tyr
1               5                   10

<210> SEQ ID NO 7
<211> LENGTH: 51
<212> TYPE: DNA
<213> ORGANISM: Artificial Sequence
<220> FEATURE:
<223> OTHER INFORMATION: light chain CDR1
<220> FEATURE:
<221> NAME/KEY: CDS
<222> LOCATION: (1)..(51)

<400> SEQUENCE: 7 aag tcc agc cag agt gtt tta tac agc tcc aac aat aag aac tac tta    48
Lys Ser Ser Gln Ser Val Leu Tyr Ser Ser Asn Asn Lys Asn Tyr Leu
1               5                   10                  15 ggt                                                                51
Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Lys Ser Ser Gln Ser Val Leu Tyr Ser Ser Asn Asn Lys Asn Tyr Leu
1               5                   10                  15

Gly

<210> SEQ ID NO 9
<211> LENGTH: 21
<212> TYPE: DNA
<213> ORGANISM: Artificial Sequence
<220> FEATURE:
<223> OTHER INFORMATION: light chain CDR2
<220> FEATURE:
<221> NAME/KEY: CDS
<222> LOCATION: (1)..(21)

<400> SEQUENCE: 9 tgg gca tct acc cgg gaa tcc                                        21
Trp Ala Ser Thr Arg Glu Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Trp Ala Ser Thr Arg Glu Ser
1               5

<210> SEQ ID NO 11
<211> LENGTH: 21
<212> TYPE: DNA
<213> ORGANISM: Artificial Sequence
<220> FEATURE:
<223> OTHER INFORMATION: light chain CDR3

```
<220> FEATURE:
<221> NAME/KEY: CDS
<222> LOCATION: (1)..(21)

<400> SEQUENCE: 11 cag caa tat tat act act cct                                          21
Gln Gln Tyr Tyr Thr Thr Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Gln Gln Tyr Tyr Thr Thr Pro
1               5

<210> SEQ ID NO 13
<211> LENGTH: 360
<212> TYPE: DNA
<213> ORGANISM: Artificial Sequence
<220> FEATURE:
<223> OTHER INFORMATION: AT14-012 heavy chain
<220> FEATURE:
<221> NAME/KEY: CDS
<222> LOCATION: (1)..(360)
<220> FEATURE:
<221> NAME/KEY: misc_feature
<222> LOCATION: (1)..(90)
<223> OTHER INFORMATION: FW1
<220> FEATURE:
<221> NAME/KEY: misc_feature
<222> LOCATION: (106)..(147)
<223> OTHER INFORMATION: FW2
<220> FEATURE:
<221> NAME/KEY: misc_feature
<222> LOCATION: (198)..(294)
<223> OTHER INFORMATION: FW3
<220> FEATURE:
<221> NAME/KEY: misc_feature
<222> LOCATION: (328)..(360)
<223> OTHER INFORMATION: FW4

<400> SEQUENCE: 13 gaa gtg cag gtg gtg gag tct ggg gga ggc ttg gta cag cct ggc agg     48
Glu Val Gln Val Val Glu Ser Gly Gly Gly Leu Val Gln Pro Gly Arg
1               5                   10                  15 tcc ctg aga ctc tcc tgt gca gcc tct gga ttc acc ttt gat gat tat     96
Ser Leu Arg Leu Ser Cys Ala Ala Ser Gly Phe Thr Phe Asp Asp Tyr
            20                  25                  30 gcc atg cac tgg gtc cgg caa gct cca ggg aag ggc ctg gag tgg gtc    144
Ala Met His Trp Val Arg Gln Ala Pro Gly Lys Gly Leu Glu Trp Val
        35                  40                  45 tca ggt att agt tgg aat agt ggt agc ata gtc tat gcg gac tct gtg    192
Ser Gly Ile Ser Trp Asn Ser Gly Ser Ile Val Tyr Ala Asp Ser Val
    50                  55                  60 aag ggc cga ttc acc atc tcc aga gac aac gcc aag aac tcc ctg tat    240
Lys Gly Arg Phe Thr Ile Ser Arg Asp Asn Ala Lys Asn Ser Leu Tyr
65                  70                  75                  80 ctg caa ctg aac agt ctg aga gct gag gac acg gcc ttc tat tac tgt    288
Leu Gln Leu Asn Ser Leu Arg Ala Glu Asp Thr Ala Phe Tyr Tyr Cys
                85                  90                  95 gca aaa gcc gtg agt ggt tat tat ccc tac ttt gac tac tgg ggc cag    336
Ala Lys Ala Val Ser Gly Tyr Tyr Pro Tyr Phe Asp Tyr Trp Gly Gln
            100                 105                 110
```

```
gga att ttg gtc acc gtc tcc tca                                          360
Gly Ile Leu Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Tyr Pro Tyr Phe Asp Tyr Trp Gly Gln
            100                 105                 110

Gly Ile Leu Val Thr Val Ser Ser
        115                 120

<210> SEQ ID NO 15
<211> LENGTH: 339
<212> TYPE: DNA
<213> ORGANISM: Artificial Sequence
<220> FEATURE:
<223> OTHER INFORMATION: AT14-012 light chain
<220> FEATURE:
<221> NAME/KEY: CDS
<222> LOCATION: (1)..(339)
<220> FEATURE:
<221> NAME/KEY: misc_feature
<222> LOCATION: (1)..(69)
<223> OTHER INFORMATION: FW1
<220> FEATURE:
<221> NAME/KEY: misc_feature
<222> LOCATION: (120)..(165)
<223> OTHER INFORMATION: FW2
<220> FEATURE:
<221> NAME/KEY: misc_feature
<222> LOCATION: (186)..(282)
<223> OTHER INFORMATION: FW3
<220> FEATURE:
<221> NAME/KEY: misc_feature
<222> LOCATION: (304)..(339)
<223> OTHER INFORMATION: FW4

<400> SEQUENCE: 15 gac atc gtg atg acc cag tct cca gac tcc ctg tct gtg tct ctg ggc          48
Asp Ile Val Met Thr Gln Ser Pro Asp Ser Leu Ser Val Ser Leu Gly
1               5                   10                  15 gag agg gcc acc atc aac tgc aag tcc agc cag agt gtt tta tac agc          96
Glu Arg Ala Thr Ile Asn Cys Lys Ser Ser Gln Ser Val Leu Tyr Ser
            20                  25                  30 tcc aac aat aag aac tac tta ggt tgg tac cag cag aaa cca gga cag         144
Ser Asn Asn Lys Asn Tyr Leu Gly Trp Tyr Gln Gln Lys Pro Gly Gln
        35                  40                  45
```

-continued

```
cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
 50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat act act cct tcc acc ttc ggc caa ggg aca cga ctg gag att     336
Tyr Tyr Thr Thr Pro Ser Thr Phe Gly Gln Gly Thr Arg Leu Glu Ile
            100                 105                 110 aaa                                                                  339
Lys
```

<210> SEQ ID NO 16
<211> LENGTH: 113
<212> TYPE: PRT
<213> ORGANISM: Artificial Sequence
<220> FEATURE:
<223> OTHER INFORMATION: Synthetic Construct

<400> SEQUENCE: 16

```
Asp Ile Val Met Thr Gln Ser Pro Asp Ser Leu Ser Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Gly Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Ser Thr Phe Gly Gln Gly Thr Arg Leu Glu Ile
            100                 105                 110

Lys
```

<210> SEQ ID NO 17
<211> LENGTH: 5
<212> TYPE: PRT
<213> ORGANISM: Artificial Sequence
<220> FEATURE:
<223> OTHER INFORMATION: target of mAb7

<400> SEQUENCE: 17

```
Pro Lys Lys Asp Val
1               5
```

<210> SEQ ID NO 18
<211> LENGTH: 7
<212> TYPE: PRT
<213> ORGANISM: Artificial Sequence
<220> FEATURE:
<223> OTHER INFORMATION: target of ES5.2D8

<400> SEQUENCE: 18

```
Gly Leu Trp Leu Arg Phe Asp
1               5
```

<210> SEQ ID NO 19
<211> LENGTH: 228
<212> TYPE: PRT
<213> ORGANISM: Homo sapiens

<400> SEQUENCE: 19

```
Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225
```

<210> SEQ ID NO 20
<211> LENGTH: 22
<212> TYPE: PRT
<213> ORGANISM: Artificial Sequence
<220> FEATURE:
<223> OTHER INFORMATION: 3x FLAG-tag

<400> SEQUENCE: 20

```
Asp Tyr Lys Asp His Asp Gly Asp Tyr Lys Asp His Asp Ile Asp Tyr
1               5                   10                  15

Lys Asp Asp Asp Asp Lys
            20
```

<210> SEQ ID NO 21
<211> LENGTH: 5
<212> TYPE: PRT
<213> ORGANISM: Artificial Sequence
<220> FEATURE:
<223> OTHER INFORMATION: variant CDR1 heavy chain

<400> SEQUENCE: 21

Asp Tyr Ala Met Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: variant CDR3  heavy chain

<400> SEQUENCE: 22

Ala Val Ser Gly Tyr Phe Pro Tyr Phe Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: variant CDR3 heavy chain

<400> SEQUENCE: 23

Ala Val Ser Gly Tyr Tyr Pro Tyr Phe His Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: variant CDR3 heavy chain

<400> SEQUENCE: 24

Ala Val Ser Gly Tyr Phe Pro Tyr Phe His Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: variant CDR2 light chain

<400> SEQUENCE: 25

Trp Ala Ser Ile Arg Glu Ser
1               5

<210> SEQ ID NO 26
<211> LENGTH: 120
<212> TYPE: PRT
<213> ORGANISM: Artificial Sequence
<220> FEATURE:
<223> OTHER INFORMATION: variant heavy chain

<400> SEQUENCE: 26

Glu Val Gln Val Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: variant heavy chain

<400> SEQUENCE: 27

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: variant heavy chain

<400> SEQUENCE: 28

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe His Tyr Trp Gly Gln
            100                 105                 110

Gly Ile Leu Val Thr Val Ser Ser
        115                 120
```

```
<210> SEQ ID NO 29
<211> LENGTH: 120
<212> TYPE: PRT
<213> ORGANISM: Artificial Sequence
<220> FEATURE:
<223> OTHER INFORMATION: variant heavy chain

<400> SEQUENCE: 29

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: variant heavy chain

<400> SEQUENCE: 30

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
        115                 120

<210> SEQ ID NO 31
<211> LENGTH: 120
<212> TYPE: PRT
<213> ORGANISM: Artificial Sequence
<220> FEATURE:
<223> OTHER INFORMATION: variant heavy chain

<400> SEQUENCE: 31

Glu Val Gln Val Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
         20                  25                  30

Ala Met Tyr Trp Val Arg Gln Ala Pro Gly Lys Gly Leu Glu Trp Val
             35                  40                  45

Ser Gly Ile Ser Trp Asn Ser Gly Ser Ile Val Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Phe Tyr Tyr Cys
                 85                  90                  95

Ala Lys Ala Val Ser Gly Tyr Phe Pro Tyr Phe His Tyr Trp Gly Gln
            100                 105                 110

Gly Ile Leu Val Thr Val Ser Ser
            115                 120
```

<210> SEQ ID NO 32
<211> LENGTH: 113
<212> TYPE: PRT
<213> ORGANISM: Artificial Sequence
<220> FEATURE:
<223> OTHER INFORMATION: variant light chain

<400> SEQUENCE: 32

```
Asp Ile Val Met Thr Gln Ser Pro Asp Ser Leu Ser Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Gly Trp Tyr Gln Gln Lys Pro Gly Gln
         35                  40                  45

Pro Pro Lys Leu Leu Ile Tyr Trp Ala Ser Ile Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Ser Thr Phe Gly Gln Gly Thr Arg Leu Glu Ile
            100                 105                 110

Lys
```

<210> SEQ ID NO 33
<211> LENGTH: 22
<212> TYPE: PRT
<213> ORGANISM: Artificial Sequence
<220> FEATURE:
<223> OTHER INFORMATION: 3X FLAG tag

<400> SEQUENCE: 33

```
Asp Tyr Lys Asp His Asp Gly Asp Tyr Lys Asp His Asp Ile Asp Tyr
 1               5                  10                  15

Lys Asp Asp Asp Asp Lys
             20
```

<210> SEQ ID NO 34
<211> LENGTH: 12
<212> TYPE: PRT
<213> ORGANISM: Artificial Sequence
<220> FEATURE:
<223> OTHER INFORMATION: SortaseHIS tag

```
<400> SEQUENCE: 34

Leu Pro Glu Thr Gly Gly His His His His His His
1               5                   10

<210> SEQ ID NO 35
<211> LENGTH: 13
<212> TYPE: PRT
<213> ORGANISM: Artificial Sequence
<220> FEATURE:
<223> OTHER INFORMATION: m4 region of CD9

<400> SEQUENCE: 35

Pro Lys Lys Asp Val Leu Glu Thr Phe Thr Val Lys Ser
1               5                   10

<210> SEQ ID NO 36
<211> LENGTH: 17
<212> TYPE: PRT
<213> ORGANISM: Artificial Sequence
<220> FEATURE:
<223> OTHER INFORMATION: biotin moiety
<220> FEATURE:
<221> NAME/KEY: DISULFID
<222> LOCATION: (1)..(17)

<400> SEQUENCE: 36

Cys Ser Pro Lys Lys Asp Val Leu Glu Thr Phe Thr Val Lys Ser Ser
1               5                   10                  15
Cys

<210> SEQ ID NO 37
<211> LENGTH: 20
<212> TYPE: DNA
<213> ORGANISM: Artificial Sequence
<220> FEATURE:
<223> OTHER INFORMATION: Ig variant

<400> SEQUENCE: 37
tgcatctgta tccagcgcca                                               20

<210> SEQ ID NO 38
<211> LENGTH: 20
<212> TYPE: DNA
<213> ORGANISM: Artificial Sequence
<220> FEATURE:
<223> OTHER INFORMATION: Ig variant

<400> SEQUENCE: 38
ctcagggatg taagctgact                                               20

<210> SEQ ID NO 39
<211> LENGTH: 22
<212> TYPE: DNA
<213> ORGANISM: Artificial Sequence
<220> FEATURE:
<223> OTHER INFORMATION: Ig variant

<400> SEQUENCE: 39
caccaagggc ccatcggtct tc                                            22

<210> SEQ ID NO 40
<211> LENGTH: 18
<212> TYPE: DNA
<213> ORGANISM: Artificial Sequence
<220> FEATURE:
<223> OTHER INFORMATION: Ig variant
```

```
<400> SEQUENCE: 40
tcattacccg gagacagg                                                        18

<210> SEQ ID NO 41
<211> LENGTH: 20
<212> TYPE: DNA
<213> ORGANISM: Artificial Sequence
<220> FEATURE:
<223> OTHER INFORMATION: Ig variant

<400> SEQUENCE: 41
ccatggagtt gggactgagc                                                      20

<210> SEQ ID NO 42
<211> LENGTH: 22
<212> TYPE: DNA
<213> ORGANISM: Artificial Sequence
<220> FEATURE:
<223> OTHER INFORMATION: Ig variant

<400> SEQUENCE: 42
caccatggar ytkkgrctbh gc                                                   22

<210> SEQ ID NO 43
<211> LENGTH: 24
<212> TYPE: DNA
<213> ORGANISM: Artificial Sequence
<220> FEATURE:
<223> OTHER INFORMATION: Ig variant

<400> SEQUENCE: 43
gtccaccttg gtgttgctgg gctt                                                 24

<210> SEQ ID NO 44
<211> LENGTH: 20
<212> TYPE: DNA
<213> ORGANISM: Artificial Sequence
<220> FEATURE:
<223> OTHER INFORMATION: Ig variant

<400> SEQUENCE: 44
ctgctgaggg agtagagtcc                                                      20

<210> SEQ ID NO 45
<211> LENGTH: 21
<212> TYPE: DNA
<213> ORGANISM: Artificial Sequence
<220> FEATURE:
<223> OTHER INFORMATION: Ig variant

<400> SEQUENCE: 45
ggtgtgcacg ccgctggtca g                                                    21

<210> SEQ ID NO 46
<211> LENGTH: 21
<212> TYPE: DNA
<213> ORGANISM: Artificial Sequence
<220> FEATURE:
<223> OTHER INFORMATION: Ig variant

<400> SEQUENCE: 46
gtgtccagtg tgaagtgcag g                                                    21

<210> SEQ ID NO 47
```

```
<211> LENGTH: 21
<212> TYPE: DNA
<213> ORGANISM: Artificial Sequence
<220> FEATURE:
<223> OTHER INFORMATION: Ig variant

<400> SEQUENCE: 47
gggataataa ccactcacgg c                                              21

<210> SEQ ID NO 48
<211> LENGTH: 21
<212> TYPE: DNA
<213> ORGANISM: Artificial Sequence
<220> FEATURE:
<223> OTHER INFORMATION: Ig variant

<400> SEQUENCE: 48
gtagggataa taaccactca c                                              21

<210> SEQ ID NO 49
<211> LENGTH: 20
<212> TYPE: DNA
<213> ORGANISM: Artificial Sequence
<220> FEATURE:
<223> OTHER INFORMATION: Ig variant

<400> SEQUENCE: 49
gtcaaagtag ggataataac                                                20

<210> SEQ ID NO 50
<211> LENGTH: 18
<212> TYPE: DNA
<213> ORGANISM: Artificial Sequence
<220> FEATURE:
<223> OTHER INFORMATION: Ig variant

<400> SEQUENCE: 50
ccagtagtca aagtaggg                                                  18

<210> SEQ ID NO 51
<211> LENGTH: 21
<212> TYPE: DNA
<213> ORGANISM: Artificial Sequence
<220> FEATURE:
<223> OTHER INFORMATION: Ig variant

<400> SEQUENCE: 51
accatggtgt tgcagaccca g                                              21

<210> SEQ ID NO 52
<211> LENGTH: 22
<212> TYPE: DNA
<213> ORGANISM: Artificial Sequence
<220> FEATURE:
<223> OTHER INFORMATION: Ig variant

<400> SEQUENCE: 52
tyyctsytsc tytggatctc tg                                             22

<210> SEQ ID NO 53
<211> LENGTH: 24
<212> TYPE: DNA
<213> ORGANISM: Artificial Sequence
<220> FEATURE:
<223> OTHER INFORMATION: Ig variant

<400> SEQUENCE: 53
```

```
acactctccc ctgttgaagc tctt                                              24
```

<210> SEQ ID NO 54
<211> LENGTH: 19
<212> TYPE: DNA
<213> ORGANISM: Artificial Sequence
<220> FEATURE:
<223> OTHER INFORMATION: Ig variant

<400> SEQUENCE: 54

```
cagtctccag actccctgt                                                    19
```

<210> SEQ ID NO 55
<211> LENGTH: 21
<212> TYPE: DNA
<213> ORGANISM: Artificial Sequence
<220> FEATURE:
<223> OTHER INFORMATION: Ig variant

<400> SEQUENCE: 55

```
ggccgaaggt ggaaggagta g                                                 21
```

<210> SEQ ID NO 56
<211> LENGTH: 22
<212> TYPE: DNA
<213> ORGANISM: Artificial Sequence
<220> FEATURE:
<223> OTHER INFORMATION: Ig variant

<400> SEQUENCE: 56

```
gtcccttggc cgaaggtgga ag                                                22
```

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57

```
tgtcccttgg ccgaaggtgg                                                   20
```

<210> SEQ ID NO 58
<211> LENGTH: 90
<212> TYPE: DNA
<213> ORGANISM: Artificial Sequence
<220> FEATURE:
<223> OTHER INFORMATION: AT14-012 FW1 heavy chain
<220> FEATURE:
<221> NAME/KEY: CDS
<222> LOCATION: (1)..(90)

<400> SEQUENCE: 58

```
gaa gtg cag gtg gtg gag tct ggg gga ggc ttg gta cag cct ggc agg         48
Glu Val Gln Val Val Glu Ser Gly Gly Gly Leu Val Gln Pro Gly Arg
1               5                   10                  15 tcc ctg aga ctc tcc tgt gca gcc tct gga ttc acc ttt gat              90
Ser Leu Arg Leu Ser Cys Ala Ala Ser Gly Phe Thr Phe Asp
            20                  25                  30
```

<210> SEQ ID NO 59
<211> LENGTH: 30
<212> TYPE: PRT
<213> ORGANISM: Artificial Sequence
<220> FEATURE:
<223> OTHER INFORMATION: Synthetic Construct

<400> SEQUENCE: 59

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 60
<211> LENGTH: 42
<212> TYPE: DNA
<213> ORGANISM: Artificial Sequence
<220> FEATURE:
<223> OTHER INFORMATION: AT14-012 FW2 heavy chain
<220> FEATURE:
<221> NAME/KEY: CDS
<222> LOCATION: (1)..(42)

<400> SEQUENCE: 60 tgg gtc cgg caa gct cca ggg aag ggc ctg gag tgg gtc tca      42
Trp Val Arg Gln Ala Pro Gly Lys Gly Leu Glu Trp Val Ser
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Trp Val Arg Gln Ala Pro Gly Lys Gly Leu Glu Trp Val Ser
1               5                   10

<210> SEQ ID NO 62
<211> LENGTH: 96
<212> TYPE: DNA
<213> ORGANISM: Artificial Sequence
<220> FEATURE:
<223> OTHER INFORMATION: AT14-012 FW3 heavy chain
<220> FEATURE:
<221> NAME/KEY: CDS
<222> LOCATION: (1)..(96)

<400> SEQUENCE: 62 cga ttc acc atc tcc aga gac aac gcc aag aac tcc ctg tat ctg caa      48
Arg Phe Thr Ile Ser Arg Asp Asn Ala Lys Asn Ser Leu Tyr Leu Gln
1               5                   10                  15 ctg aac agt ctg aga gct gag gac acg gcc ttc tat tac tgt gca aaa      96
Leu Asn Ser Leu Arg Ala Glu Asp Thr Ala Phe Tyr Tyr Cys Ala Lys
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Synthetic Construct

<400> SEQUENCE: 63

Arg Phe Thr Ile Ser Arg Asp Asn Ala Lys Asn Ser Leu Tyr Leu Gln
1               5                   10                  15

Leu Asn Ser Leu Arg Ala Glu Asp Thr Ala Phe Tyr Tyr Cys Ala Lys
            20                  25                  30

<210> SEQ ID NO 64
<211> LENGTH: 33

```
<212> TYPE: DNA
<213> ORGANISM: Artificial Sequence
<220> FEATURE:
<223> OTHER INFORMATION: AT14-012 FW4 heavy chain
<220> FEATURE:
<221> NAME/KEY: CDS
<222> LOCATION: (1)..(33)

<400> SEQUENCE: 64 tgg ggc cag gga att ttg gtc acc gtc tcc tca                         33
Trp Gly Gln Gly Ile Leu Val Thr Val Ser Ser
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Trp Gly Gln Gly Ile Leu Val Thr Val Ser Ser
1               5                   10

<210> SEQ ID NO 66
<211> LENGTH: 69
<212> TYPE: DNA
<213> ORGANISM: Artificial Sequence
<220> FEATURE:
<223> OTHER INFORMATION: AT14-012 FW1 light chain
<220> FEATURE:
<221> NAME/KEY: CDS
<222> LOCATION: (1)..(69)

<400> SEQUENCE: 66 gac atc gtg atg acc cag tct cca gac tcc ctg tct gtg tct ctg ggc    48
Asp Ile Val Met Thr Gln Ser Pro Asp Ser Leu Ser Val Ser Leu Gly
1               5                   10                  15 gag agg gcc acc atc aac tgc                                         69
Glu Arg Ala Thr Ile Asn Cys
            20

<210> SEQ ID NO 67
<211> LENGTH: 23
<212> TYPE: PRT
<213> ORGANISM: Artificial Sequence
<220> FEATURE:
<223> OTHER INFORMATION: Synthetic Construct

<400> SEQUENCE: 67

Asp Ile Val Met Thr Gln Ser Pro Asp Ser Leu Ser Val Ser Leu Gly
1               5                   10                  15

Glu Arg Ala Thr Ile Asn Cys
            20

<210> SEQ ID NO 68
<211> LENGTH: 45
<212> TYPE: DNA
<213> ORGANISM: Artificial Sequence
<220> FEATURE:
<223> OTHER INFORMATION: AT14-012 FW2 light chain
<220> FEATURE:
<221> NAME/KEY: CDS
<222> LOCATION: (1)..(45)

<400> SEQUENCE: 68 tgg tac cag cag aaa cca gga cag cct cct aag ctg ctc att tac        45
Trp Tyr Gln Gln Lys Pro Gly Gln Pro Pro Lys Leu Leu Ile Tyr
```

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

```
Trp Tyr Gln Gln Lys Pro Gly Gln Pro Pro Lys Leu Leu Ile Tyr
1               5                   10                  15
```

<210> SEQ ID NO 70
<211> LENGTH: 96
<212> TYPE: DNA
<213> ORGANISM: Artificial Sequence
<220> FEATURE:
<223> OTHER INFORMATION: AT14-012 FW3 light chain
<220> FEATURE:
<221> NAME/KEY: CDS
<222> LOCATION: (1)..(96)

<400> SEQUENCE: 70

```
ggg gtc cct gac cga ttc agt ggc agc ggg tct ggg aca gat ttc act    48
Gly Val Pro Asp Arg Phe Ser Gly Ser Gly Ser Gly Thr Asp Phe Thr
1               5                   10                  15 ctc acc atc agc agc ctg cag gct gaa gat gtg gca gtt tat tac tgt    96
Leu Thr Ile Ser Ser Leu Gln Ala Glu Asp Val Ala Val Tyr Tyr Cys
                20                  25                  30
```

<210> SEQ ID NO 71
<211> LENGTH: 32
<212> TYPE: PRT
<213> ORGANISM: Artificial Sequence
<220> FEATURE:
<223> OTHER INFORMATION: Synthetic Construct

<400> SEQUENCE: 71

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
                20                  25                  30
```

<210> SEQ ID NO 72
<211> LENGTH: 36
<212> TYPE: DNA
<213> ORGANISM: Artificial Sequence
<220> FEATURE:
<223> OTHER INFORMATION: AT14-012 FW4 light chain
<220> FEATURE:
<221> NAME/KEY: CDS
<222> LOCATION: (1)..(36)

<400> SEQUENCE: 72

```
tcc acc ttc ggc caa ggg aca cga ctg gag att aaa                    36
Ser Thr Phe Gly Gln Gly Thr Arg Leu Glu Ile Lys
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: Synthetic Construct

<400> SEQUENCE: 73

```
Ser Thr Phe Gly Gln Gly Thr Arg Leu Glu Ile Lys
1               5                   10
```

<210> SEQ ID NO 74
<211> LENGTH: 15
<212> TYPE: PRT
<213> ORGANISM: Artificial Sequence
<220> FEATURE:
<223> OTHER INFORMATION: m3 region

<400> SEQUENCE: 74

```
Cys Gly Leu Ala Gly Gly Val Glu Gln Phe Ile Ser Asp Ile Cys
1               5                   10                  15
```

<210> SEQ ID NO 75
<211> LENGTH: 15
<212> TYPE: PRT
<213> ORGANISM: Artificial Sequence
<220> FEATURE:
<223> OTHER INFORMATION: A14-012 epitope

<400> SEQUENCE: 75

```
Cys Pro Lys Lys Asp Val Leu Glu Thr Phe Thr Val Lys Ser Cys
1               5                   10                  15
```

<210> SEQ ID NO 76
<211> LENGTH: 206
<212> TYPE: PRT
<213> ORGANISM: Homo sapiens

<400> SEQUENCE: 76

```
Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
    50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Pro Gln Arg Glu Thr Leu Lys Ala Ile His Tyr Ala Leu
            115                 120                 125

Asn Cys Cys Gly Leu Ala Gly Gly Val Glu Gln Phe Ile Ser Asp Ile
        130                 135                 140

Cys Pro Lys Lys Asp Val Leu Glu Thr Phe Thr Val Lys Ser Cys Pro
145                 150                 155                 160

Asp Ala Ile Lys Glu Val Phe Asp Asn Lys Phe His Ile Ile Gly Ala
                165                 170                 175

Val Gly Ile Gly Ile Ala Val Val Met Ile Phe Gly Met Ile Phe Ser
            180                 185                 190

Met Ile Leu Cys Cys Ala Ile Arg Arg Asn Arg Glu Met Val
            195                 200                 205
```

<210> SEQ ID NO 77
<211> LENGTH: 206

<212> TYPE: PRT
<213> ORGANISM: Gorilla gorilla

<400> SEQUENCE: 77

```
Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
    50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Leu Gln Arg Glu Thr Leu Lys Ala Ile His Tyr Ala Leu
        115                 120                 125

Asn Cys Cys Gly Leu Ala Gly Val Glu Gln Phe Ile Ser Asp Ile
    130                 135                 140

Cys Pro Lys Lys Asp Val Leu Glu Thr Phe Thr Val Lys Ser Cys Pro
145                 150                 155                 160

Asp Ala Ile Lys Glu Val Phe Asp Asn Lys Phe His Ile Ile Gly Ala
                165                 170                 175

Val Gly Ile Gly Ile Ala Val Val Met Ile Phe Gly Met Ile Phe Ser
            180                 185                 190

Met Ile Leu Cys Cys Ala Ile Arg Arg Asn Arg Glu Met Val
        195                 200                 205
```

<210> SEQ ID NO 78
<211> LENGTH: 206
<212> TYPE: PRT
<213> ORGANISM: Pongo pygmaeus

<400> SEQUENCE: 78

```
Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
    50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Pro Gln Arg Glu Thr Leu Lys Ala Ile His Tyr Ala Leu
        115                 120                 125

Asn Cys Cys Gly Leu Val Gly Gly Val Glu Gln Phe Ile Ser Asp Ile
    130                 135                 140
```

```
Cys Pro Lys Lys Asp Gly Leu Glu Thr Phe Thr Val Lys Ser Cys Pro
145                 150                 155                 160

Asp Ala Ile Lys Glu Val Phe Asp Asn Lys Phe His Ile Ile Gly Ala
            165                 170                 175

Val Gly Ile Gly Ile Ala Val Val Met Ile Phe Gly Met Ile Phe Ser
            180                 185                 190

Met Ile Leu Cys Cys Ala Ile Arg Arg Asn Arg Glu Met Val
        195                 200                 205

<210> SEQ ID NO 79
<211> LENGTH: 206
<212> TYPE: PRT
<213> ORGANISM: Pan troglodytes

<400> SEQUENCE: 79

Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Pro Gln Arg Glu Thr Leu Lys Ala Ile His Tyr Ala Leu
            115                 120                 125

Asn Cys Cys Gly Leu Ala Gly Gly Val Glu Gln Phe Ile Ser Asp Ile
        130                 135                 140

Cys Pro Lys Lys Asp Gly Leu Glu Thr Phe Thr Val Lys Ser Cys Pro
145                 150                 155                 160

Asp Ala Ile Lys Glu Val Phe Asp Asn Lys Phe His Ile Ile Gly Ala
            165                 170                 175

Val Gly Ile Gly Ile Ala Val Val Met Ile Phe Gly Met Ile Phe Ser
            180                 185                 190

Met Ile Leu Cys Cys Ala Ile Arg Arg Asn Arg Glu Met Val
        195                 200                 205

<210> SEQ ID NO 80
<211> LENGTH: 206
<212> TYPE: PRT
<213> ORGANISM: Macaca

<400> SEQUENCE: 80

Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
50                  55                  60
```

```
Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Pro Gln Arg Glu Thr Leu Lys Ala Ile His Tyr Ala Leu
            115                 120                 125

Asp Cys Cys Gly Leu Ala Gly Gly Val Glu Gln Phe Ile Ser Asp Ile
            130                 135                 140

Cys Pro Lys Lys Asp Val Leu Glu Thr Leu Thr Ile Lys Ser Cys Pro
145                 150                 155                 160

Asp Ala Ile Lys Glu Val Phe Asp Asn Lys Phe His Ile Ile Gly Ala
                165                 170                 175

Val Gly Ile Gly Ile Ala Val Val Met Ile Phe Gly Met Ile Phe Ser
                180                 185                 190

Met Ile Leu Cys Cys Ala Ile Arg Arg Asn Arg Glu Met Val
            195                 200                 205
```

<210> SEQ ID NO 81
<211> LENGTH: 206
<212> TYPE: PRT
<213> ORGANISM: Papio hamadryas

<400> SEQUENCE: 81

```
Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn Asn Ser
                20                  25                  30

Ser Phe Tyr Thr Gly Val Tyr Ile Leu Ile Gly Ala Gly Ala Leu Met
            35                  40                  45

Met Leu Val Gly Phe Leu Gly Cys Cys Gly Ala Val Gln Glu Ser Gln
50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Thr
            100                 105                 110

Lys Asp Glu Pro Gln Arg Glu Thr Leu Lys Ala Ile His Tyr Ala Leu
            115                 120                 125

Asp Cys Cys Gly Leu Ala Gly Ala Val Glu Gln Phe Ile Ser Asp Ile
            130                 135                 140

Cys Pro Lys Lys Asp Val Leu Glu Thr Phe Thr Ile Lys Pro Cys Pro
145                 150                 155                 160

Ala Ala Ile Lys Glu Val Phe Asp Asn Lys Phe His Ile Ile Gly Ala
                165                 170                 175

Val Gly Ile Gly Ile Ala Val Val Met Ile Phe Gly Met Ile Phe Ser
                180                 185                 190

Met Ile Leu Cys Cys Ala Ile Arg Arg Asn Arg Glu Met Val
            195                 200                 205
```

<210> SEQ ID NO 82
<211> LENGTH: 206
<212> TYPE: PRT
<213> ORGANISM: Oryctolagus cuniculus

<400> SEQUENCE: 82

```
Leu Ala Gly Ile Ala Val Leu Ala Ile Gly Leu Trp Leu Arg Phe Asp
1               5                   10                  15

Ser Gln Thr Lys Ser Ile Phe Glu Gln Asp Lys Asn Asn Asn Asn Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
50                  55                  60

Cys Met Leu Gly Leu Phe Phe Gly Phe Leu Leu Val Ile Phe Ala Ile
65                  70                  75                  80

Glu Ile Ala Ala Ala Ile Trp Gly Tyr Ser His Lys Asp Glu Val Ile
                85                  90                  95

Lys Glu Val Gln Glu Phe Tyr Lys Asp Thr Tyr Asn Lys Leu Lys Asn
            100                 105                 110

Lys Asp Glu Pro Gln Arg Glu Thr Leu Lys Ala Ile His Tyr Ala Leu
        115                 120                 125

Asp Cys Cys Gly Met Ala Gly Val Glu Gln Phe Ile Ser Asp Ile
130                 135                 140

Cys Pro Lys Lys Asp Ile Leu Glu Ser Ile Gln Val Lys Ser Cys Pro
145                 150                 155                 160

Glu Ala Ile Lys Glu Val Phe Asp Asn Lys Phe His Val Ile Gly Ala
                165                 170                 175

Val Gly Ile Gly Ile Ala Val Val Met Ile Phe Gly Met Ile Phe Ser
            180                 185                 190

Met Ile Leu Cys Cys Ala Ile Arg Arg Ser Arg Glu Met Val
        195                 200                 205
```

<210> SEQ ID NO 83
<211> LENGTH: 206
<212> TYPE: PRT
<213> ORGANISM: Mus musculus

<400> SEQUENCE: 83

```
Leu Ala Gly Ile Ala Val Leu Ala Ile Gly Leu Trp Leu Arg Phe Asp
1               5                   10                  15

Ser Gln Thr Lys Ser Ile Phe Glu Gln Glu Thr Asn Asn Asn His Ser
            20                  25                  30

Ser Phe Tyr Thr Gly Val Tyr Ile Leu Ile Gly Ala Gly Ala Leu Met
        35                  40                  45

Met Leu Val Gly Phe Leu Gly Cys Cys Gly Ala Val Gln Glu Ser Gln
50                  55                  60

Cys Met Leu Gly Leu Phe Phe Gly Phe Leu Leu Val Ile Phe Ala Ile
65                  70                  75                  80

Glu Ile Ala Ala Ala Val Trp Gly Tyr Thr His Lys Asp Glu Val Ile
                85                  90                  95

Lys Glu Leu Gln Glu Phe Tyr Lys Asp Thr Tyr Gln Lys Leu Arg Ser
            100                 105                 110

Lys Asp Glu Pro Gln Arg Glu Thr Leu Lys Ala Ile His Met Ala Leu
        115                 120                 125

Asp Cys Cys Gly Ile Ala Gly Pro Leu Glu Gln Phe Ile Ser Asp Thr
130                 135                 140

Cys Pro Lys Lys Gln Leu Leu Glu Ser Phe Gln Val Lys Pro Cys Pro
145                 150                 155                 160
```

```
Glu Ala Ile Ser Glu Val Phe Asn Asn Lys Phe His Ile Ile Gly Ala
            165                 170                 175

Val Gly Ile Gly Ile Ala Val Val Met Ile Phe Gly Met Ile Phe Ser
            180                 185                 190

Met Ile Leu Cys Cys Ala Ile Arg Arg Ser Arg Glu Met Val
            195                 200                 205

<210> SEQ ID NO 84
<211> LENGTH: 120
<212> TYPE: PRT
<213> ORGANISM: Artificial Sequence
<220> FEATURE:
<223> OTHER INFORMATION: H40Y

<400> SEQUENCE: 84

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Tyr Pro Tyr Phe Asp Tyr Trp Gly Gln
            100                 105                 110

Gly Ile Leu Val Thr Val Ser Ser
            115                 120

<210> SEQ ID NO 85
<211> LENGTH: 120
<212> TYPE: PRT
<213> ORGANISM: Artificial Sequence
<220> FEATURE:
<223> OTHER INFORMATION: Y112F

<400> SEQUENCE: 85

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
            115                 120
```

```
<210> SEQ ID NO 86
<211> LENGTH: 120
<212> TYPE: PRT
<213> ORGANISM: Artificial Sequence
<220> FEATURE:
<223> OTHER INFORMATION: H40Y-Y112F

<400> SEQUENCE: 86
```

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Phe Pro Tyr Phe Asp Tyr Trp Gly Gln
            100                 105                 110

Gly Ile Leu Val Thr Val Ser Ser
        115                 120

```
<210> SEQ ID NO 87
<211> LENGTH: 120
<212> TYPE: PRT
<213> ORGANISM: Artificial Sequence
<220> FEATURE:
<223> OTHER INFORMATION: D116H

<400> SEQUENCE: 87
```

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Tyr Pro Tyr Phe His Tyr Trp Gly Gln
            100                 105                 110

Gly Ile Leu Val Thr Val Ser Ser
        115                 120

```
<210> SEQ ID NO 88
<211> LENGTH: 120
<212> TYPE: PRT
<213> ORGANISM: Artificial Sequence
<220> FEATURE:
<223> OTHER INFORMATION: T29N

<400> SEQUENCE: 88
```

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
 50                  55                  60

Lys Gly Arg Phe Thr Ile Ser Arg Asp Asn Ala Lys Asn Ser Leu Tyr
65                   70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Tyr Pro Tyr Phe Asp Tyr Trp Gly Gln
            100                 105                 110

Gly Ile Leu Val Thr Val Ser Ser
            115                 120

<210> SEQ ID NO 89
<211> LENGTH: 120
<212> TYPE: PRT
<213> ORGANISM: Artificial Sequence
<220> FEATURE:
<223> OTHER INFORMATION: D116H-T29N

<400> SEQUENCE: 89

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
 50                  55                  60

Lys Gly Arg Phe Thr Ile Ser Arg Asp Asn Ala Lys Asn Ser Leu Tyr
65                   70                  75                  80

Leu Gln Leu Asn Ser Leu Arg Ala Glu Asp Thr Ala Phe Tyr Tyr Cys
                85                  90                  95

Ala Lys Ala Val Ser Gly Tyr Tyr Pro Tyr Phe His Tyr Trp Gly Gln
            100                 105                 110

Gly Ile Leu Val Thr Val Ser Ser
            115                 120

<210> SEQ ID NO 90
<211> LENGTH: 120
<212> TYPE: PRT
<213> ORGANISM: Artificial Sequence
<220> FEATURE:
<223> OTHER INFORMATION: H40Y-Y112F-D116H-T29N

<400> SEQUENCE: 90

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Asn Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
 50                  55                  60

Lys Gly Arg Phe Thr Ile Ser Arg Asp Asn Ala Lys Asn Ser Leu Tyr

```
                65                  70                  75                  80
Leu Gln Leu Asn Ser Leu Arg Ala Glu Asp Thr Ala Phe Tyr Tyr Cys
                    85                  90                  95

Ala Lys Ala Val Ser Gly Tyr Phe Pro Tyr Phe His Tyr Trp Gly Gln
            100                 105                 110

Gly Ile Leu Val Thr Val Ser Ser
            115                 120

<210> SEQ ID NO 91
<211> LENGTH: 120
<212> TYPE: PRT
<213> ORGANISM: Artificial Sequence
<220> FEATURE:
<223> OTHER INFORMATION: G110D

<400> SEQUENCE: 91

Glu Val Gln Val Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Val Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Phe Tyr Tyr Cys
                85                  90                  95

Ala Lys Ala Val Ser Asp Tyr Tyr Pro Tyr Phe Asp Tyr Trp Gly Gln
            100                 105                 110

Gly Ile Leu Val Thr Val Ser Ser
            115                 120

<210> SEQ ID NO 92
<211> LENGTH: 14
<212> TYPE: PRT
<213> ORGANISM: Artificial Sequence
<220> FEATURE:
<223> OTHER INFORMATION: variant IgG

<400> SEQUENCE: 92

Pro Arg Tyr Leu Thr Val Ser Asn Met Lys Gln Ile Arg Phe
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Ig variant

<400> SEQUENCE: 93

Pro Arg Tyr Val Thr Val Ser Asn Met Lys Gln Ile Arg Phe
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Ig variant
```

```
<400> SEQUENCE: 94

Pro Arg Phe Leu Thr Val Ser Asn Met Lys Gln Ile Arg Phe
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Ig variant

<400> SEQUENCE: 95

Pro Arg Tyr Leu Thr Val Ser Lys Met Lys Gln Ile Arg Phe
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Ig variant

<400> SEQUENCE: 96

Pro Arg Tyr Leu Thr Val Asn Asn Met Lys Gln Ile Arg Phe
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Ig variant

<400> SEQUENCE: 97

Pro Arg Tyr Leu Thr Val Ser Asn Met Lys Glu Ile Arg Phe
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Ig variant

<400> SEQUENCE: 98

Pro Arg Tyr Leu Thr Val Ser Asn Val Arg Glu Val Arg Phe
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Ig variant

<400> SEQUENCE: 99

Leu Arg Tyr Leu Thr Val Asn Asn Met Lys Gln Ile Arg Tyr
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Ig variant

<400> SEQUENCE: 100
```

```
Leu Arg Tyr Leu Thr Val Asn Lys Met Lys Gln Ile Arg Tyr
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Ig variant

<400> SEQUENCE: 101

Leu Arg Tyr Leu Ala Val Asn Asn Met Lys Gln Ile Arg Tyr
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Ig variant

<400> SEQUENCE: 102

Pro Arg Tyr Leu Thr Met Ser Lys Val Lys Gln Ile His Tyr
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Ig variant

<400> SEQUENCE: 103

Pro Trp Tyr Leu Thr Met Ser Lys Val Lys Gln Ile His Tyr
1               5                   10
```

THERAPEUTIC ANTI-CD9 ANTIBODY

The invention relates to the fields of biology, immunology and medicine.

Melanoma is caused by malignant melanocytes. It is primarily caused by ultraviolet light exposure. Out of all different types of skin cancer malignant melanoma has the highest rate of mortality. It is estimated that world wide around 55,000 people have died from metastatic melanoma in 2012, a number which is steadily increasing every year. If spread has not yet occurred, most patients are cured by removing the melanoma. Patients with spread melanoma are treated with chemotherapy, radiation therapy and/or recently developed immunotherapies such as adoptive T-cell therapy or so called checkpoint inhibitor antibodies. These new immunotherapies clearly show that the immune system is able to recognize and attack the melanoma tumor cells. However, the response rate to such therapies is less than 50% and 5-years survival rates are around 30%. Therefore, additional treatment options are highly needed. The present invention provides means and methods for counteracting, preventing and/or detecting melanoma and other diseases.

Some embodiments of the present invention provide a patient-derived, human antibody that is specific for CD9. Importantly, this antibody is derived from a late stage IV melanoma patient who was in complete remission after immunotherapy and is still alive and well 10 years after treatment. The human antibody, designated AT14-012, is able to bind CD9-containing cells like melanoma, pancreas carcinoma, esophagus carcinoma and colon carcinoma cells.

The transmembrane protein CD9, also referred to as, amongst other things, MRP-1, MIC3, DRAP-27 and TSPAN-29, is a tetraspanin with a molecular weight of about 23-27 kDa. It is ubiquitously present on the surface of many kinds of cells, including melanocytes, endothelial cells, certain types of nervous cells, muscoskeletal cells and certain types of immune cells. CD9 is also present on platelets. CD9 has four transmembrane domains, a small intracellular loop and two extracellular loops, which are referred to as the EC1 domain and the EC2 domain (FIG. 1). CD9 interacts with numerous other proteins, such as the most important integrins (Beta1 integrin), EWI proteins (EWI-2 and EWI-F), CD81, CD63 and EGFR. CD9 plays amongst other things a role in cell adhesion, proliferation and migration, including tumor proliferation and metastasis. In view of the presence of CD9 on the cell surface of many kinds of cells, including platelets, adverse side effects were feared for currently known CD9-specific antibodies. Indeed, Kawakatsu et al. 1993 describes that platelet aggregation effects of anti-CD9 antibodies led to lethal thrombosis in a primate model. Monkeys injected with the anti-CD9 antibodies died within 5 minutes due to pulmonary thrombosis. This is confirmed in the examples of the present application: the known anti-CD9 antibody ALB6 induces strong aggregation of platelets (Example 3). Although multiple CD9 antibodies have been developed and described, due to this severe side-effect, none of these known CD9 antibodies has proceeded to clinical trials so far.

Interestingly however, as shown in the Examples, antibody AT14-012 has a higher binding affinity for melanoma cells as compared to primary melanocytes. In addition, AT14-012 has a higher binding activity for colon carcinoma as compared to primary colon epithelial cells. Moreover, AT14-012 binds several primary AML blasts and multiple myeloma cell lines, whereas it exhibits only a weak reactivity against primary human tonsil cells. The Examples show that antibody AT14-012 preferentially binds to clustered CD9 over binding to monomeric CD9. It is known that formation of homoclusters of CD9 is favored by palmitoylation of CD9 and that levels of CD9 homoclusters are elevated on primary tumor cells and in particular on metastatic tumor cells (Yang et al., 2006). Hence, the preferred binding of AT14-012 may contribute to the finding that antibody AT14-012 has a higher binding affinity for several tumor cells over CD9-expressing non-tumor cells. In addition, multimerization of AT14-012 as a result of binding to clustered CD9 may trigger a mechanism specifically inhibiting tumor growth or disease spreading.

Importantly, whereas currently known CD9-specific antibodies such as for instance ALB6 have the severe side-effect of platelet aggregation as described above, hence involving the risk of thrombosis as a side effect, the present inventors have demonstrated that antibody AT14-012, and several variants of AT14-012 that bind the same unique epitope, do not induce any detectable platelet aggregation in vitro. Although AT14-012 and such variants bind and even slightly activate platelets, aggregation was not observed. This provides the important advantage of AT14-012 and these variants over currently known CD9-specific antibodies that the risk of thrombosis is significantly reduced. Indeed, the melanoma patient from whom AT14-012 has been derived did not show any sign of thrombosis. In fact, this melanoma patient did not exhibit any sign of adverse side effects resulting from his immunotherapy treatment not even vitiligo, which is a skin disease resulting in the loss of pigment.

In view of the above-mentioned characteristics, antibody AT14-012, or a functional part or functional equivalent thereof or variants thereof having the same binding specificity, is an attractive choice for counteracting, preventing and/or detecting disorders associated with CD9-expressing cells, like melanoma. The therapeutic usefulness is already apparent from the fact that this antibody was isolated from a melanoma patient who went into complete remission and is a long-time melanoma survivor. Moreover, as shown in the Examples, AT14-012 binds melanoma, pancreas carcinoma, esophagus carcinoma and colon carcinoma cells, several AML blasts and some multiple myeloma cell lines. Moreover, the Examples have shown that AT14-012 significantly counteracts tumor growth and outgrowth of metastases in an in vivo melanoma mouse model. Antibody AT14-012, as well as functional parts and functional equivalents thereof with the same binding specificity, and other binding compounds that are specific for the same epitope as AT14-012 and/or compete with AT14-012 for binding to the same epitope of CD9, are therefore particularly suitable for detecting and/or counteracting diseases that are associated with CD9-containing cells, like for instance CD9-positive tumors, osteoporosis, arthritis, lung inflammation, COPD, colitis, Alzheimer's disease and disorders associated with innate lymphoid cells. Moreover, since CD9 is also expressed on extracellular vesicles, these vesicles are also interesting targets of antibody AT14-012 or the above-mentioned binding compounds.

As shown in the Examples, antibody AT14-012 binds a CD9 epitope that resides in the m4 region. This epitope comprises at least CD9 amino acids corresponding to K169, D171, V172, L173 and F176 of the CD9 sequence as depicted in FIG. 2. In particular, it is demonstrated that AT14-012 binds to amino acids K169, D171, V172, L173 and F176 of the CD9 sequence as depicted in FIG. 2.

CD9-specific antibodies are known in the art. However, these antibodies are often not human and recognize a different epitope. Human antibodies described are derived from artificial libraries where immunoglobulin heavy and light chains are randomly paired. In contrast AT14-012 was derived from a human patient with naturally paired heavy and light chains. For instance, international patent application WO 2009/157623 describes antibody 10E4, obtained from a human phage display library, that binds amino acid positions 186-191 of the CD9 sequence as depicted in FIG. 2.

WO 2014/145940 describes murine CD9-specific monoclonal antibodies Z9.1 and Z9.2 which show binding to amino acid positions 112-191 of the CD9 sequence as depicted in FIG. 2 and WO 2013/099925 describes murine antibody CD9-12A12, which binds amino acid positions 112-194 of the CD9 sequence as depicted in FIG. 2.

WO 2004/007685 concerns antibody mAb7, which binds the amino acid sequence PKKDV (SEQ ID NO: 17), which is present on amino acid positions 167-171 of the CD9 sequence as depicted in FIG. 2.

WO 95/033823 concerns murine monoclonal antibody ES5.2D8 which binds the CD9 sequence GLWLRFD (SEQ ID NO: 18). This sequence is located between amino acid positions 31 and 37 of the CD9 sequence as depicted in FIG. 2.

European patent EP 0508417 claims murine antibodies against amino acid sequences of CD9, which sequences are selected from amino acid positions 35-60, 113-142, 131-166 and 163-191 of the CD9 sequence as depicted in FIG. 2.

Other CD9-specific antibodies known in the art are murine antibodies ALB6 and HI9a. As shown in the Examples, these murine antibodies also bind a different epitope as compared to AT14-012. For instance, AT14-012 significantly binds CD9 amino acids K169, D171, V172, L173 and F176, as depicted in FIG. 2, whereas ALB6 does not significantly bind these amino acid residues. Moreover, as shown in the Examples, antibody AT14-012 is able to bind a CD9 mutant (mutant m1) wherein residues 112-134 of CD9 (numbering as depicted in FIG. 2) were replaced by the corresponding region of CD81, whereas antibodies ALB6 and HI9a are not able to bind this mutant. Furthermore, HI9a is able to bind mutant m4 (wherein residues 168-180 of CD9 were replaced by the corresponding region of CD81), whereas AT14-012 does not bind this mutant m4. Finally, the Examples show that antibody ALB6 binds amino acids Q161 in m3 and F176 in m4. Hence, ALB6 and HI9a bind a different epitope as compared to AT14-012.

The Examples further show that AT14-012 reactivity is restricted to primates, binding to mouse and rabbit platelets expressing CD9 was not observed. This confirms the uniqueness of the epitope in CD9 that is bound by AT14-012 as compared to that of e.g. murine antibodies ALB6 and HI9a, which do bind mouse CD9.

In conclusion, a novel human CD9-specific antibody is provided by the present invention, which is specific for a novel CD9 epitope.

Some embodiments of the present invention therefore provide an isolated, synthetic or recombinant antibody, or a functional part or a functional equivalent thereof, that is specific for (i.e. able to specifically bind) at least 6 amino acids located within amino acid positions 154-181 of the CD9 sequence as depicted in FIG. 2.

Preferably, said antibody or functional part or functional equivalent is specific for at least 6 amino acids located within amino acid positions 168-181 of the CD9 sequence as depicted in FIG. 2. Also provided is an isolated, synthetic or recombinant antibody, or a functional part or a functional equivalent thereof, that is specific for (i.e. able to specifically bind) at least 5 amino acids located within amino acid positions 168-181 of the CD9 sequence as depicted in FIG. 2.

Some embodiments provide an isolated, synthetic or recombinant antibody, or a functional part or a functional equivalent thereof, that is specific for an epitope of CD9, wherein said epitope comprises at least one amino acid residue selected from the group consisting of amino acids K169, D171, V172, L173 and T175 of the CD9 sequence as depicted in FIG. 2. Some embodiments provide an isolated, synthetic or recombinant antibody, or a functional part or a functional equivalent thereof, that is specific for an epitope of CD9, wherein said epitope comprises at least one amino acid residue selected from the group consisting of amino acids K169, D171, V172 and L173 of the CD9 sequence as depicted in FIG. 2. Said antibody or functional part or functional equivalent according to the invention is preferably also able to specifically bind amino acid F176 of the CD9 sequence as depicted in FIG. 2. Some embodiments provide an antibody or functional part or functional equivalent that is specific for an epitope of CD9, wherein said epitope comprises at least two amino acid residues selected from the group consisting of amino acids K169, D171, V172, L173, T175 and F176 of the CD9 sequence as depicted in FIG. 2. In some embodiments, said antibody or functional part or functional equivalent is specific for an epitope of CD9, wherein said epitope comprises at least three, or at least four or at least five, amino acid residues selected from the group consisting of amino acids K169, D171, V172, L173, T175 and F176 of the CD9 sequence as depicted in FIG. 2. Said epitope preferably comprises at least three, four or five amino acid residues selected from the group consisting of amino acids K169, D171, V172, L173 and F176 of the CD9 sequence as depicted in FIG. 2. Preferred embodiments provide an isolated, synthetic or recombinant antibody, or a functional part or a functional equivalent thereof according to the invention, that is specific for an epitope of CD9 comprising amino acids corresponding to K169, D171, V172, L173 and F176 of the CD9 sequence as depicted in FIG. 2. Some embodiments provide an isolated, synthetic or recombinant antibody, or a functional part or a functional equivalent thereof according to the invention, that is specific for an epitope of CD9 comprising amino acids corresponding to K169, D171, V172, L173 and F176 of the CD9 sequence as depicted in FIG. 2.

As used herein, the term "CD9 sequence as depicted in FIG. 2" means the amino acid sequence of the human CD9 protein as depicted in FIG. 2 (UniProt number P21926; Genbank accession number NP-001760).

As used herein, the expressions "located within CD9 amino acid positions X and Y as depicted in FIG. 2" and "located within amino acid positions X and Y of the CD9 sequence as depicted in FIG. 2" encompass sequences that are located between the recited positions and that include the amino acid(s) of position X and/or Y. In addition, the terms embrace sequences that are located between the recited positions and that do not contain the amino acid(s) of positions X and/or Y.

The term "antibody" as used herein, refers to an immunoglobulin protein comprising at least a heavy chain variable region (VH), paired with a light chain variable region (VL), that is specific for a target epitope.

A "functional part of an antibody" is defined herein as a part that has at least one shared property as said antibody in kind, not necessarily in amount. Said functional part is capable of binding the same antigen as said antibody, albeit not necessarily to the same extent. In one embodiment, a functional part of an antibody comprises at least a heavy chain variable domain (VH). Non-limiting examples of a functional part of an antibody are a single domain antibody, a single chain antibody, a nanobody, an unibody, a single chain variable fragment (scFv), a Fd fragment, a Fab fragment and a F(ab')$_2$ fragment.

A "functional equivalent of an antibody" is defined herein as an artificial binding compound, comprising at least one CDR sequence of an antibody, preferably a heavy chain CDR3 sequence. Said functional equivalent preferably comprises the heavy chain CDR3 sequence of an antibody, as well as the light chain CDR3 sequence of said antibody. More preferably, said functional equivalent comprises the heavy chain CDR1, CDR2 and CDR3 sequences of an antibody, as well as the light chain CDR1, CDR2 and CDR3 sequences of said antibody. A functional equivalent of an antibody is for instance produced by altering an antibody such that at least an antigen-binding property of the resulting compound is essentially the same in kind, not necessarily in amount. This is done in many ways, for instance through conservative amino acid substitution, whereby an amino acid residue is substituted by another residue with generally similar properties (size, hydrophobicity, etc.), such that the overall functioning of the antibody is essentially not affected.

As is well known by the skilled person, a heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain is often, but not always, together with the variable domain of the heavy chain involved in antigen binding.

Complementary-determining regions (CDRs) are the hypervariable regions present in heavy chain variable domains and light chain variable domains. In case of whole antibodies, the CDRs 1-3 of a heavy chain and the CDRs 1-3 of the connected light chain together form the antigen-binding site.

As used herein, the term "an antibody or functional part or functional equivalent according to the invention" is also referred to as "a binding compound according to the invention".

The terms "specific for", "able to specifically bind" and "capable of specifically binding" are used herein interchangeably and refer to the interaction between an antibody, or functional part or functional equivalent thereof, and its epitope. This means that said antibody, or functional part or functional equivalent thereof, preferentially binds to said epitope over other antigens or amino acid sequences. Thus, although the antibody, functional part or equivalent may non-specifically bind to other antigens or amino acid sequences, the binding affinity of said antibody or functional part or functional equivalent for its epitope is significantly higher than the non-specific binding affinity of said antibody or functional part or functional equivalent for other antigens or amino acid sequences.

An antibody or functional part or functional equivalent according to the invention that is able to bind a particular epitope of CD9 can also be specific for other, non-CD9 cells if said epitope of CD9 also happens to be present in another protein. In that case an antibody referred to herein as being specific for CD9 is also specific for such other protein comprising the same epitope.

"Binding affinity" refers to the strength of the total sum of the noncovalent interactions between a single binding site of an antibody or functional part or functional equivalent and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the equilibrium dissociation constant ($K_D$), which is calculated as the $k_a$ to $k_d$ ratio, see, e.g., Chen, Y., et al., (1999) *J. Mol Biol* 293:865-881. Affinity can be measured by common methods known in the art, such as for instance a Surface Plasmon Resonance (SPR) assay such as BiaCore (GE Healthcare) or IBIS-iSPR instrument at IBIS Technologies BV (Hengelo, the Netherlands) or solution phase assays, such as Kinexa.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. Methods and computer programs for the alignment are well known in the art, for example "Align 2".

An antibody or functional part or functional equivalent according to the invention is preferably able to bind melanoma cells, colon carcinoma cells, pancreas carcinoma cells and esophagus carcinoma cells. Such binding compound is suitable for counteracting various kinds of cancers and has, therefore, a broad applicability. Specificity for at least melanoma is preferred.

In some embodiments, an antibody or functional part or functional equivalent according to the invention is a human antibody or a functional part or functional equivalent thereof. The presence of human amino acid sequences diminishes the chance of adverse side effects during therapeutic use in human patients, as opposed to murine or humanized antibodies, wherein the non-human CDR or variable region sequences typically result in an anti-murine immune response in human recipients.

In one particularly preferred embodiment, an antibody or functional part or functional equivalent according to the invention is provided wherein said antibody is of the IgG isotype, preferably IgG1 or IgG3. This is beneficial for medical applications in humans.

A preferred antibody according to the present invention is antibody AT14-012. This antibody is preferred because it binds at least melanoma, pancreas carcinoma, esophagus carcinoma and colon carcinoma cells, several AML blasts and some multiple myeloma cell lines. Moreover, it has been demonstrated that AT14-012 counteracts metastases in vivo. This antibody is, therefore, particularly suitable for counteracting disorders associated with CD9-expressing cells, such as for instance a cancer involving CD9-positive tumor cells, like melanoma. Interestingly, AT14-012 is of the IgG3 isotype and belongs to the VH3-09 family. The heavy chain CDR1, CDR2 and CDR3 sequences, and the light chain CDR1, CDR2 and CDR3 sequences of antibody AT14-012 are depicted in Table 1 and FIG. 3.

As used herein, the term "AT14-012" encompasses all antibodies and functional parts and functional equivalents thereof having at least the heavy chain and light chain CDR1-3 sequences, preferably at least the heavy chain and light chain variable region sequences, of antibody AT14-012. Such antibodies and functional parts and functional equivalents for instance comprise isolated and/or purified antibodies, recombinant antibodies, and/or antibodies obtained using an AT14-012 nucleic acid sequence that has been codon optimized for a producer host cell such as for instance a CHO cell.

Based on the AT14-012 sequences depicted in Table 1 and FIG. 3, it is possible to produce an antibody or functional part or functional equivalent thereof comprising at least one CDR sequence of AT14-012, which is specific for CD9. Provided is therefore an isolated, recombinant and/or synthetic antibody or a functional part or functional equivalent thereof comprising at least one CDR sequence of antibody AT14-012, as depicted in Table 1 and FIG. 3. Said at least one CDR sequence preferably at least comprises a CDR3 sequence. Further provided is therefore an isolated, synthetic or recombinant antibody, or a functional part or a functional equivalent thereof, that comprises at least a heavy chain CDR3 sequence having the sequence AVSGYYPYFDY (SEQ ID NO: 6) and a light chain CDR3 sequence having the sequence QQYYTTP (SEQ ID NO: 12). Preferably, binding compounds are provided that comprise at least two CDRs, more preferably at least three CDRs, of antibody AT14-012. In some embodiments, at least two or three CDRs of the heavy and light chains of antibody AT14-012 are jointly present in one binding compound according to the invention. Preferably, a binding compound according to the invention comprises all three heavy chain CDRs and all three light chain CDRs of antibody AT14-012.

Optionally, at least one of said CDR sequences is optimized, thereby generating a variant binding compound, preferably in order to improve binding efficacy, selectivity, and/or stability. This is for instance done by mutagenesis procedures where after the stability and/or binding efficacy of the resulting compounds are preferably tested and an improved CD9-specific binding compound is selected. A skilled person is well capable of generating variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. Preferably, an antibody or functional part or functional equivalent is provided comprising a CDR sequence which is at least 80% identical to a CDR sequence of antibody AT14-012, so that the favorable CD9-binding characteristic is maintained or even improved. Variant binding compounds comprising an amino acid sequence which is at least 80% identical to a CDR sequence of antibody AT14-012 are therefore also within the scope of the present invention. Preferably, said binding compounds comprise heavy chain and light chain CDR 1-3 sequences which are at least 80% identical to the heavy and light chain CDR 1-3 sequences of antibody AT14-012. Preferably, the CDR sequences of such variants differ in no more than three, preferably in no more than two, preferably in no more than one amino acid from the original AT14-012 CDR sequences.

Besides optimizing CDR sequences in order to improve binding efficacy or stability, at least one sequence in at least one of the framework regions can be optimized. This is preferably done in order to improve binding efficacy or stability. Framework sequences are for instance optimized by mutating a nucleic acid molecule encoding such framework sequence where after the characteristics of the resulting binding compound are preferably tested. This way, it is possible to obtain improved binding compounds. In a preferred embodiment, human germline sequences are used for framework regions in antibodies according to the invention. The use of human germline sequences minimizes the risk of immunogenicity of said antibodies, because these sequences are less likely to contain somatic alterations which are unique to individuals from which the framework regions are derived, and may cause an immunogenic response when applied to another human individual. Further provided is therefore a synthetic or recombinant antibody or functional part or functional equivalent according to the invention, comprising at least one mutation in a framework region, as compared to the framework region of AT14-012. Additionally, or alternatively, a synthetic or recombinant antibody or functional part or functional equivalent according to the invention is provided that comprises at least one mutation in a constant region, as compared to the constant region of antibody AT14-012. Such binding compound with at least one mutation as compared to AT14-012 does not occur in nature. Instead, it has been artificially produced. In one embodiment, the IgG3 Fc region of antibody AT14-012 is at least partly replaced by an IgG1 Fc region. This typically increases the stability and half life of the resulting immunoglobulin.

In some embodiments, a binding compound according to the present invention comprises a human variable region. In some embodiments, said binding compound comprises a human constant region and a human variable region. In some preferred embodiments, said binding compound is a human antibody. For therapeutic applications in humans, the use of human CD9-specific antibodies is advantageous over the use of non-human antibodies. The in vivo use of non-human antibodies for diagnosis and/or treatment of human diseases is hampered by a number of factors. In particular, the human body may recognize non-human antibodies as foreign, which will result in an immunogenic response against the non-human antibodies, resulting in adverse side effects and/or rapid clearance of the antibodies from the circulation. A human antibody diminishes the chance of side-effects when administered to a human individual and often results in a longer half-life in the circulation because of reduced clearance when compared to non-human antibodies.

In some embodiments, a binding compound according to the invention is a chimeric antibody. In such chimeric antibody, sequences of interest such as for instance an additional binding site of interest are provided to a binding compound according to the invention.

Binding compounds according to the invention are preferably monoclonal antibodies. A monoclonal antibody is an antibody consisting of a single molecular species. Monoclonal antibodies can be produced in large quantities by monoclonal antibody-producing cells or recombinant DNA technology.

Hence, variant binding compounds based on antibody AT14-012 can be generated, using techniques known in the art such as for instance mutagenesis. Typically, sequence variations between 80 and 99% are tolerated while maintaining antigen specificity. One embodiment therefore provides an isolated, synthetic or recombinant antibody or a functional part or a functional equivalent thereof, that comprises:
 a heavy chain CDR1 sequence that has at least 80% sequence identity with the sequence DYAMH (SEQ ID NO: 2); and
 a heavy chain CDR2 sequence that has at least 80% sequence identity with the sequence GISWNSGSIVY-ADSVKG (SEQ ID NO: 4); and a heavy chain CDR3 sequence that has at least 80% sequence identity with the sequence AVSGYYPYFDY (SEQ ID NO: 6); and a light chain CDR1 sequence that has at least 80% sequence identity with the sequence KSSQSVLYSSNNKNYLG (SEQ ID NO: 8); and a light chain CDR2 sequence that has at least 80% sequence identity with the sequence WASTRES (SEQ ID NO: 10); and a light chain CDR3 sequence that has at least 80% sequence identity with the sequence QQYYTTP (SEQ ID NO: 12). Said antibody or functional part or functional equivalent is preferably specific for an epitope of CD9 comprising at least one amino acid selected from the group consisting of K169, D171, V172 and L173 of the CD9 sequence as depicted in FIG. 2, more preferably specific for an epitope of CD9 comprising amino acids corresponding to K169, D171, V172, L173 and F176 of the CD9 sequence as depicted in FIG. 2.

Preferably, said sequence identity is at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%.

The CDR numbering and definition used herein is according to Kabat et al (1991), unless indicted otherwise. Correspondence between different numbering system, including the Kabat numbering, the EU numbering and the IMGT numbering, is well known to a person skilled in the art.

Some embodiments therefore provide an isolated, synthetic or recombinant antibody or a functional part or a functional equivalent thereof, that comprises:

a heavy chain CDR1 sequence that has at least 85%, preferably at least 90%, more preferably at least 95% sequence identity with the sequence DYAMH (SEQ ID NO: 2); and a heavy chain CDR2 sequence that has at least 85%, preferably at least 90%, more preferably at least 95% sequence identity with the sequence GISWNSGSIVYADSVKG (SEQ ID NO: 4); and a heavy chain CDR3 sequence that has at least 85%, preferably at least 90%, more preferably at least 95% sequence identity with the sequence AVSGYYPYFDY (SEQ ID NO: 6); and a light chain CDR1 sequence that has at least 85%, preferably at least 90%, more preferably at least 95% sequence identity with the sequence KSSQSVLYSSNNKNYLG (SEQ ID NO: 8); and a light chain CDR2 sequence that has at least 85%, preferably at least 90%, more preferably at least 95% sequence identity with the sequence WASTRES (SEQ ID NO: 10); and a light chain CDR3 sequence that has at least 85%, preferably at least 90%, more preferably at least 95% sequence identity with the sequence QQYYTTP (SEQ ID NO: 12). Said antibody or functional part or functional equivalent is preferably specific for an epitope of CD9 comprising at least one amino acid selected from the group consisting of K169, D171, V172 and L173 of the CD9 sequence as depicted in FIG. 2, more preferably specific for an epitope of CD9 comprising amino acids corresponding to K169, D171, V172, L173 and F176 of the CD9 sequence as depicted in FIG. 2.

Some embodiments provide an isolated, synthetic or recombinant antibody or a functional part or a functional equivalent thereof, that comprises:

a heavy chain CDR1 sequence that has at least 97% sequence identity with the sequence DYAMH (SEQ ID NO: 2); and a heavy chain CDR2 sequence that has at least 97% sequence identity with the sequence GISWNSGSIVYADSVKG (SEQ ID NO: 4); and a heavy chain CDR3 sequence that has at least 97% sequence identity with the sequence AVSGYYPYFDY (SEQ ID NO: 6); and a light chain CDR1 sequence that has at least 97% sequence identity with the sequence KSSQSVLYSSNNKNYLG (SEQ ID NO: 8); and a light chain CDR2 sequence that has at least 97% sequence identity with the sequence WASTRES (SEQ ID NO: 10); and a light chain CDR3 sequence that has at least 97% sequence identity with the sequence QQYYTTP (SEQ ID NO: 12). Said antibody or functional part or functional equivalent is preferably specific for an epitope of CD9 comprising at least one amino acid selected from the group consisting of K169, D171, V172 and L173 of the CD9 sequence as depicted in FIG. 2, more preferably specific for an epitope of CD9 comprising amino acids corresponding to K169, D171, V172, L173 and F176 of the CD9 sequence as depicted in FIG. 2.

In the Examples, it is shown that a mutation in heavy chain CDR1 and/or one or two mutations in CDR3 and/or a mutation in light chain CDR2 result in antibodies that bind the same epitope as antibody AT14-012 and that have a binding affinity that is equal to or higher than the binding affinity of AT14-012. Importantly, as further shown in the Examples, variants of antibody AT14-012 that have such mutations in heavy chain CDR1 and/or heavy chain CDR3 and/or light chain CDR2 also have the property that they do not aggregate platelets, even if the variants have a higher affinity for CD9 as compared to AT14-012. Hence, the Examples show that antibodies comprising heavy chain CDR1 and/or heavy chain CDR3 sequences that are at least 80% identical to the heavy chain CDR1, heavy chain CDR3 and light chain CDR2 sequences of antibody AT14-012 have the same new and unique properties, including specificity for a novel epitope of CD9 and absence of platelet aggregation, as antibody AT14-012. The affinity of antibody AT14-012 is not linked to the absence of platelet aggregation, but instead the crucial characteristic that is associated with the absence of platelet aggregation is the recognition of a unique epitope on CD9.

One embodiment therefore provides an isolated, synthetic or recombinant antibody or a functional part or a functional equivalent thereof, that is specific for an epitope of CD9 comprising at least one amino acid selected from the group consisting of K169, D171, V172 and L173 of the CD9 sequence as depicted in FIG. 2, and that comprises:

a heavy chain CDR1 sequence that has at least 80% sequence identity with the sequence DYAMH (SEQ ID NO: 2); and a heavy chain CDR2 sequence GISWNSGSIVYADSVKG (SEQ ID NO: 4); and a heavy chain CDR3 sequence that has at least 80% sequence identity with the sequence AVSGYYPYFDY (SEQ ID NO: 6); and a light chain CDR1 sequence KSSQSVLYSSNNKNYLG (SEQ ID NO: 8); and a light chain CDR2 sequence that has at least 85% sequence identity with the sequence WASTRES (SEQ ID NO: 10); and a light chain CDR3 sequence QQYYTTP (SEQ ID NO: 12). Said antibody or functional part or functional equivalent is preferably specific for an epitope of CD9 comprising amino acids corresponding to K169, D171, V172, L173 and F176 of the CD9 sequence as depicted in FIG. 2.

Methods to determine whether or not an antibody or functional part or functional equivalent thereof is specific for an epitope of CD9 comprising at least one amino acid selected from the group consisting of K169, D171, V172 and L173 of the CD9 sequence as depicted in FIG. 2 are well in the art and for instance described in the Examples herein. Indeed, the Examples show how binding to CD9, the epitope of CD9 that is bound by and antibody and the affinity of and antibody for CD9 can be determined.

The Examples also show that mutations in framework regions can be made without affecting the binding specificity and affinity and/or without effecting the degree of binding specificity and affinity. Indeed, the T29N mutation in heavy chain framework region 1, the L94P mutation in the light chain framework region 3 and the L120V mutation in light chain framework region 4 (IMGT numbering) did not have a major impact on binding of AT14-012 or on improved binding of variants of AT14-012 that show improved binding as compared to aT14-012.

As said before, typically at most 3 amino acid residues of a given CDR sequence may vary while retaining the same kind of binding activity (in kind, not necessarily in amount). Hence, a binding compound according to the invention preferably contains heavy chain and light chain CDR1-3 sequences wherein at most 3, preferably at most 2, more preferably at most 1 amino acid deviate(s) from the heavy and light chain CDR1-3 sequences of antibody AT14-012. In some embodiments, the heavy and light chain CDR1-3 sequences of a binding compound according to the invention are identical to the heavy and light chain CDR1-3 sequences of antibody AT14-012. Further provided is therefore an isolated, synthetic or recombinant antibody or a functional part or a functional equivalent thereof, that comprises:

a heavy chain CDR1 sequence having the sequence DYAMH (SEQ ID NO: 2); and a heavy chain CDR2 sequence having the sequence GISWNSGSIVYADSVKG (SEQ ID NO: 4); and a heavy chain CDR3 sequence having the sequence AVSGYYPYFDY (SEQ ID NO: 6); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

In some embodiments, the heavy and light chain CDR1-3 sequences of a binding compound according to the invention are identical to the heavy and light chain CDR1-3 sequences of variants of AT14-012, which have an affinity that is comparable to or higher than that of antibody AT14-012.

Further provided is therefore an isolated, synthetic or recombinant antibody or a functional part or a functional equivalent thereof, that comprises:

a heavy chain CDR1 sequence having the sequence DYAMY (SEQ ID NO: 21); and a heavy chain CDR2 sequence having the sequence GISWNSGSIVYADSVKG (SEQ ID NO: 4); and a heavy chain CDR3 sequence having the sequence AVSGYYPYFDY (SEQ ID NO: 6); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

Further provided is therefore an isolated, synthetic or recombinant antibody or a functional part or a functional equivalent thereof, that comprises:

a heavy chain CDR1 sequence having the sequence DYAMH (SEQ ID NO: 2); and a heavy chain CDR2 sequence having the sequence GISWNSGSIVYADSVKG (SEQ ID NO: 4); and a heavy chain CDR3 sequence having the sequence AVSGYFPYFDY (SEQ ID NO: 22); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

Further provided is therefore an isolated, synthetic or recombinant antibody or a functional part or a functional equivalent thereof, that comprises:

a heavy chain CDR1 sequence having the sequence DYAMH (SEQ ID NO: 2); and a heavy chain CDR2 sequence having the sequence GISWNSGSIVYADSVKG (SEQ ID NO: 4); and a heavy chain CDR3 sequence having the sequence AVSGYYPYFHY (SEQ ID NO: 23); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

Further provided is therefore an isolated, synthetic or recombinant antibody or a functional part or a functional equivalent thereof, that comprises:

a heavy chain CDR1 sequence having the sequence DYAMY (SEQ ID NO: 21); and a heavy chain CDR2 sequence having the sequence GISWNSGSIVYADSVKG (SEQ ID NO: 4); and a heavy chain CDR3 sequence having the sequence AVSGYFPYFDY (SEQ ID NO: 22); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

Further provided is therefore an isolated, synthetic or recombinant antibody or a functional part or a functional equivalent thereof, that comprises:

a heavy chain CDR1 sequence having the sequence DYAMY (SEQ ID NO: 21); and a heavy chain CDR2 sequence having the sequence GISWNSGSIVYADSVKG (SEQ ID NO: 4); and a heavy chain CDR3 sequence having the sequence AVSGYYPYFHY (SEQ ID NO: 23); and a light chain CDR1 sequence having the sequence KSSQSVLYSSNNKNYLG (SEQ ID NO: 8); and a light chain CDR2 sequence having the sequence WASTRES (SEQ ID NO: 10); and a light chain CDR3 sequence having the sequence QQYYTTP (SEQ ID NO: 12).

Further provided is therefore an isolated, synthetic or recombinant antibody or a functional part or a functional equivalent thereof, that comprises:
- a heavy chain CDR1 sequence having the sequence DYAMH (SEQ ID NO: 2); and
- a heavy chain CDR2 sequence having the sequence GISWNSGSIVYADSVKG (SEQ ID NO: 4); and
- a heavy chain CDR3 sequence having the sequence AVSGYFPYFHY (SEQ ID NO: 24); and
- a light chain CDR1 sequence having the sequence KSSQSVLYSSNNKNYLG (SEQ ID NO: 8); and
- a light chain CDR2 sequence having the sequence WASTRES (SEQ ID NO: 10); and
- a light chain CDR3 sequence having the sequence QQYYTTP (SEQ ID NO: 12).

Further provided is therefore an isolated, synthetic or recombinant antibody or a functional part or a functional equivalent thereof, that comprises:
- a heavy chain CDR1 sequence having the sequence DYAMY (SEQ ID NO: 21); and
- a heavy chain CDR2 sequence having the sequence GISWNSGSIVYADSVKG (SEQ ID NO: 4); and
- a heavy chain CDR3 sequence having the sequence AVSGYFPYFHY (SEQ ID NO: 24); and
- a light chain CDR1 sequence having the sequence KSSQSVLYSSNNKNYLG (SEQ ID NO: 8); and
- a light chain CDR2 sequence having the sequence WASTRES (SEQ ID NO: 10); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMY (SEQ ID NO: 21); and
- a heavy chain CDR2 sequence having the sequence GISWNSGSIVYADSVKG (SEQ ID NO: 4); and
- a heavy chain CDR3 sequence having the sequence AVSGYYPYFDY (SEQ ID NO: 6); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is therefore an isolated, synthetic or recombinant antibody or a functional part or a functional equivalent thereof, that comprises:
- a heavy chain CDR1 sequence having the sequence DYAMH (SEQ ID NO: 2); and
- a heavy chain CDR2 sequence having the sequence GISWNSGSIVYADSVKG (SEQ ID NO: 4); and
- a heavy chain CDR3 sequence having the sequence AVSGYFPYFDY (SEQ ID NO: 22); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMH (SEQ ID NO: 2); and
- a heavy chain CDR2 sequence having the sequence GISWNSGSIVYADSVKG (SEQ ID NO: 4); and
- a heavy chain CDR3 sequence having the sequence AVSGYYPYFHY (SEQ ID NO: 23); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMY (SEQ ID NO: 21); and
- a heavy chain CDR2 sequence having the sequence GISWNSGSIVYADSVKG (SEQ ID NO: 4); and
- a heavy chain CDR3 sequence having the sequence AVSGYFPYFDY (SEQ ID NO: 22); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMY (SEQ ID NO: 21); and
- a heavy chain CDR2 sequence having the sequence GISWNSGSIVYADSVKG (SEQ ID NO: 4); and
- a heavy chain CDR3 sequence having the sequence AVSGYYPYFHY (SEQ ID NO: 23); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMH (SEQ ID NO: 2); and
- a heavy chain CDR2 sequence having the sequence GISWNSGSIVYADSVKG (SEQ ID NO: 4); and
- a heavy chain CDR3 sequence having the sequence AVSGYFPYFHY (SEQ ID NO: 24); and
- a light chain CDR1 sequence having the sequence KSSQSVLYSSNNKNYLG (SEQ ID NO: 8); and
- a light chain CDR2 sequence having the sequence WASIRES (SEQ ID NO: 25); and
- a light chain CDR3 sequence having the sequence QQYYTTP (SEQ ID NO: 12).

Further provided is an isolated, synthetic or recombinant antibody or a functional part or a functional equivalent thereof, that comprises:
- a heavy chain CDR1 sequence having the sequence DYAMY (SEQ ID NO: 21); and
- a heavy chain CDR2 sequence having the sequence GISWNSGSIVYADSVKG (SEQ ID NO: 4); and
- a heavy chain CDR3 sequence having the sequence AVSGYFPYFHY (SEQ ID NO: 24); and
- a light chain CDR1 sequence having the sequence KSSQSVLYSSNNKNYLG (SEQ ID NO: 8); and a light chain CDR2 sequence having the sequence WASIRES (SEQ ID NO: 25); and a light chain CDR3 sequence having the sequence QQYYTTP (SEQ ID NO: 12).

A particularly preferred antibody comprises:
a heavy chain CDR1 sequence having the sequence DYAMY (SEQ ID NO: 21); and
a heavy chain CDR2 sequence having the sequence GISWNSGSIVYADSVKG (SEQ ID NO: 4); and
a heavy chain CDR3 sequence having the sequence AVSGYFPYFDY (SEQ ID NO: 22); and
a light chain CDR1 sequence having the sequence KSSQSVLYSSNNKNYLG (SEQ ID NO: 8); and
a light chain CDR2 sequence having the sequence WASTRES (SEQ ID NO: 10); and
a light chain CDR3 sequence having the sequence QQYYTTP (SEQ ID NO: 12). As demonstrated in the Examples, such antibody has a particularly high affinity (see FIG. 19B).

Preferably, a binding compound according to the invention comprises a variable heavy chain sequence and/or a variable light chain sequence of antibody AT14-012, or heavy and light chain variable sequences that are at least 80% identical. The heavy and light chain variable regions of antibody AT14-012 are also depicted in Table 1 and FIG. 3. Further provided is therefore an antibody or functional part or functional equivalent according to the invention, comprising a heavy chain variable region sequence having at least 80% sequence identity with the sequence EVQVVESGGGLVQPGRSLRLSCAASGFTFDDYAMHWVRQAPGKGLEWVSGISWNSG SIVYADSVKGRFTISRDNAKNSLYLQLNSLRAEDTAFYYCAKAVSGYYPYFDYWGQGI LVTVSS (SEQ ID NO: 14) and/or a light chain variable region sequence having at least 80% sequence identity with the sequence DIVMTQSPDSLSVSLGERATINCKSSQSVLYSSNNKNYLGWYQQKPGQPPKLLIYWAS TRESGVPDRFSGSGSGTDFTLTISSLQAEDVAVYYCQQYYTTPSTFGQGTRLEIK (SEQ ID NO: 16), or sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, or even 100% identical to the above mentioned heavy chain and/or light chain variable region sequences of AT14-012. Preferably, in the heavy chain and light chain variable regions the heavy chain CDR1, CDR2 and CDR3 sequences have at least 80% sequence identity with the sequences DYAMH (SEQ ID NO: 2) (CDR1), GISWNSGSIVYADSVKG (SEQ ID NO: 4) (CDR2) and AVSGYYPYFDY (SEQ ID NO: 6) (CDR3) and the light chain CDR1, CDR2 and CDR3 sequences have at least 80% sequence identity with the sequences KSSQSVLYSSNNKNYLG (SEQ ID NO: 8) (CDR1), WASTRES (SEQ ID NO: 10) (CDR2) and QQYYTTP (SEQ ID NO: 12) (CDR3). Said antibody or functional part or functional equivalent is preferably specific for an epitope of CD9 comprising at least one amino acid selected from the group consisting of K169, D171, V172 and L173 of the CD9 sequence as depicted in FIG. 2, more preferably specific for an epitope of CD9 comprising amino acids corresponding to K169, D171, V172, L173 and F176 of the CD9 sequence as depicted in FIG. 2. The higher the identity, the more closely a binding compound resembles antibody AT14-012. Preferably, a binding compound according to the invention comprises both the heavy chain variable region sequence and the light chain variable region sequence of antibody AT14-012, as depicted in Table 1 and FIG. 3, or heavy and light chain variable region sequences that are at least 80%, preferably at least 85%, or at least 86%, or at least 87%, or at least 88%, or at least 89%, or at least 90%, or 91%, or at least 92%, or at least 93%, or at least 94%, or at least 95%, or at least 96%, or at least 97%, or at least 98%, or at least 99%, identical thereto.

Particularly preferred is an antibody or functional part or functional equivalent thereof that is specific for an epitope of CD9 comprising at least one amino acid selected from the group consisting of K169, D171, V172 and L173 of the CD9 sequence as depicted in FIG. 2, preferably specific for an epitope of CD9 comprising amino acids corresponding to K169, D171, V172, L173 and F176 of the CD9 sequence as depicted in FIG. 2 and that comprises:

a heavy chain variable region sequence EVQVVESGGGLVQPGRSLRLSCAASGFTFDDYAMHWVRQAPGKGLEWVSGISWNSG SIVYADSVKGRFTISRDNAKNSLYLQLNSLRAEDTAFYYCAKAVSGYYPYFDYWGQGI LVTVSS (SEQ ID NO: 14), or EVQVVESGGGLVQPGRSLRLSCAASGFTFDDYAMYWVRQAPGKGLEWVSGISWNSG SIVYADSVKGRFTISRDNAKNSLYLQLNSLRAEDTAFYYCAKAVSGYFPYFDY WGQGI LVTVSS (SEQ ID NO: 26) or EVQVVESGGGLVQPGRSLRLSCAASGFTFDDYAMHWVRQAPGKGLEWVSGISWNSG SIVYADSVKGRFTISRDNAKNSLYLQLNSLRAEDTAFYYCAKAVSGYFPYFDYWGQGI LVTVSS (SEQ ID NO: 27) or EVQVVESGGGLVQPGRSLRLSCAASGFTFDDYAMHWVRQAPGKGLEWVSGISWNSG SIVYADSVKGRFTISRDNAKNSLYLQLNSLRAEDTAFYYCAKAVSGYFPYFHWGQGI LVTVSS (SEQ ID NO: 28) or EVQVVESGGGLVQPGRSLRLSCAASGFTFDDYAMYWVRQAPGKGLEWVSGISWNSG SIVYADSVKGRFTISRDNAKNSLYLQLNSLRAEDTAFYYCAKAVSGYFPYFDY WGQGI LVTVSS (SEQ ID NO: 29) or EVQVVESGGGLVQPGRSLRLSCAASGFTFDDYAMYWVRQAPGKGLEWVSGISWNSG SIVYADSVKGRFTISRDNAKNSLYLQLNSLRAEDTAFYYCAKAVSGYFPYFDYWGQGI LVTVSS (SEQ ID NO: 30) or EVQVVESGGGLVQPGRSLRLSCAASGFTFDDYAMYWVRQAPGKGLEWVSGISWNSG SIVYADSVKGRFTISRDNAKNSLYLQLNSLRAEDTAFYYCAKAVSGYFPYFHWGQGI LVTVSS (SEQ ID NO: 31) and/or a light chain variable region sequence having at least 80% sequence identity with the sequence DIVMTQSPDSLSVSLGERATINCKSSQSVLYSSNNKNYLGWYQQKPGQPPKLLIYWAS TRESGVPDRFSGSGSGTDFTLTISSLQAEDVAVYYCQQYYTTPSTFGQGTRLEIK (SEQ ID NO: 16), preferably whereby the CDR1, CDR2 and CDR3 sequences comprise at least 80% sequence identity with the sequences KSSQSVLYSSNNKNYLG (SEQ ID NO: 8) (CDR1), WASTRES (SEQ ID NO: 10) (CDR2) and QQYYTTP (SEQ ID NO: 12) (CDR3), more preferably a light chain variable region sequence DIVMTQSPDSLSVSLGERATINCKSSQSVLYSSNNKNYLGWYQQKPGQPPKLLIYWAS TRESGVPDRFSGSGSGTDFTLTISSLQAE- DVAVYYCQQYYTTPSTFGQGTRLEIK (SEQ ID NO: 16) or DIVMTQSPDSLSVSLGERATINCKSSQSVLYSSNNKNYLGWYQQKPGQPPKLLIYWAS IRESGVPDRFSGSGSGTDFTLTISSLQAEDVAVYYCQQYYTTPSTFGQGTRLEIK (SEQ ID NO: 32).

As already mentioned before, an antibody or functional part or functional equivalent according to the present invention is preferably of the IgG isotype, more preferably IgG1 or IgG3, in view of the stability of such immunoglobulin in vivo. In addition, as shown in the Examples, antibody AT14-012 is able to trigger complement dependent cytotoxicity (CDC) in tumor cells when the antibody is in a IgG3 backbone. Moreover, a mutation in the IgG Fc tail (E345R, EU numbering, as described in Kabat 1991) forces hexamerization of the antibody upon target binding, C1q deposition on the tumor cell surface and further induces concentration dependent cell death via CDC (De Jong 2016). Hence, in a particularly preferred embodiment, an antibody, functional part or functional equivalent according to the invention is of the IgG3 isotype. In a further preferred embodiment, an antibody, functional part or functional equivalent according to the invention is of the IgG isotype, preferably IgG1 or IgG3, more preferably IgG3, and comprises an arginine at amino acid position 345 (EU numbering).

As shown in the Examples, antibody AT14-012 is able to specifically bind amino acids K169, D171, V172, L173 and F176 of the CD9 sequence as depicted in FIG. 2. Now that this is known, binding compounds can be obtained or generated that compete with AT14-012 for the same epitope. For instance, a CD9 peptide comprising at least 4, preferably at least 5, or 6 of the above mentioned amino acid residues is provided, or a CD9 peptide consisting of at least 4, preferably at least 5, or 6 of the above mentioned amino acid residues, where after a non-human animal is immunized with such CD9 peptide, or with an immunogenic compound comprising such CD9 peptide, or with a nucleic acid molecule or functional equivalent thereof encoding such CD9 peptide, preferably followed by one or more booster administrations. Subsequently, antibodies that are specific for CD9 are harvested from said non-human animal alternatively, or additionally, CD9-specific B cells are harvested from said non-human animal. Such CD9-specific B-cells are particularly suitable for the production of CD9-specific antibodies. CD9-specific B-cells harvested from said immunized animal are for instance used for the production of hybridomas, from which CD9-specific antibodies are obtained. In other embodiments, said CD9-specific B cells harvested from said immunized animal are transduced with a Bcl-6 nucleic acid and with an anti/apoptotic nucleic acid such as for instance Bcl-xL or Mcl-1, and cultured in long term ex vivo B cell cultures, as for instance described in European Patent No. 1974017 and U.S. Pat. No. 9,127,251. This way, long term replicating B cell cultures are generated, wherein the B cells both replicate and produce antibody. In some embodiments, CD9-specific antibodies produced by said hybridomas or by such B cell culture are harvested and for instance used for anti-CD9 therapy, preferably after humanization of the antibodies in order to reduce side-effects. In some embodiments, an antibody and/or B cell obtained from said non-human animal is tested for competition with antibody AT14-012 for binding to CD9. This is for instance done by incubating CD9-expressing cells with said antibody or B cell obtained from said non-human animal, and subsequently adding antibody AT14-012. As a control, CD9-expressing cells are preferably incubated with antibody AT14-012 in the absence of any other antibody or B cell. If pre-incubation of CD9-expressing cells with an antibody or B cell obtained from said non-human animal appears to affect the binding of AT14-012 to said cells, it is concluded that said antibody or b cell obtained from said non-human animal competes with antibody AT14-012 for binding to CD9.

In some embodiments, the variable domain-encoding nucleic acid sequences of CD9-specific B cells obtained from said non-human animal are sequenced in order to obtain the nucleic acid sequences of the CD9-specific variable domains, where after one or more nucleic acid molecules comprising these sequences are introduced in producer cells, such as for instance E. coli, Chinese hamster ovary (CHO) cells, NSO cells (a mouse myeloma) or 293(T) cells, for the production of CD9-specific antibodies. Said one or more nucleic acid sequences are preferably codon optimized for said producer cell. As used herein, the term "codon" means a triplet of nucleotides (or functional equivalents thereof) that encode a specific amino acid residue. The term "codon optimized" means that one or more codons from the original, animal nucleic acid sequence are replaced by one or more codons that are preferred by a certain producer cell. These replacement codons preferably encode the same amino acid residue as the original animal codon that has been replaced.

In some embodiments, CD9-specific antibodies obtained from said non-human animal or from immune cells of said non-human animal are humanized, meaning that at least part of the animal amino acid sequence, preferably at least part or the whole of the framework sequences, is replaced by a human sequence in order to reduce adverse side-effects in humans.

Animal immunization protocols, including suitable administration procedures and adjuvants, procedures for obtaining and purifying antibodies and/or immune cells from such immunized animals, competition experiments and humanization procedures of non-human antibodies are well known in the art. Reference is for instance made to Hanly et al, 1995.

In some embodiments, a CD9 peptide comprising, or consisting of, at least 4, preferably at least 5, or 6 of the CD9 amino acid residues selected from the group consisting of K169, D171, V172, L173, T175 and F176 as depicted in FIG. 2, preferably of the CD9 amino acid residues selected from the group consisting of K169, D171, V172, L173 and F176, or a compound comprising such CD9 peptide, is used for screening a phage display library in order to identify and/or isolate CD9-specific immunoglobulins (typically Fab fragments). In some embodiments, a naïve phage display library is used. In preferred embodiments, a phage display library derived from one or more melanoma patients is used, so that the library will already be biased. In some embodiments, a CD9-specific immunoglobulin obtained from said phage display library is tested for competition with antibody AT14-012 for binding to CD9. This is for instance done using a competition test described herein.

Antibodies that are obtained, produced or selected with a method as described above will typically compete with antibody AT14-012 for at least part of the same CD9 epitope. Further provided is, therefore, an isolated, synthetic or recombinant antibody or functional part or functional equivalent thereof that competes with antibody AT14-012 for binding to CD9. Some embodiments provide an isolated, synthetic or recombinant antibody or functional part or functional equivalent thereof that competes with antibody AT14-012 for binding to at least 4 CD9 amino acids selected from the group consisting of K169, D171, V172, L173 and F176, as depicted in FIG. 2. In some embodiments, said antibody or functional part or functional equivalent competes with antibody AT14-012 for binding to at least 4, or at least 5, CD9 amino acids selected from the group consisting of K169, D171, V172, L173 and F176, as depicted in FIG. 2. In some embodiments, said antibody or functional part or functional equivalent competes with antibody AT14-012 for binding to CD9 amino acids K169, D171, V172, L173 and F176, as depicted in FIG. 2.

Another aspect of the invention provides an antibody or functional part or functional equivalent according to the invention, which is coupled to another compound. In one embodiment, a binding compound according to the invention is coupled to another therapeutic moiety, such as a chemotherapeutic drug or other toxic compound or radioactive compound, to form a so called "antibody-drug conjugate". In another embodiment, a moiety that is coupled to a binding compound according to the invention is an immunomodulatory molecule such as for instance a CD3-specific antibody. Such CD3-specific antibody is capable of binding T cells and, if coupled to a binding compound according to the invention, it will target T cells to CD9-containing cells such as melanoma cells, thereby enhancing an anti-melanoma T-cell response. This provides an even stronger anti-melanoma effect. One preferred embodiment of the invention therefore provides a bispecific or multispecific binding compound, comprising a CD9-specific binding compound according to the present invention and an immunomodulatory molecule, preferably a CD3-specific binding compound. Another preferred embodiment provides an anti-CD9 compound, said compound comprising a binding compound according to the present invention, which is specific for CD9, and a toxic moiety. In some other embodiments, a binding compound according to the present invention is coupled to a label. This allows detection of CD9-containing cells, such as for instance melanoma cells, using such labeled binding compound. Other embodiments provide a binding compound according to the invention that is coupled to another CD9-specific binding compound. In some embodiments, such other CD9-specific binding compound is also a binding compound according to the present invention. Provided is therefore a compound comprising two binding compounds according to the invention that are coupled to each other, such as for instance two coupled AT14-012 antibodies or functional parts or functional equivalents thereof. In some embodiments, a binding compound according to the invention is coupled to another CD9-specific binding compound, such as for instance a currently known anti CD9 antibody, in order to produce a bispecific compound. In some embodiments, a heavy chain of antibody AT14-012 is paired with a heavy chain of another CD9-specific antibody, in order to produce a bispecific antibody. Bispecific compounds and bispecific antibodies according to the invention allow, for instance, for increased binding of CD9-containing cells, especially when the two coupled binding compounds are specific for different CD9 epitopes. Such bispecific compound and/or bispecific antibody is thus very suitable for therapeutic or diagnostic applications. It is also possible to use bispecific compounds and bispecific antibodies according to the invention in assays wherein different CD9-containing cells are bound to the same bispecific binding compound.

In some embodiments, a synthetic or recombinant antibody is provided, or a functional part or a functional equivalent thereof, which comprises one Fab fragment of an antibody according to the present invention, preferably an AT14-012 Fab fragment, and one Fab fragment of another CD9-specific antibody. The resulting binding compound is monospecific for CD9, but each Fab arm will typically bind its own CD9 epitope. In some embodiments, the epitopes recognized by the Fab fragments are different from each other. In another embodiment, the epitopes are the same. The Fab arms may bind the epitopes with different affinity alternatively, the Fab arms bind their epitopes with essentially the same affinity, meaning that the $K_D$ of the Fab arms differ no more than 30%, preferably no more than 20% or no more than 10% from each other.

In some embodiments, a synthetic or recombinant antibody is provided, or a functional part or a functional equivalent thereof, which comprises one Fab fragment of an antibody according to the present invention, preferably an AT14-012 Fab fragment, and one Fab fragment of another antibody. For instance, such antibody comprises one Fab fragment of an antibody according to the invention and one Fab fragment of a blocking antibody specific for a complement regulatory protein or a blocking antibody specific for a co-inhibitory T cell molecule. Preferred examples of a blocking antibody specific for a complement regulatory protein from which a Fab fragment is present in such antibody is a CD55 blocking antibody, a CD46 blocking antibody or a CD59 blocking antibody, more preferably a CD55 blocking antibody. Preferred examples of a blocking antibody against a blocking antibody specific for a co-inhibitory T cell molecule from which a Fab fragment is present in such antibody is an anti-CTLA4 antibody, an anti-PD-1 antibody, an anti-PD-L1 antibody, an anti-PD-L2 antibody, an anti-SIRPα antibody, an anti-TIM3 antibody, an anti-LAG3 antibody, an anti-CD276 antibody, an anti-CD272 antibody, an anti-KIR antibody, an anti-A2AR antibody, an anti-VISTA antibody and an anti-IDO antibody, preferably an anti-PD-1 antibody or an anti-PD-L1 antibody.

Further provided is therefore an antibody or functional part or functional equivalent according to the invention, that is coupled to another compound. In some embodiments, said other compound is a detectable label, a chemotherapeutic drug, a toxic moiety, an immunomodulatory molecule, another CD9-specific binding compound, or a radioactive compound. Some embodiments provide antibody AT14-012 that is coupled to another compound, for instance any one of the compounds mentioned above. Some embodiments provide a bispecific antibody, or a functional part or functional equivalent thereof, comprising a Fab fragment of antibody AT14-012 and a Fab fragment of another CD9-specific antibody. Some embodiments provide a bispecific antibody, or a functional part or functional equivalent thereof, comprising a heavy chain of antibody AT14-012 paired with a heavy chain of another CD9-specific antibody.

In some embodiments, a binding compound according to the invention is coupled to another moiety, such as for example a chemotherapeutic agent or a CD3-specific antibody, via a linker such as for instance an acid-labile hydrazone linker, or via a peptide linker like citrulline-valine, or through a thioether linkage, or by sortase A catalyzed transamidation, which is described in detail in WO 2010/087994.

Sortase catalyzed transamidation involves engineering of a sortase recognition site (LPETGG) on the heavy chain of an antibody, preferably on the C-terminal part of the heavy chain, and on the moiety to be coupled to said antibody. The antibody and the moiety further typically contain a GGGGS sequence and a tag for purification purposes, such as a HIS tag. Subsequently sortase mediated transamidation is performed followed by click chemistry linkage. In a sortase catalyzed transamidation, "click chemistry linkage" typically involves chemical coupling of, for instance, an alkyne-containing reagent and, for instance, an azide-containing reagent which are added by sortase through addition of glycines to the sortase motif on the heavy chain of the antibody and to a sortase motif on the moiety (such as a protein, peptide or antibody) to be coupled to the antibody. In one embodiment, the invention therefore provides an antibody according to the invention wherein a sortase recognition site (LPETGG) is engineered on the heavy chain of the antibody, preferably on the C-terminal part of the heavy chain, the antibody preferably further containing a GGGGS sequence and a purification tag, such as a HIS tag.

In another embodiment, a binding compound according to the invention is coupled to another moiety via a thioether linkage. In such case, one or more cysteines are preferably incorporated into a binding compound according to the invention. Cysteines contain a thiol group and, therefore, incorporation of one or more cysteines into a binding compound according to the invention, or replacement of one or more amino acids by one or more cysteines of a binding compound according to the invention, enable coupling of said binding compound to another moiety. Said one or more cysteines are preferably introduced into a binding compound according to the invention at a position where it does not significantly influence folding of said binding compound, and does not significantly alter antigen binding or effector function. The invention therefore also provides a binding compound according to the invention that comprises a heavy chain sequence of antibody AT14-012, wherein at least one amino acid of said AT14-012 sequence (other than cysteine) has been replaced by a cysteine.

Another aspect of the invention provides an antibody or functional part or functional equivalent according to the invention, which is combined with another therapeutic agent. For instance, an antibody or functional part or functional equivalent according to the invention is combined with another agent that is capable of at least in part treating or preventing a disorder associated with CD9-expressing cells, preferably a disorder selected from the group consisting of CD9 positive cancer, osteoporosis, arthritis, lung inflammation, COPD, colitis, and a disorder associated with innate lymphoid cells. An antibody or functional part or functional equivalent according to the invention, which is combined with another therapeutic agent useful in the treatment and/or prevention of a CD9 positive cancer. Examples of such agents are complement regulatory proteins, antibodies specific for a co-inhibitory T cell molecule, small molecules against mutated BRAF (e.g. vemurafenib or dabrafenib) and other chemotherapy agents. Provided is therefore a use or method for at least in part treating or preventing a disorder associated with CD9-expressing cells according to the invention whereby an antibody or functional part or functional equivalent according to the invention is combined with a therapeutic agent useful in the treatment and/or prevention of a disorder associated with CD9-expressing cells, preferably a CD9 positive cancer. Also provided is a kit of parts comprising an antibody or functional part or functional equivalent according to the invention and a therapeutic agent useful in the treatment and/or prevention of a disorder associated with CD9-expressing cells, preferably a CD9 positive cancer. Preferred, but non-limiting examples of such agents are complement regulatory proteins, antibodies specific for a co-inhibitory T cell molecule, small molecules against mutated BRAF (e.g. vemurafenib or dabrafenib) and other chemotherapy agents. For instance, the Examples show that antibody AT14-012 E345R efficiently kills tumor cells by CDC in the presence of human complement factors, which lack the expression of CD55, an inhibitor of C3 convertase formation. Hence, when the antibody is combined with an agent capable of stimulating C3 convertase formation or capable of counter-acting inhibition of C3 convertase formation, such as a CD55 blocking antibody, complement dependent cell death of tumor cells may be induced. Antibodies against other complement regulatory proteins, blocking of which enhances CDC, such as a CD46 blocking antibody or a CD59 blocking antibody, may also be advantageously combined with an antibody, functional part or functional equivalent according to the invention.

Provided is therefore a use or method for at least in part treating or preventing a disorder associated with CD9-expressing cells according to the invention whereby an antibody or functional part or functional equivalent according to the invention is combined with an agent capable of stimulating C3 convertase formation or capable of counter-acting inhibition of C3 convertase formation. Said agent is preferably a CD55 blocking antibody, a CD46 blocking antibody or a CD59 blocking antibody, more preferably a CD55 blocking antibody. Said disorder is preferably a CD9 positive cancer, more preferably selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

Also provided is a kit of parts comprising an antibody or functional part or functional equivalent according to the invention and a therapeutic agent useful in the treatment and/or prevention of a disorder associated with CD9-expressing cells, preferably a CD9 positive cancer. In a preferred embodiment, said agent is an agent capable of stimulating C3 convertase formation or capable of counteracting inhibition of C3 convertase formation. Said agent is preferably a CD55 blocking antibody, a CD46 blocking antibody or a CD59 blocking antibody, more preferably a CD55 blocking antibody. Also provided is a kit of part comprising a nucleic acid molecule or functional equivalent, a vector or a cell according to the invention and an agent capable of stimulating C3 convertase formation or capable of counter-acting inhibition of C3 convertase formation. Said agent is preferably a CD55 blocking antibody, a CD46 blocking antibody or a CD59 blocking antibody, more preferably a CD55 blocking antibody.

An antibody or functional part or functional equivalent according to the invention is further optionally combined with an antibody specific for a co-inhibitory T cell molecule, such as an antibody blocking the PD1-PDL1-axis. Antibodies blocking the PD1-PDL1 axis, in particular those binding PD1, are now widely used to treat a wide variety of late stage cancer patients. The Examples show that when antibody AT14-012 is combined with nivolumab (Opdivo, Bristol-Myers Squibb), an anti-PD-1 antibody, the inhibition of tumor growth was strongly enhanced in comparison to treatment with AT14-012 alone.

An antibody against a co-inhibitory T cell molecule is preferably a blocking antibody. A "blocking antibody" as used herein refers to an antibody or fragment whose binding to it antigen reduces or blocks the interaction between the antigen and its target. For instance, a blocking antibody against CTLA-4 refers to an antibody that reduces or blocks the binding of soluble human CTLA-4 to cell-expressed CD80 and CD86 (B7-1 and B7-2) and thereby inhibits the T cell inhibitory activity of CTLA-4. Suitable antibody against a co-inhibitory T cell molecule include, but are not limited to, a blocking antibody specific for cytotoxic T-lymphocyte antigen-4 (CTLA-4), programmed death-1 (PD-1), PD-ligand 1 (PD-L1), PD-L2, Signal-regulatory protein alpha (SIRPα), T-cell immunoglobulin- and mucin domain-3-containing molecule 3 (TIM3), lymphocyte-activation gene 3 (LAG3), killer cell immunoglobulin-like receptor (KIR), CD276, CD272, A2AR, VISTA and indoleamine 2,3 dioxygenase (IDO).

Provided is therefore a use or method for at least in part treating or preventing a disorder associated with CD9-expressing cells according to the invention whereby an antibody or functional part or functional equivalent according to the invention is combined with a blocking antibody specific for a co-inhibitory T cell molecule. Said antibody is preferably selected from the group consisting of an anti-CTLA4 antibody, an anti-PD-1 antibody, an anti-PD-L1 antibody, an anti-PD-L2 antibody, an anti-SIRPα antibody, an anti-TIM3 antibody, an anti-LAG3 antibody, an anti-CD276 antibody, an anti-CD272 antibody, an anti-KIR antibody, an anti-A2AR antibody, an anti-VISTA antibody and an anti-IDO antibody. Suitable antibodies used as a further immunotherapy component are nivolumab, pembrolizumab, lambrolizumab, ipilimumab and lirilumab. In a particularly preferred embodiment, said antibody is an antibody blocking the PD1-PDL1-axis, such as an anti-PD1 antibody or an anti-PDL1 antibody, more preferably an anti-PD1 antibody. Said disorder is preferably a CD9 positive cancer, more preferably selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

Also provided is a kit of parts comprising an antibody or functional part or functional equivalent according to the invention and a blocking antibody specific for a co-inhibitory T cell molecule. Also provided is a kit of part comprising a nucleic acid molecule or functional equivalent, a vector or a cell according to the invention and a blocking antibody specific for a co-inhibitory T cell molecule. Said antibody is preferably selected from the group consisting of an anti-CTLA4 antibody, an anti-PD-1 antibody, an anti-PD-L1 antibody, an anti-PD-L2 antibody, an anti-SIRPα antibody, an anti-TIM3 antibody, an anti-LAG3 antibody, an anti-CD276 antibody, an anti-CD272 antibody, an anti-KIR antibody, an anti-A2AR antibody, an anti-VISTA antibody and an anti-IDO antibody. Suitable antibodies used as a further immunotherapy component are nivolumab, pembrolizumab, lambrolizumab, ipilimumab and lirilumab. In a particularly preferred embodiment, said antibody is an antibody blocking the PD1-PDL1-axis, such as a PD1 blocking antibody or a PDL1 blocking antibody, more preferably a PD1 blocking antibody.

A kit of parts according to the invention may comprise one or more containers filled with pharmaceutical composition comprising an antibody, functional part or functional equivalent according to the invention and a pharmaceutical composition comprising the agent capable of stimulating C3 convertase formation or capable of counteracting inhibition of C3 convertase formation, preferably a CD55 blocking antibody, or the blocking antibody specific for a co-inhibitory T cell molecule, preferably a PD1 or PDL1 blocking antibody. The kit of part or the one or more containers further optionally comprises one or more pharmaceutically acceptable excipients. Associated with such kit of parts or container(s) can be various written materials such as instructions for use, or a notice in the form prescribed by a governmental agency regulating the manufacture, use or sale of pharmaceuticals products, which notice reflects approval by the agency of manufacture, use, or sale. Preferably, a kit of parts comprises instructions for use.

Also provided is a pharmaceutical composition comprising a an antibody or functional part or functional equivalent according to any one of claims 1-15, a therapeutic agent useful in the treatment and/or prevention of a disorder associated with CD9-expressing cells, preferably a CD9 positive cancer, and a pharmaceutically acceptable carrier, diluent or excipient. In a preferred embodiment, said agent is an agent capable of stimulating C3 convertase formation or capable of counteracting inhibition of C3 convertase formation, preferably a CD55 blocking antibody, a CD46 blocking antibody or a CD59 blocking antibody, more preferably a CD55 blocking antibody. In a further preferred embodiment, said agent is a blocking antibody specific for a co-inhibitory T cell molecule, preferably selected from the group consisting of an anti-CTLA4 antibody, an anti-PD-1 antibody, an anti-PD-L1 antibody, an anti-PD-L2 antibody, an anti-SIRPα antibody, an anti-TIM3 antibody, an anti-LAG3 antibody, an anti-CD276 antibody, an anti-CD272 antibody, an anti-KIR antibody, an anti-A2AR antibody, an anti-VISTA antibody and an anti-IDO antibody, more preferably a PD1 blocking antibody or a PDL1 blocking antibody.

Also, provided herewith are nucleic acid molecules and functional equivalents thereof, and vectors, encoding at least one CDR region of an antibody, functional part or functional equivalent or binding compound according to the invention. Preferably, at least the heavy chain CDR1-3 regions and the light chain CDR 1-3 regions of such binding compound are encoded by one or more nucleic acid molecules or functional equivalents or vectors according to the present invention. In some embodiments, the heavy and light chain variable regions of a binding compound according to the invention are encoded. Some embodiments of the invention thus provide an isolated, synthetic or recombinant nucleic acid molecule with a length of at least 15 nucleotides, or a functional equivalent thereof, or a vector, encoding at least one CDR region of an antibody or functional part or functional equivalent according to the invention. Preferably, said CDR region is a CDR region from antibody AT14-012, or a variant thereof as described herein that has the same or higher binding affinity as antibody AT14-012.

In some embodiments, a nucleic acid molecule according to the invention has a length of at least 30 nucleotides, more preferably at least 50 nucleotides, more preferably at least 75 nucleotides. A nucleic acid molecule according to the invention is for instance isolated from a B-cell which is capable of producing an antibody according to the invention. Said B-cell preferably produces antibody AT14-012, or a variant thereof as described herein that has the same or higher binding affinity as antibody AT14-012. Some embodiments provide one or more nucleic acid molecules, or functional equivalents or vectors, encoding at least the heavy chain CDR3 sequence and the light chain CDR3 sequence of AT14-012, or a variant thereof as described herein that has the same or higher binding affinity as antibody AT14-012.

As used herein the term "an isolated, synthetic or recombinant nucleic acid molecule with a length of at least 15 nucleotides, or a functional equivalent thereof, encoding at least one CDR region of an antibody or functional part or functional equivalent according to the invention" is herein also referred to as "a nucleic acid molecule or functional equivalent according to the invention".

As used herein, a nucleic acid molecule or nucleic acid sequence of the invention preferably comprises a chain of nucleotides, more preferably DNA, cDNA or RNA. In other embodiments, a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid molecule" thus encompasses a chain comprising non-natural nucleotides, modified nucleotides and/or non-nucleotide building blocks which exhibit the same function as natural nucleotides.

Nucleic acid sequences encoding the heavy chain and light chain CDR regions of antibody AT14-012 are depicted in Table 1 and FIG. 3. Nucleic acid molecules having a sequence that differs from any one of the CDR nucleic acid sequences depicted in Table 1 and FIG. 3, but wherein nucleic acid codons are present which encode the same CDR amino acid sequence(s) as depicted in Table 1 and FIG. 3, are also encompassed by the invention. Such nucleic acid molecules for instance comprise nucleic acid sequences that have been codon optimized for a producer cell, such as for instance E. coli or Chinese hamster ovary (CHO) cells, NSO cells (a mouse myeloma) or 293(T) cells, enabling high scale production of binding compounds according to the invention having the same CDR amino acid sequence(s) as antibody AT14-012. It should be noted that antibody production can be done by any recombinant antibody production system; the four producer cell systems mentioned here are only a few examples of the many systems that are available to date. As used herein, the term "codon" means a triplet of nucleotides (or functional equivalents thereof) that encode a specific amino acid residue. The term "codon optimized" means that one or more codons from the original, human nucleic acid sequence is replaced by one or more codons that are preferred by a certain antibody production system. These replacement codons preferably encode the same amino acid residue as the original human codon that has been replaced. Alternatively, one or more replacement codons encode a different amino acid residue. This preferably results in conservative amino acid substitution, although this is not necessary. Typically, in constant regions and framework regions one or more amino acid substitutions are generally allowed. In CDR regions, preferably codons are used that encode the same amino acid residue as the original human codon that has been replaced.

Furthermore, nucleic acid molecules encoding a heavy or light chain CDR which is not identical to, but based on, a CDR sequence of antibody AT14-012 are also encompassed by the invention, as long as the resulting CDR has at least 80% sequence identity with a CDR sequence of antibody AT14-012.

Further provided is, therefore, a nucleic acid molecule or functional equivalent thereof or a vector, comprising a sequence that has at least 80%, preferably at least 85%, or at least 90%, or at least 95%, or at least 96%, or at least 97%, or at least 98%, or at least 99%, sequence identity with a CDR sequence of antibody AT14-012. Preferably, the resulting CDR differs in no more than three, preferably in no more than two, preferably in only one amino acid from the original CDR sequence of an antibody according to the invention.

Some embodiments provide one or more nucleic acid molecules or functional equivalents or vectors according to the invention, that encode at least the heavy chain CDR 1-3 and the light chain CDR 1-3 regions of antibody AT14-012 or variants thereof that have the same of higher binding affinity further provided is therefore one or more nucleic acid molecules or functional equivalents or vectors according to the invention that comprise:

a heavy chain CDR1 encoding nucleic acid sequence which encodes the sequence DYAMH (SEQ ID NO: 2) or DYAMY (SEQ ID NO: 21), and/or a heavy chain CDR2 encoding nucleic acid sequence which encodes the sequence GISWNSGSIVY-ADSVKG (SEQ ID NO: 4), and/or a heavy chain CDR3 encoding nucleic acid sequence which encodes the sequence AVSGYYPYFDY (SEQ ID NO: 6) or AVSGYFPYFDY (SEQ ID NO: 22) or AVSGYYPYFHY (SEQ ID NO: 23) or AVSGYFPYFHY (SEQ ID NO: 24), and/or a light chain CDR1 encoding nucleic acid sequence which encodes the sequence KSSQSVLYSSNNKNYLG (SEQ ID NO: 8), and/or a light chain CDR2 encoding nucleic acid sequence which encodes the sequence WASTRES (SEQ ID NO: 10) or WASIRES (SEQ ID NO: 25), and/or a light chain CDR3 encoding nucleic acid sequence which encodes the sequence QQYYTTP (SEQ ID NO: 12).

Further provided is one or more nucleic acid molecules or functional equivalents or vectors, comprising a sequence that has at least 80% sequence identity with one or more sequences selected from the group consisting of:

gat tat gcc atg cac (SEQ ID NO: 1); and ggt att agt tgg aat agt ggt agc ata gtc tat gcg gac tct gtg aag ggc (SEQ ID NO: 3); and gcc gtg agt ggt tat tat ccc tac ttt gac tac (SEQ ID NO: 5); and aag tcc agc cag agt gtt tta tac agc tcc aac aat aag aac tac tta ggt (SEQ ID NO: 7); and tgg gca tct acc cgg gaa tcc (SEQ ID NO: 9); and cag caa tat tat act act cct (SEQ ID NO: 11).

These are the heavy and light chain CDR1-3 nucleic acid sequences of antibody AT14012, as depicted in Table 1 and FIG. 3. In some embodiments, said sequence identities are at least 85%, or at least 86%, or at least 87%, or at least 88%, or at least 89%, or at least 90%, or at least 91%, or at least 92%, or at least 93%, or at least 94%, or at least 96%, or at least 96%, or at least 97%, or at least 98%, or at least 99%, or 100%.

Preferably, the above mentioned heavy and light chain CDR1-3 sequences of AT14-012, or sequences that are at least 80% identical thereto, are all present. Further provided is therefore one or more nucleic acid molecules or functional equivalents or vectors that comprise:

a heavy chain CDR1 encoding nucleic acid sequence that has at least 80% sequence identity with the sequence gat tat gcc atg cac (SEQ ID NO: 1), and a heavy chain CDR2 encoding sequence that has at least 80% sequence identity with the sequence ggt att agt tgg aat agt ggt agc ata gtc tat gcg gac tct gtg aag ggc (SEQ ID NO: 3), and a heavy chain CDR3 encoding sequence that has at least 80% sequence identity with the sequence gcc gtg agt ggt tat tat ccc tac ttt gac tac (SEQ ID NO: 5), and a light chain CDR1 encoding sequence that has at least 80% sequence identity with the sequence aag tcc agc cag agt gtt tta tac agc tcc aac aat aag aac tac tta ggt (SEQ ID NO: 7), and a light chain CDR2 encoding sequence that has at least 80% sequence identity with the sequence tgg gca tct acc cgg gaa tcc (SEQ ID NO: 9), and a light chain CDR3 encoding sequence that has at least 80% sequence identity with the sequence cag caa tat tat act act cct (SEQ ID NO: 11).

In some embodiments, said sequence identities are at least 85%, or at least 86%, or at least 87%, or at least 88%, or at least 89%, or at least 90%, or at least 91%, or at least 92%, or at least 93%, or at least 94%, or at least 96%, or at least 96%, or at least 97%, or at least 98%, or at least 99%, or 100%. Preferably, the encoded CDR amino acid sequences differ in no more than three, preferably in no more than two, preferably in only one amino acid from the heavy and light chain CDR1-3 amino acid sequences of antibody AT14-012.

Some embodiments provide nucleic acid molecules or functional equivalents or vectors according to the invention that encode at least the heavy chain variable region sequence and/or the light chain variable region sequence of an antibody or functional part or functional equivalent according to the invention. Preferably, said at least one nucleic acid molecule or functional equivalent or vector encodes at least the heavy chain variable region sequence and/or the light chain variable region sequence of antibody AT14-012, or a sequence that is at least 80% identical thereto.

Further provided is therefore one or more nucleic acid molecules or functional equivalents or vectors, comprising a sequence that has at least 80% sequence identity with the sequence gaa gtg cag gtg gtg gag tct ggg gga ggc ttg gta cag cct ggc agg tcc ctg aga ctc tcc tgt gca gcc tct gga ttc acc ttt gat gat tat gcc atg cac tgg gtc cgg caa gct cca ggg aag ggc ctg gag tgg gtc tca ggt att agt tgg aat agt ggt agc ata gtc tat gcg gac tct gtg aag ggc cga ttc acc atc tcc aga gac aac gcc aag aac tcc ctg tat ctg caa ctg aac agt ctg aga gct gag gac acg gcc ttc tat tac tgt gca aaa gcc gtg agt ggt tat tat me tac ttt gac tac tgg ggc cag gga att ttg gtc acc gtc tcc tca (SEQ ID NO: 13), and/or comprising a sequence that has at least 80% sequence identity with the sequence gac atc gtg atg acc cag tct cca gac tcc ctg tct gtg tct ctg ggc gag agg gcc acc atc aac tgc aag tcc agc cag agt gtt tta tac agc tcc aac aat aag aac tac tta ggt tgg tac cag cag aaa cca gga cag cct cct aag ctg ctc att tac tgg gca tct acc cgg gaa tcc ggg gtc cct gac cga ttc agt ggc agc ggg tct ggg aca gat ttc act ctc acc atc agc agc ctg cag gct gaa gat gtg gca gtt tat tac tgt cag caa tat tat act act cct tcc acc ttc ggc caa ggg aca cga ctg gag att aaa (SEQ ID NO: 15).

Preferably, one or more nucleic acid molecules or a functional equivalents or vectors according to the invention encode both a heavy chain variable region and a light chain variable region that resemble the heavy chain variable region and the light chain variable regions of AT14-012 as depicted in Table 1 and FIG. 3. Further provided is therefore one or more nucleic acid molecules or functional equivalents or vectors, comprising a sequence that has at least 80% sequence identity with the sequence gaa gtg cag gtg gtg gag tct ggg gga ggc ttg gta cag cct ggc agg tcc ctg aga ctc tcc tgt gca gcc tct gga ttc acc ttt gat gat tat gcc atg cac tgg gtc cgg caa gct cca ggg aag ggc ctg gag tgg gtc tca ggt att agt tgg aat agt ggt agc ata gtc tat gcg gac tct gtg aag ggc cga ttc acc atc tcc aga gac aac gcc aag aac tcc ctg tat ctg caa ctg aac agt ctg aga gct gag gac acg gcc ttc tat tac tgt gca aaa gcc gtg agt ggt tat tat cm tac ttt gac tac tgg ggc cag gga att ttg gtc acc gtc tcc tca (SEQ ID NO: 13), and comprising a sequence that has at least 80% sequence identity with the sequence gac atc gtg atg acc cag tct cca gac tcc ctg tct gtg tct ctg ggc gag agg gcc acc atc aac tgc aag tcc agc cag agt gtt tta tac agc tcc aac aat aag aac tac tta ggt tgg tac cag cag aaa cca gga cag cct cct aag ctg ctc att tac tgg gca tct acc cgg gaa tcc ggg gtc cct gac cga ttc agt ggc agc ggg tct ggg aca gat ttc act ctc acc atc agc agc ctg cag gct gaa gat gtg gca gtt tat tac tgt cag caa tat tat act act cct tcc acc ttc ggc caa ggg aca cga ctg gag att aaa (SEQ ID NO: 15).

In some embodiments, said sequence identities are at least 85%, or at least 86%, or at least 87%, or at least 88%, or at least 89%, or at least 90%, or at least 91%, or at least 92%, or at least 93%, or at least 94%, or at least 96%, or at least 96%, or at least 97%, or at least 98%, or at least 99%, or 100%.

In some embodiments, nucleic acid molecules and functional equivalents thereof and vectors are provided that encode an antibody or functional part or equivalent according to the invention. In some embodiments, nucleic acid molecules and functional equivalents thereof and vectors are provided that encode antibody AT14-012, or a functional part or a functional equivalent thereof. In some embodiments, said nucleic acid molecules or functional equivalents or vectors are codon optimized for a non-human recombinant expression system, such as a non-human host cell like *E. coli*, CHO, NSO, or 293 cells.

Some embodiments provide a vector comprising a nucleic acid molecule or functional equivalent according to the invention. As used herein "a vector comprising a nucleic acid molecule or functional equivalent according to the invention" is also referred to as "a vector according to the invention". These terms encompass one or more vector(s) according to the invention, comprising one or more nucleic acid molecule(s) or functional equivalent(s) according to the invention. As used herein, the singular term "a" encompasses the term "one or more".

Methods for constructing vectors comprising one or more nucleic acid molecule(s) or functional equivalent(s) according to the invention are well known in the art. Non-limiting examples of vectors suitable for generating a vector of the invention are retroviral and lentiviral vectors. Such vectors are suitable for a variety of applications. For instance, a vector of the invention comprising a therapeutically beneficial nucleic acid sequence according to the invention is suitable for prophylactic or therapeutic applications against melanoma. Administration of such vector(s) to an individual, preferably a human, in need thereof results in expression of said prophylactic or therapeutic nucleic acid sequence in vivo resulting in at least partial treatment or prophylaxis against melanoma. Said vector can also be used in applications involving in vitro expression of a nucleic acid molecule of interest, for instance for (commercial) production of antibodies or functional equivalents according to the invention. Hence, nucleic acid molecules, functional equivalents and vectors according to the invention are particularly useful for generating antibodies or functional parts or functional equivalents according to the invention, which are specific for CD9. This is for instance done by introducing such nucleic acid molecule(s) or functional equivalent(s) or vector(s) into a cell so that the cell's nucleic acid translation machinery will produce the encoded antibodies or functional parts or functional equivalents. In some embodiments, at least one nucleic acid molecule or functional equivalent or vector encoding a heavy and light chain variable region of a binding compound according to the invention is/are expressed in so called producer cells, such as for instance *E. coli*, CHO, NSO or 293(T) cells, some of which are adapted to commercial antibody production. Of note, any recombinant antibody production system is suitable; these four producer cell systems mentioned are only a few examples of the many systems that are available to date. As described herein before, in such cases it is preferred to use nucleic acid molecules or functional equivalents thereof wherein the original human AT14-012 sequences as provided herein are codon optimized for the producer cell. Proliferation of said producer cells results in a producer cell line capable of producing binding compounds according to the invention. Preferably, said producer cell line is suitable for producing antibodies for use in humans. Hence, said producer cell line is preferably free of pathogenic agents such as pathogenic micro-organisms. In some embodiments, antibody AT14-012 is produced in such producer cell line.

Further provided is therefore an isolated or recombinant cell, comprising at least one nucleic acid molecule and/or functional equivalent and/or vector according to the invention. Such cell is preferably an antibody producing cell capable of producing a binding compound according to the invention, such as for instance antibody AT14-012. Further provided is a method for producing an antibody or functional part or functional equivalent according to the invention, the method comprising providing a cell with at least one nucleic acid molecule or functional equivalent or vector according to the invention, and allowing said cell to translate said at least one nucleic acid molecule or functional equivalent or vector, thereby producing said antibody or functional part or functional equivalent according to the invention. In some embodiments, said antibody is AT14-012 optionally having one or more of the heavy chain mutations H40Y, Y112F and D116H and/or light chain mutation T66I (IMGT numbering), or a functional part or a functional equivalent thereof. Said method according to the invention preferably further comprises a step of harvesting, purifying and/or isolating said antibody or functional part or functional equivalent according to the invention. Obtained binding compounds according to the invention are for instance suitable for use in human therapy or diagnostics, optionally after additional purifying, isolation or processing steps.

In some embodiments, at least one nucleic acid molecule or functional equivalent or vector according to the invention is introduced into a non-human animal, for instance for in vivo antibody production. Further provided is therefore an isolated or recombinant non-human animal, comprising at least one nucleic acid molecule or functional equivalent or vector according to the invention. Methods for producing transgenic non-human animals are known in the art. Reference is for instance made to EC Lee, Nature Biotechnology, 2013.

Binding compounds according to the present invention are suitable for use against melanoma. Furthermore, CD9 also has a role in other diseases, like for instance other kinds of tumors that also express CD9. Other non-limiting examples of diseases that are associated with CD9-positive cells are osteoporosis and arthritis (Iwai et al. and Hattori et al.), lung inflammation and COPD (Takeda et al. and Jin et al.), and colitis (Wagner et al.). For instance, CD9 is abundantly expressed in activated osteoclasts in ovariectomy-induced osteoporosis and in bone erosions of collagen-induced arthritis (Iwai et al. and Hattori et al.). CD9 is also expressed in innate lymphoid cells. Other non-limiting examples of diseases that are associated with CD9-positive cells are virus infections (for instance HIV or herpes or influenza), bacterial infections, CMV retinitis, oral candidiasis, Glanzmann thrombasthenia and diphtheria.

Since binding compounds according to the present invention are specific for CD9, they are suitable for use against these disorders as well. Binding compounds according to the present invention are thus particularly suitable for use as a medicine or prophylactic agent. Provided is therefore an antibody or functional part or functional equivalent according to the invention for use as a medicament and/or prophylactic agent. In some embodiments, binding compounds according to the invention are used that consist of human sequences, in order to reduce the chance of adverse side effects when human individuals are treated. Said antibody preferably comprises antibody AT14-012. Further provided is therefore antibody AT14-012 for use as a medicament and/or prophylactic agent. In some embodiments, human sequences are synthetically or recombinantly produced based on the sequence of AT14-012, optionally using codon optimized nucleic acid sequences that encode the same AT14-012 amino, or sequences that are at least 80% identical thereto.

Also provided is a nucleic acid molecule or functional equivalent thereof according to the invention, or a vector according to the invention comprising such nucleic acid molecule or functional equivalent, or a cell according to the invention, for use as a medicament and/or prophylactic agent. When (a vector comprising) one or more nucleic acid molecule(s) or functional equivalent(s) according to the invention is/are administered, the nucleic acid molecule(s) or functional equivalent(s) will be translated in situ into a binding compound according to the invention. The resulting binding compounds according to the invention will subsequently counteract or prevent disorders associated with CD9-expressing cells, like for instance CD9-expressing tumors, osteoporosis, arthritis, lung inflammation, COPD, colitis, or disorders associated with innate lymphoid cells. Likewise, introduction of a cell according to the invention into a patient in need thereof will result in in vivo generation of therapeutic or prophylactic anti-CD9 antibodies, or functional parts or functional equivalents, according to the invention.

Some embodiments provide an antibody or functional part or functional equivalent according to the invention, or a nucleic acid molecule or functional equivalent or vector according to the invention, or a cell according to the invention, for use in a method for at least in part treating or preventing a disorder associated with CD9-expressing cells. Some embodiments provide antibody AT14-012 for use in a method for at least in part treating or preventing a disorder associated with CD9-expressing cells. As used herein, the term "a disorder associated with CD9-expressing cells" means any disease that involves the presence of CD9-expressing disease-specific cells. In some embodiments, such cells are a causative factor of the disease, as is often the case for CD9-expressing malignant cells. In some embodiments, the presence of such cells cause adverse symptoms, such as for instance inflammation and/or pain. A non-limiting example of a disorder associated with CD9-expressing cells is a cancer with CD9-expressing tumor cells, like for instance melanoma, colorectal cancer, pancreatic cancer, esophageal cancer, lung cancer, breast cancer, ovarian cancer, stomach cancer, basal cell carcinoma, squamous cell carcinoma, AML, multiple myeloma, gastric cancer, liver cancer, cervical cancer, renal cell carcinoma, prostate cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

As used herein, a tumor cell that expresses CD9 is also referred to as a CD9-positive tumor cell or a CD9-positive malignant cell. A cancer wherein at least part of the tumor cells express CD9 is referred to as a "CD9-positive cancer". Other non-limiting examples of a disorder associated with CD9-expressing cells are osteoporosis, arthritis, lung inflammation, COPD, colitis and disorders associated with innate lymphoid cells.

Further provided is therefore an antibody or functional part or functional equivalent according to the invention, or a nucleic acid molecule or functional equivalent or vector according to the invention, or a cell according to the invention, for use in a method for at least in part treating or preventing a disorder associated with CD9-expressing cells, wherein said disorder is selected from the group consisting of CD9-positive cancer, osteoporosis, arthritis, lung inflammation, COPD, colitis, and a disorder associated with innate lymphoid cells. Said CD9-positive cancer is preferably selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

The Examples show that AT14-012 is able to kill melanoma cells via antibody dependent cytotoxicity (ADCC) while minimal cell death was observed when primary Human Artery Endothelial Cells (HAECs). In addition, antibody AT14-012 has been shown to be able to trigger complement dependent cytotoxicity (CDC) when the antibody is in a IgG3 backbone. Hence, without wishing to be bound by theory, it is speculated that the anti-tumor reactivity of AT1412 is at least in part mediated via ADCC. Hence, in a preferred embodiment, an antibody, functional part or functional equivalent according to the invention or for use according to the invention is able to induced antibody dependent cytotoxicity (ADCC) and/or complement dependent cytotoxicity (CDC) in CD9-expressing cells.

A preferred antibody for use in any of the recited methods is antibody AT14-012, or a variant of antibody AT14-012 described herein that the same binding specificity and the same or higher affinity as antibody AT14-012.

In some embodiments, antibody AT14-012 optionally having one or more of the mutations H40Y, Y112F and D116H and/or light chain mutation T66I (IMGT numbering), or a functional part or functional equivalent thereof, or at least one nucleic acid molecule or functional equivalent thereof encoding AT14-012 optionally having one or more of the mutations H40Y, Y112F and D116H and/or light chain mutation T66I (IMGT numbering), or a functional part or functional equivalent thereof, or at least one vector or cell comprising said nucleic acid molecule or functional equivalent, is preferably used for at least in part treating and/or preventing melanoma. As used herein the term "at least in part treating and/or preventing melanoma" includes counteracting melanoma tumor growth and/or alleviating symptoms resulting from the presence of melanoma cells in a patient. Also provided is therefore a use of antibody AT14-012 optionally having one or more of the mutations H40Y, Y112F and D116H and/or light chain mutation T66I (IMGT numbering), or a functional part or functional equivalent thereof, or of at least one nucleic acid molecule or functional equivalent encoding AT14-012 optionally having one or more of the mutations H40Y, Y112F and D116H and/or light chain mutation T66I (IMGT numbering), or a functional part or functional equivalent thereof, or of at least one vector or cell comprising said nucleic acid molecule or functional equivalent, for the preparation of a medicament and/or prophylactic agent for at least in part treating and/or preventing melanoma. Further provided is antibody AT14-012 optionally having one or more of the mutations H40Y, Y112F and D116H and/or light chain mutation T66I (IMGT numbering), or a functional part or functional equivalent thereof, or at least one nucleic acid molecule or functional equivalent encoding AT14-012 optionally having one or more of the mutations H40Y, Y112F and D116H and/or light chain mutation T66I (IMGT numbering), or a functional part or functional equivalent thereof, or at least one vector or cell comprising said nucleic acid molecule or functional equivalent, for use in a method for at least in part treating and/or preventing melanoma.

In some embodiments, a binding compound according to the invention is coupled to a therapeutic moiety, such as a chemotherapeutic drug or other toxic compound or a radioactive compound or an immunomodulatory molecule such as for instance a CD3-specific antibody, to form a so called "antibody-drug conjugate" or a "chimeric antigen receptor (CAR) T cell", respectively, which is able to counteract a myeloproliferative or lymphoproliferative disorder.

Further embodiments provide a composition comprising an antibody or functional part or functional equivalent according to the invention. A composition comprising a nucleic acid molecule or functional equivalent according to the invention is also provided, as well as a composition comprising a vector or a cell according to the invention. In some embodiments, said antibody is AT14-012, optionally having one or more of the mutations H40Y, Y112F and D116H and/or light chain mutation T66I (IMGT numbering). In some embodiments, a composition according to the invention comprises antibody AT14-012 optionally having one or more of the mutations H40Y, Y112F and D116H and/or light chain mutation T66I (IMGT numbering), or a functional part or functional equivalent thereof, and another CD9-specific antibody. Said other CD9-specific antibody preferably binds a different CD9 epitope as compared to AT14-012. Such combination of different CD9-specific binding compounds is particularly suitable for binding and/or counteracting CD9-positive cells, such as melanoma cells or other CD9-positive tumor cells.

In some embodiments, a composition according to the present invention is a pharmaceutical composition. Such pharmaceutical composition preferably also comprises a pharmaceutical acceptable carrier, diluent and/or excipient. Non-limiting examples of suitable carriers for instance comprise keyhole limpet haemocyanin (KLH), serum albumin (e.g. BSA or RSA) and ovalbumin. In one preferred embodiment said suitable carrier comprises a solution, like for example saline. A pharmaceutical composition according to the invention is preferably suitable for human use.

The invention further provides a method for at least in part treating and/or preventing a disorder associated with CD9-expressing cells, comprising administering to an individual in need thereof a therapeutically effective amount of an antibody or functional part or functional equivalent according to the invention, and/or a nucleic acid molecule or functional equivalent thereof according to the invention, and/or a vector or cell according to the invention, and/or a composition according to the invention. As used herein, an "individual" or "subject" is a human or a non-human animal, preferably a human patient suffering from a CD9-positive cancer, osteoporosis, arthritis, lung inflammation, COPD, colitis, or a disorder associated with innate lymphoid cells. In some embodiments, said human individual is a melanoma patient. Said composition is preferably a pharmaceutical composition according to the invention. A binding compound or a nucleic acid molecule or a functional equivalent or a vector or a pharmaceutical composition according to the invention is preferably administered via one or more injections. Typical doses of administration of a binding compound according to the invention are between 0.1 and 10 mg per kg body weight.

A binding compound according to the invention is also particularly useful for detection of CD9 expressing cells. For instance, if an individual, preferably a human, is suspected of suffering from a disorder associated with CD9-expressing cells, a sample such as a blood or tissue sample from said individual can be tested for the presence of CD9-expressing cells (also referred to as CD9-positive cells), using a binding compound according to the invention. In some embodiments said sample is mixed with a binding compound according to the invention, which will specifically bind CD9-positive cells. CD9-positive cells, such as for instance melanoma cells, bound to a binding compound according to the invention can be isolated from the sample and/or detected using any method known in the art, for example, but not limited to, isolation using magnetic beads, streptavidin-coated beads, or isolation through the use of secondary antibodies immobilized on a column. Alternatively, or additionally, a binding compound according to the invention is labeled in order to be able to detect said binding compound. Such binding compound is for instance fluorescently labeled, enzymatically labeled, or radioactively labeled. Alternatively, a binding compound according to the invention is detected using a labeled secondary antibody which is directed against said binding compound.

If a binding compound according to the invention appears to be bound to a component of a patient's sample, it is indicative for the presence of CD9-positive cells. This way, disease-specific CD9 positive cells like melanoma cells can be detected. Some embodiments therefore provide a use of an antibody or functional part or functional equivalent according to the invention for determining whether a sample comprises CD9-expressing cells. In some embodiments said antibody or functional part or functional equivalent according to the invention is used for determining whether a sample comprises CD9-expressing tumor cells. Also provided is a method for determining whether CD9-expressing cells, preferably CD9 positive tumor cells, are present in a sample comprising:
 contacting said sample with an antibody or functional part or functional equivalent according to the invention, and
 allowing said antibody or functional part or functional equivalent to bind CD9-expressing cells, if present, and
 determining whether or not CD9-expressing cells, such as for instance CD9 positive tumor cells, are bound to said antibody or functional part or functional equivalent, thereby determining whether or not CD9-expressing (tumor) cells are present in said sample. In some embodiments, said CD9-expressing tumor cells are melanoma cells.

As shown in the Examples, antibody AT14-012 is particularly suitable for detecting CD9-positive cells, like for instance CD9-positive tumor cells. Further provided is therefore a use of antibody AT14-012 optionally having one or more of the mutations H40Y, Y112F and D116H and/or light chain mutation T66I (IMGT numbering), or a functional part or functional equivalent thereof, for determining whether a sample comprises CD9-expressing cells. Also provided is a use of antibody AT14-012 optionally having one or more of the mutations H40Y, Y112F and D116H and/or light chain mutation T66I (IMGT numbering), or a functional part or functional equivalent thereof, for determining whether a sample comprises CD9-expressing tumor cells, like for instance melanoma cells or colorectal cancer cells or pancreatic cancer cells or esophageal cancer cells or lung cancer cells or breast cancer cells or ovarian cancer cells or stomach cancer cells or squamous cell carcinoma cells or AML cells or multiple myeloma cells or gastric cancer cells or liver cancer cells or brain cancer cells or Kaposi sarcoma cells or carcinoma mucoepidermoid cells or choriocarcinoma cells or fibrosarcoma cells or cervical carcinoma cells or glioma cells or adenocarcinoma cells or lung adenocarcinoma cells or non-small-cell lung carcinoma cells or bladder cancer cells or small cell lung cancer cells.

Also provided is a method for determining whether CD9-expressing cells, preferably CD9 positive tumor cells, are present in a sample comprising:
 contacting said sample with antibody AT14-012 optionally having one or more of the mutations H40Y, Y112F and D116H and/or light chain mutation T66I (IMGT numbering), or with a functional part or functional equivalent thereof, and
 allowing antibody AT14-012 optionally having one or more of the mutations H40Y, Y112F and D116H (IMGT numbering), or said functional part or functional equivalent thereof, to bind CD9-expressing cells, if present, and
 determining whether or not CD9-expressing cells, such as for instance CD9 positive tumor cells, are bound to antibody AT14-012 optionally having one or more of the mutations H40Y, Y112F and D116H and/or light chain mutation T66I (IMGT numbering), or to said functional part or functional equivalent thereof, thereby determining whether or not CD9-expressing cells are present in said sample.

Some embodiments provide a method according to the invention wherein said sample comprises a blood sample, or a bone marrow sample, or a biopsy. In some embodiments, said biopsy is from skin tissue, in order to test for melanoma and/or squamous cell carcinoma. In some embodiments, said biopsy is from the intestines, in order to test for gastric cancer, colorectal cancer, esophageal cancer or stomach cancer. In some embodiments, said biopsy is from pancreatic tissue, to test for pancreatic cancer, or from lung tissue, to test for lung cancer, or from breast tissue, to test for breast cancer, or from ovarian tissue, to test for ovarian cancer, or from liver tissue, to test for liver cancer, or from brain tissue, to test for brain cancer or from mucoepidermoid tissue to test for carcinoma mucoepidermoid, or from cervical tissue to test for cervical carcinoma, or from bladder tissue to test for bladder cancer. In some embodiments, said sample is a blood sample, which is for instance useful for testing for AML, multiple myeloma, cancer related extracellular vesicles (exosomes), or the presence of metastases of any of the above mentioned solid tumors.

The test results with a binding compound according to the invention are useful for typing of a sample. For instance, if a sample of an individual appears to contain malignant CD9-positive cells, the sample is typed as containing disease-associated cells. Such typing can subsequently be used for diagnosis of a disorder associated with CD9-expressing cells. Some embodiments therefore provide an antibody or functional part or functional equivalent according to the invention for use in diagnosis of a disorder associated with CD9-expressing cells. Said disorder is preferably selected from the group consisting of a CD9 positive cancer, arthritis, lung inflammation, COPD, colitis, and a disorder associated with innate lymphoid cells. Said CD9 positive cancer is preferably selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer. In some preferred embodiments, antibody AT14-012 optionally having one or more of the mutations H40Y, Y112F and D116H and/or light chain mutation T66I (IMGT numbering), or a functional part or functional equivalent is used for the above-mentioned detection and diagnosis. Also provided is therefore antibody AT14-012 optionally having one or more of the mutations H40Y, Y112F and D116H and/or light chain mutation T66I (IMGT numbering), or a functional part or functional equivalent thereof, for use in diagnosis of a disorder associated with CD9-expressing cells. Some embodiments provide antibody AT14-012 optionally having one or more of the mutations H40Y, Y112F and D116H and/or light chain mutation T66I (IMGT numbering), or a functional part or functional equivalent thereof, for use in diagnosis of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer or small cell lung cancer.

Also provided is an ex vivo method for determining whether an individual is suffering from a CD9-positive cancer, the method comprising:
  contacting tumor cells from said individual with an antibody or functional part or functional equivalent according to the invention,
  allowing said antibody or functional part or functional equivalent to bind CD9-expressing cells, if present, and
  determining whether or not CD9-expressing cells are bound to said antibody or functional part or functional equivalent, thereby determining whether or nor said individual is suffering from a CD9-positive cancer.

Non-limiting examples of such CD9-positive cancer are listed above. Preferably, antibody AT14-012 optionally having one or more of the mutations H40Y, Y112F and D116H and/or light chain mutation T66I (IMGT numbering) or a functional part or functional equivalent thereof is used for said method. Some embodiments therefore provide an ex vivo method for determining whether an individual is suffering from a CD9-positive cancer, the method comprising:
  contacting tumor cells from said individual with antibody AT14-012 optionally having one or more of the mutations H40Y, Y112F and D116H and/or light chain mutation T66I (IMGT numbering), or with a functional part or functional equivalent thereof,
  allowing said antibody or functional part or functional equivalent to bind CD9-expressing cells, if present, and
  determining whether or not CD9-expressing cells are bound to said antibody or functional part or functional equivalent, thereby determining whether or nor said individual is suffering from a CD9-positive cancer.

As shown in the Examples, antibody AT14-012 binds at least 5 CD9 amino acids located within positions 154-181, preferably 168-181, of the CD9 sequence as depicted in FIG. 2. Antibody AT14-012 binds a CD9 epitope that comprises CD9 amino acids corresponding to K169, D171, V172, L173 and F176 of the CD9 sequence as depicted in FIG. 2. In particular, AT14-012 binds to amino acids K169, D171, V172, L173 and F176 of this CD9 sequence. Now that this is known, it has become possible to obtain or generate further antibodies with specificity for CD9. As described herein before, this can for instance be done by immunizing a non-human animal with a CD9 peptide comprising at least 4, preferably at least 5, of the above mentioned amino acid residues, or with a CD9 peptide consisting of at least 4, preferably at least 5, of the above mentioned amino acid residues, or with an immunogenic compound comprising such CD9 peptide, or with a nucleic acid molecule or functional equivalent thereof encoding such CD9 peptide, preferably followed by one or more booster administrations. Subsequently, antibodies and/or B cells that are specific for CD9 can be harvested from said non-human animal in some embodiments, said antibody or B cell is tested for competition with antibody AT14-012 for binding to CD9.

Alternatively, or additionally, said CD9 peptide is used to screen a phage display library in order to identify and/or isolate CD9-specific immunoglobulins, typically Fab fragments. Obtained antibodies, B cells or Fab fragments will typically compete with antibody AT14-012 for binding to CD9. In some embodiments, a competition assay is performed.

The above mentioned CD9 peptides and uses thereof are also encompassed by the present invention. Some embodiments therefore provide an isolated, recombinant or purified CD9 peptide with a length of at most 60 amino acid residues, wherein said peptide comprises at least 5 amino acid residues that are identical to at least 5 amino acid residues located within CD9 amino acid positions 154-181, preferably amino acids positions 168-181, as depicted in FIG. 2. Some embodiments provide an isolated, recombinant or purified CD9 peptide with a length of at most 60 amino acid residues, wherein said peptide comprises at least 6 amino acid residues that are identical to at least 6 amino acid residues located within CD9 amino acid positions 154-181, preferably amino acids positions 168-181, as depicted in FIG. 2. In some embodiments said CD9 peptide comprises 5 or 6 amino acid residues that are identical to 5 or 6 amino acid residues located within CD9 amino acid positions 169-176 as depicted in FIG. 2. In some embodiments, said isolated, recombinant or purified CD9 peptide at least comprises amino acids corresponding to K169, D171, V172, L173 and F176 of the CD9 sequence as depicted in FIG. 2. In some embodiments, said isolated, recombinant or purified CD9 peptide at least comprises amino acids corresponding to K169, D171, V172, L173 and T175 of the CD9 sequence as depicted in FIG. 2. Preferably, said CD9 peptide further comprises an amino acid corresponding to F176 of the CD9 sequence as depicted in FIG. 2.

As used herein, any of the above-mentioned peptides are referred to as a "CD9 peptide according to the invention".

In some embodiments, a CD9 peptide according to the invention has a length of at most 55 amino acid residues. In some embodiments, a CD9 peptide according to the present invention has a length of at most 50 amino acid residues or at most 45 amino acid residues or at most 40 amino acid residues. In some embodiments, a CD9 peptide according to the present invention has a length of at most 35 amino acid residues or at most 30 amino acid residues or at most 25 amino acid residues or at most 20 amino acid residues or at most 15 amino acid residues. In some embodiments, said CD9 peptide according to the present invention has a length of 10 amino acid residues, or 9 amino acid residues or 8 amino acid residues.

Besides the recited amino acid residues that are identical to at least 6 amino acid residues located within positions 154-181 of the human CD9 protein as depicted in FIG. 2, preferably within positions 168-181 of said CD9 protein, a CD9 peptide according to the present invention may further comprise other amino acid residues. In some embodiments, said other amino acid residues are not derived from a human CD9 sequence. Said other amino acid residues, which are referred to as "non-CD9 amino acid residues" may for instance function to enhance stability, and/or to enhance immunogenicity, and/or to couple the CD9 peptide to another moiety such as for instance a molecular scaffold or carrier. Non-limiting examples of such scaffold or carriers are keyhole limpet hemocyanin and CLIPS scaffolds (such as for instance bis(bromomethyl)benzene, tris(bromomethyl)benzene and tetra(bromomethyl)benzene, described in WO 2004/077062). Some embodiments therefore provide an isolated, recombinant or purified CD9 peptide with a length of at most 60 amino acid residues, wherein said peptide comprises at least 5 amino acid residues that are identical to at least 5 amino acid residues located within CD9 amino acid positions 154-181, preferably amino acids positions 168-181, as depicted in FIG. 2. Preferably, said peptide comprises at least 6 amino acid residues that are identical to at least 6 amino acid residues located within CD9 amino acid positions 154-181, preferably amino acids positions 168-181, as depicted FIG. 2, preferably selected from the group consisting of K169, D171, V172, L173 and F176 of the CD9 sequence as depicted in FIG. 2, more preferably at least comprising K169, D171, V172, L173 and F176 of the CD9 sequence as depicted in FIG. 2, and wherein said peptide further comprises at least 1, or at least 2, or at least 3, or at least 4, or at least 5, or at least 10, or at least 20, or at least 30, or at least 40, or at least 50, non-CD9 amino acid residues, wherein the full length sequence of said non-CD9 amino acid residues is not present in the corresponding CD9 amino acid position as depicted in FIG. 2. Such peptide preferably comprises at least 6 amino acid residues that are identical to at least 6 amino acid residues located within CD9 amino acid positions 154-181, preferably amino acids positions 168-181, as depicted FIG. 2, preferably selected from the group consisting of K169, D171, V172, L173, T175 and F176 of the CD9 sequence as depicted in FIG. 2, more preferably at least comprising K169, D171, V172, L173, T175 and F176 of the CD9 sequence as depicted in FIG. 2. Such peptide is also embraced by the term "CD9 peptide according to the invention". Some embodiments provide an isolated, recombinant or purified CD9 peptide with a length of at most 60 amino acid residues, wherein said peptide comprises at least 5 amino acid residues that are identical to at least 6 amino acid residues located within CD9 amino acid positions 154-181 as depicted FIG. 2, preferably amino acid positions 168-181, preferably at least comprising K169, D171, V172, L173 and F176 of the CD9 sequence as depicted in FIG. 2, more preferably K169, D171, V172, L173, T715 and F176, that is coupled to another peptide containing non-CD9 amino acid residues. Some embodiments provide an isolated, recombinant or purified CD9 peptide with a length of at most 60 amino acid residues, wherein said peptide comprises at least K169, D171, V172, and L173 and T175 of the CD9 sequence as depicted in FIG. 2, and preferably also the F176 residue of the CD9 sequence as depicted in FIG. 2, wherein said peptide is coupled to another peptide containing non-CD9 amino acid residues. In some embodiments, said peptides are coupled to each other via a peptide bond. In other embodiments, said peptides are coupled to each other via another, non-peptide bond, such as for instance a linker.

As is known to the skilled person, once an immunogenic sequence has been provided, it has become possible to alter the sequence to some extent, thereby preferably optimizing the immunogenicity and/or stability of the resulting immunogen. This is for instance done by mutagenesis procedures where after the stability and/or immunogenicity of the resulting compounds are preferably tested and an improved CD9 antigenic compound is selected. A skilled person is well capable of generating antigen variants starting from a certain amino acid sequence. In some embodiments, a replacement net analysis is carried out, which involves replacement of one or more amino acid residues by any other amino acid residue, and testing the resulting compounds. In some preferred embodiments, conservative amino acid substitution is used. Examples of conservative amino acid substitutions include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. Another example of conservative amino acid substitutions includes the substitution of serine for threonine and tyrosine for phenylalanine.

Further provided is therefore an isolated, recombinant or purified CD9 peptide according to the invention wherein at least one amino acid residue selected from the group consisting of K169, D171, V172, L173, T175 and F176 of the CD9 sequence as depicted in FIG. 2 is substituted by another amino acid residue, wherein said peptide comprises an arginine at an amino acid position corresponding to K169 of the CD9 sequence depicted in FIG. 2, and/or a glutamic acid at an amino acid position corresponding to D171 of the CD9 sequence as depicted in FIG. 2, and/or an amino acid residue selected from the group consisting of isoleucine, leucine and methionine at an amino acid position corresponding to V172 of the CD9 sequence as depicted in FIG. 2, and/or an amino acid residue selected from the group consisting of isoleucine, valine and methionine at an amino acid position corresponding to L173 of the CD9 sequence as depicted in FIG. 2, and/or a serine at an amino acid position corresponding to T175 of the CD9 sequence as depicted in FIG. 2, and/or a tyrosine at an amino acid position corresponding to F176 of the CD9 sequence as depicted in FIG. 2.

In other words, CD9 peptides according to the invention are provided wherein the lysine at position 169 has been replaced by an arginine, and/or wherein the aspartic acid at position 171 has been replaced by a glutamic acid, and/or wherein the valine at position 172 has been replaced by an isoleucine, leucine or methionine, and/or wherein the leucine at position 173 has been replaced by isoleucine, valine or methionine, and/or wherein the phenylalanine at position 176 has been replaced by a tyrosine. These are conservative amino acid substitutions, so that the resulting peptides will still be able to bind antibody AT14-012. The resulting peptides will also be able to bind or generate antibodies or functional parts or functional equivalents thereof that compete with antibody AT14-012 for binding to CD9, preferably to the same epitope in CD9.

In some embodiments, the amino acid residues of a CD9 peptide according to the invention are chosen from the 20 amino acid residues that naturally occur in eukaryotes, which are also referred to as "standard" or "canonical" amino acids. Alternatively, non-natural amino acid residues are included in a CD9 peptide according to the invention, such as for instance D-amino acids (i.e. D-stereoisomers of amino acids) or N-methyl amino acids.

Nucleic acid molecules, or functional equivalents thereof, encoding a CD9 peptide according to the invention are also encompassed by the present invention. Further provided is therefore an isolated, synthetic or recombinant nucleic acid molecule, or a functional equivalent thereof, encoding a CD9 peptide according to the invention. Said nucleic acid molecule or functional equivalent preferably comprises a chain of nucleotides, more preferably DNA, cDNA or RNA. In other embodiments said nucleic acid molecule or functional equivalent comprises other kinds of nucleic acid structures such as for instance a DNA/RNA helix, peptide nucleic acid (PNA), locked nucleic acid (LNA) and/or a ribozyme.

Said nucleic acid molecules and functional equivalents are for instance useful for the production of a CD9 peptide according to the present invention, using a nucleic acid expression system such as for instance host cells like for instance E. coli, CHO, NSO or 293(T) cells. In some embodiments, said nucleic acid molecule or functional equivalent according to the invention is present in a gene delivery vehicle, which facilitates introduction of said nucleic acid molecule or functional equivalent into a cell of interest. Further provided is therefore a gene delivery vehicle, preferably a vector, comprising a nucleic acid molecule or functional equivalent according to the invention. A host cell comprising a nucleic acid molecule or functional equivalent according to the invention, and/or a gene delivery vehicle according to the invention, is also provided herewith.

As described above, a CD9 peptide according to the present invention, or a nucleic acid molecule or functional equivalent encoding for a CD9 peptide according to the invention is for instance useful for obtaining a CD9-specific antibody according to the invention, such as for instance an antibody that competes with antibody AT14-012 for binding to CD9. This is for instance done by immunizing a non-human animal with said CD9 peptide or with a (vector comprising) a nucleic acid molecule or functional equivalent encoding a CD9 peptide according to the invention. Alternatively, or additionally, a phage display library is screened. Some embodiments therefore provide a use of a CD9 peptide according to the invention, or a use of a nucleic acid molecule or functional equivalent according to the invention, or a use of a vector according to the invention, for producing, binding, detecting and/or obtaining an immune cell, such as for instance a B cell, and/or an antibody or a functional part or functional equivalent thereof, such as for instance a Fab fragment, that is specific for CD9. Said immune cell or antibody or functional part or functional equivalent thereof is preferably able to specifically bind melanoma cells. A CD9 peptide according to the invention for use as an immunogen is also herewith provided, as well as a nucleic acid molecule or functional equivalent encoding a CD9 peptide according to the invention for use as an immunogen.

Also provided is a method for producing a CD9-specific immune cell or a CD9-specific antibody, the method comprising immunizing a non-human animal with a CD9 peptide according to the invention or with a nucleic acid molecule or functional equivalent or vector according to the invention. Said method preferably further comprises harvesting an CD9-specific immune cell or antibody from said non-human animal. As said before, said immune cell or antibody or functional part or functional equivalent thereof is preferably able to specifically bind melanoma cells.

A CD9-specific antibody or functional part or functional equivalent thereof obtainable by a method according to the invention is also provided herewith, as well as an immune cell obtainable by a method according to the invention. Said CD9-specific antibody, functional part, functional equivalent or immune cell preferably competes with antibody AT14-012 for binding to CD9.

Said non-human animal preferably comprises a mammal such as a rodent or cattle. In some embodiments said non-human animal comprises a mouse, a rat, a rabbit, a llama, a camel, a pig, poultry, a cow, a goat, a horse, an ape, and/or a gorilla.

Some embodiments provide a composition, preferably an immunogenic composition, comprising a CD9 peptide according to the present invention. In some embodiments, said CD9 peptide is coupled to a pharmaceutically acceptable carrier or scaffold. Some embodiments provide a composition, preferably an immunogenic composition, comprising a nucleic acid molecule or functional equivalent thereof encoding a CD9 peptide according to the present invention. Some embodiments provide a composition, preferably an immunogenic composition, comprising a vector that comprises said nucleic acid molecule or functional equivalent thereof. An immunogenic composition according to the present invention preferably further comprises a biocompatible additive, such as for instance a carrier, diluent, excipient or filler. Some embodiments provide a vaccine comprising a CD9 peptide according to the invention, or a vaccine comprising a compound that comprises a CD9 peptide according to the invention, or a vaccine comprising a nucleic acid molecule or functional equivalent thereof encoding a CD9 peptide according to the invention. Some embodiments provide a composition according to the invention, wherein said composition is a pharmaceutical composition which further comprises a pharmaceutically acceptable carrier, diluent or excipient.

CD9 peptides according to the present invention are also useful for testing for the presence of CD9-specific binding compounds, such as for instance CD9-specific antibodies or CD9-specific immune cells such as B cells or T cells, in a biological sample. For instance, a sample from an individual, or a fraction of such sample that comprises antibodies, B cells and/or T cells, is incubated with a CD9 peptide according to the present invention, or with a compound that comprises a CD9 peptide according to the invention, in order to screen for the presence of CD9-specific antibodies and/or CD9-specific immune cells. If such antibodies or immune cells appear to be present in said sample or in said sample fraction, and to bind said CD9 peptide according to the present invention, said sample is typed as being positive for CD9-specific binding compounds (i.e. antibodies and/or immune cells).

A CD9-specific antibody or CD9-specific immune cell is for instance detected and/or quantified using an immunoassay, such as for instance a Western blot, a (capture) ELISA or RIA. These assays are well known in the art. Labelled CD9 peptides according to the invention (optionally in the context of an MHC complex in order to detect T cells) are for instance incubated with a blood sample or with a tissue sample such as for instance a skin sample, or with a fraction of such sample that comprises antibodies, B cells and/or T cells, where after unbound binding compounds are washed away. Subsequently, it is determined whether said labelled CD9 peptides according to the invention are bound by CD9-specific antibodies or immune cells. In some embodiments, an unlabeled CD9 peptide according to the invention, or an unlabeled compound comprising a CD9 peptide according to the invention (optionally in the context of an MHC complex), is contacted with a sample that comprises antibodies and/or immune cells, such as for instance a blood sample or tissue sample such as for instance a skin sample, or with a fraction of such sample that comprises antibodies, B cells and/or T cells. After incubation, one or more washing steps are preferably performed in order to remove non-bound antibodies and unbound immune cells. Subsequently, it is tested whether antibodies or immune cells have bound said CD9 peptide according to the invention, for instance using an antibody that is specifically directed against human antibodies or human immune cells and that is coupled to a marker, such as for instance a fluorescent compound or for instance horseradish peroxidase or alkaline phosphatase. After a further washing step, it is preferably determined whether the second antibody has bound, for instance by measuring light emission or by adding a substrate of horseradish peroxidase or alkaline phosphatase. These detection techniques are well known in the art.

In some embodiments, a CD9 peptide according to the invention, or a compound or composition that comprises a CD9 peptide according to the invention (optionally in the context of an MHC complex), is contacted with a fraction of a sample that has been enriched for antibodies and/or immune cells. In some embodiments, said fraction is an in vitro B cell culture or an in vitro T cell culture. In some embodiments, a CD9 peptide according to the invention or a compound or composition that comprises a CD9 peptide according to the invention is contacted with antibodies and/or immune cells that have been essentially purified from a biological sample, such as for instance a purified B cell fraction that has been obtained by selecting for CD19 positive cells and/or an antibody/B cell fraction that has been purified using an anti Ig antibody or a protein A or G purification method. Protein A or G purification methods are well known in the art and protocols and reagents are commercially available. As used herein, the term "immune cells that have been essentially purified from a sample" means that at least 80%, preferably at least 85%, more preferably at least 90% or at least 95%, of the cells of a resulting fraction consists of immune cells. The term "antibodies that have been essentially purified from a sample" means that at least 80%, more preferably at least 85%, more preferably at least 90% or at least 95%, of the mass of a resulting fraction consists of antibodies.

Further provided is therefore a use of a CD9 peptide according to the invention, or a use of a compound or composition that comprises a CD9 peptide according to the invention, for binding and/or detecting a CD9-specific immune cell and/or a CD9-specific antibody, or a functional part or functional equivalent thereof. Said immune cell and/or antibody or functional part or functional equivalent thereof is preferably able to specifically bind CD9-positive tumor cells, such as for instance melanoma cells. A CD9 peptide according to the invention, or a compound that comprises a CD9 peptide according to the invention, for use as a detection moiety for CD9-specific binding compounds such as antibodies and/or immune cells is also herewith provided, as well as a method for determining whether a sample comprises CD9-specific antibodies and/or CD9-specific immune cells, the method comprising incubating a CD9 peptide according to the invention, or a compound or composition that comprises a CD9 peptide according to the invention, with said sample, or with a fraction of said sample that comprises antibodies and/or immune cells, and subsequently determining whether said CD9 peptide according to the invention is bound by CD9-specific antibodies and/or by CD9-specific immune cells, or whether said compound that comprises said CD9 peptide according to the invention is bound by CD9-specific antibodies and/or CD9-specific immune cells. If such binding is detected, it is concluded that said sample comprises CD9-specific antibodies and/or CD9-specific immune cells, for instance antibodies and/or immune cells that are able to specifically bind CD9-positive tumor cells like melanoma.

Also provided is a method for determining whether a sample comprises CD9-specific antibodies and/or CD9-specific immune cells, the method comprising incubating a CD9 peptide according to the invention, or a compound that comprises a CD9 peptide according to the invention (optionally in the context of an MHC complex), with antibodies and/or immune cells that have been essentially purified from said sample, and subsequently determining whether said CD9 peptide according to the invention is bound by CD9-specific antibodies and/or CD9-specific immune cells, or whether said compound that comprises said CD9 peptide according to the invention is bound by CD9-specific antibodies and/or CD9-specific immune cells.

In some embodiments, the results of detection tests as described above are used for determining whether an individual has a disorder associated with CD9-expressing cells. For instance, if a sample from an individual that is tested for the presence of a CD9-positive tumor appears to contain CD9-specific immune cells and/or CD9-specific antibodies, it can be concluded that said individual is suffering from a CD9-positive tumor, like for instance melanoma. Said sample preferably comprises tumor cells. For instance, in order to test for the presence of melanoma cells, a biopsy of the skin area with the suspected melanoma is preferably used. Alternatively, or additionally, a blood sample or a lymph node sample is also useful for testing for CD9-positive tumor cells, because metastases often circulate in the blood and lymphatic system.

A CD9 peptide according to the invention for use as a diagnostic agent is therefore also provided herewith, as well as a compound or composition that comprises a CD9 peptide according to the invention for use as a diagnostic agent. Further provided is a use of a CD9 peptide according to the invention for diagnosing a disorder associated with CD9-expressing cells, such as for instance a CD9-positive tumor, or osteoporosis, or arthritis, or lung inflammation, or COPD, or colitis, or a disorder associated with innate lymphoid cells, as well as a use of a compound or composition that comprises a CD9 peptide according to the invention for diagnosing a disorder associated with CD9-expressing cells, such as for instance a CD9-positive tumor, or osteoporosis, or arthritis, or lung inflammation, or COPD, or colitis, or a disorder associated with innate lymphoid cells. In some embodiments, said CD9-positive cancer is melanoma. Some embodiments therefore provide a CD9 peptide according to the invention for use in diagnosing melanoma, as well as a use of a CD9 peptide according to the invention for the preparation of a diagnostic kit for diagnosing melanoma.

Further provided is a diagnostic kit comprising:
  a CD9 peptide according to the invention, or a compound or composition that comprises a CD9 peptide according to the invention, and
  means for detecting an antibody-bound CD9 peptide or an immune cell-bound CD9 peptide.

Such means for instance encompass labelled antibodies that are specifically directed against human antibodies or human immune cells. In some embodiments, said labelled antibodies are conjugated with horseradish peroxidase or alkaline phosphatase.

Some embodiments provide a method for determining whether an individual has a CD9-positive tumor, the method comprising contacting a CD9 peptide according to the invention, or a compound or composition that comprises a CD9 peptide according to the invention (optionally in the context of an MHC complex), with antibodies and/or immune cells of said individual and determining whether said CD9 peptide according to the invention, or said compound or composition comprising a CD9 peptide according to the invention, is bound by at least one of said antibodies and/or immune cells of said individual. If said CD9 peptide or said compound according to the invention is bound by antibodies and/or immune cells of said individual, it is concluded that said individual has a CD9-positive tumor. In some embodiments, said CD9-positive tumor is melanoma. In some embodiments, a CD9 peptide according to the invention, or a compound that comprises a CD9 peptide according to the invention, is contacted with a sample that comprises antibodies and/or immune cells of said individual, such as for instance a blood sample or a bone marrow sample or a biopsy such as for instance a skin tissue. In other embodiments, a CD9 peptide or compound according to the invention is contacted with a fraction of a sample from said individual, wherein said fraction comprises immune cells and/or antibodies. In some embodiments, a CD9 peptide or compound according to the invention is contacted with antibodies and/or immune cells that have been essentially purified from said sample, such as for instance a purified B cell fraction that has been obtained by selecting for CD19 positive cells and/or an antibody/B cell fraction that has been purified using an anti Ig antibody or a protein A or G purification method.

Another interesting application of the novel CD9 peptides according to the present invention and nucleic acid molecules and functional equivalents encoding therefore is immunotherapy. For instance, a CD9 peptide according to the present invention, or a nucleic acid molecule or functional equivalent encoding therefore, is used for treatment of a CD9-positive tumor. As used herein, "treatment" encompasses alleviation of at least one symptom, and/or delaying or even halting the progression of disease, at least temporarily. In one preferred embodiment, a CD9 peptide according to the invention, or a nucleic acid molecule or a functional equivalent encoding therefore, or a compound or composition that comprises a CD9 peptide according to the invention, is administered to a CD9-positive cancer patient in order to boost his/her immune system, resulting in an enhanced immune response. In some embodiments, naïve T cells or B cells from a CD9-positive cancer patient are cultured ex vivo and incubated with a CD9 peptide or compound according to the invention, optionally in the context of an MHC complex in case of a T cell culture, in order to obtain CD9-specific T cells or B cells that are subsequently administered to the patient, optionally after ex vivo expansion. In some embodiments, said CD9-positive cancer is melanoma.

In some embodiments, adoptive cell therapy is used. T cells from a CD9-positive cancer patient are preferably tested for binding or activation, using a CD9 peptide according to the invention in the context of an MHC complex or using a compound or composition that comprises a CD9 peptide according to the invention in the context of an MHC complex. T cells recognizing said CD9 peptide are expanded ex vivo and subsequently administered to the patient, which will result in an anti-CD9 T cell response.

In some embodiments, adoptive cell therapy of donor lymphocytes is used. Donor T cells isolated from a CD9-positive cancer patient who received allogeneic HSCT or isolated from the HSCT donor are preferably tested for CD9 binding or activation, using a CD9 peptide in the context of an MHC complex, or a compound that comprises a CD9 peptide according to the invention in the context of an MHC complex, and donor T cells recognizing said CD9 peptide are expanded ex vivo and subsequently administered to the patient, which will result in an anti-CD9 allogeneic T cell response.

In some embodiments, T cells are modified in order to provide them with a CD9-specific binding moiety. Said T cells are preferably derived from a CD9-positive cancer patient. In some embodiments, chimeric antigen receptor (CAR) T cells are produced. These are T cells with modified T cell receptors, which have been provided with a binding specificity of interest, preferably derived from an antibody. Typically, CAR T cells are produced by fusing a single-chain variable domains (scFv) derived from a monoclonal antibody to the CD3-zeta transmembrane domain, so that a zeta signal will be elicited upon target recognition by the scFv.

According to some embodiments, a CD9 peptide according to the invention, or a nucleic acid molecule or a functional equivalent encoding therefore, or a compound or composition that comprises a CD9 peptide according to the invention, is used in order to produce and/or isolate a CD9-specific antibody and/or B cell, which in turn is used for the production of a modified T cell. For instance, said CD9 peptide or compound or nucleic acid molecule or functional equivalent is used in order to elicit, detect and/or isolate a CD9-specific antibody or B cell. Subsequently, in some embodiments the heavy chain and/or light chain variable domains of said CD9-specific antibody are provided to T cells, thereby producing modified T cells with CD9 specificity. In some embodiments, these modified T cells are subsequently administered to a CD9-positive cancer patient, which will result in a tumor-specific T cell response. In some embodiments, said modified T cells are CAR T cells. In some embodiments said CD9-specific antibodies or B cells are tested for competition with antibody AT14-012 for binding to CD9 before the heavy chain and/or light chain variable domains of said antibodies are provided to T cells. Such competing antibodies are preferably selected for producing modified T cells with a CD9 specificity.

Further provided is therefore a CD9 peptide according to the invention, or a compound or composition that comprises a CD9 peptide according to the invention, or a nucleic acid molecule or functional equivalent thereof encoding a CD9 peptide according to the invention, for use as a medicament. Also provided is a use of a CD9 peptide according to the invention (optionally in the context of an MHC complex), or use of a compound or composition that comprises a CD9 peptide according to the invention (optionally in the context of an MHC complex), or use of a nucleic acid molecule or functional equivalent thereof encoding said CD9 peptide according to the invention, for the production of CD9-specific T cells. Some embodiments provide a method for producing a modified T cell, the method comprising contacting an antibody-containing sample or a B cell-containing sample from a CD9-positive cancer patient with a CD9 peptide or compound according to the invention, resulting in bound antibodies or B cells against CD9, and subsequently obtaining one or more CD9-specific domains from said CD9-specific antibodies or B cells and providing said one or more domains to a T cell. Some embodiments provide a method for producing a modified T cell, the method comprising immunizing a non-human animal with a CD9 peptide or compound or nucleic acid molecule or functional equivalent according to the invention, thereby eliciting an immune response against CD9, and subsequently obtaining one or more CD9-specific domains from a CD9-specific antibody or CD9-specific B cell from said non-human animal, or obtaining one or more nucleic acid sequences encoding for said one or more CD9-specific domains, and providing said one or more domains, or said one or more nucleic acid sequences, to a T cell.

A CD9 peptide according to the invention for use in immunotherapy is also provided herewith, as well as a nucleic acid molecule or functional equivalent thereof encoding a CD9 peptide according to the invention for use in immunotherapy. A compound or composition comprising a CD9 peptide according to the invention for use in immunotherapy is also provided herewith. Some embodiments provide a use of a CD9 peptide according to the invention, or a use of a compound or composition that comprises a CD9 peptide according to the invention, or a use of a nucleic acid molecule or functional equivalent thereof encoding a CD9 peptide according to the invention, for the preparation of a medicament against a disorder associated with CD9-expressing cells, such as for instance a CD9-positive tumor, or osteoporosis, or arthritis, or lung inflammation, or COPD, or colitis, or a disorder associated with innate lymphoid cells. In some embodiments, said CD9-positive tumor is selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

In some embodiments, the results of detection tests according to the invention as described hereinbefore are used for determining whether an individual exhibits a detectable immune response against a CD9-positive tumor like for instance melanoma. This is for instance preferred for determining whether a patient suffering from such tumor who has received immunotherapy, has elicited an anti-tumor immune response. Some embodiments therefore provide a method for determining whether an individual exhibits an immune response against a CD9-positive tumor, the method comprising contacting a CD9 peptide according to the invention (optionally in the context of an MHC complex), or a compound or composition that comprises said CD9 peptide according to the invention, with antibodies and/or immune cells of said individual and determining whether said CD9 peptide according to the invention, or said compound or composition that comprises said CD9 peptide according to the invention, is bound by at least one of said antibodies and/or immune cells of said individual. If said CD9 peptide or said compound appears to be bound, it indicates that said individual exhibits an immune response against a CD9-positive tumor.

In some embodiments, an isolated, recombinant or purified antibody, or a functional part or a functional equivalent thereof, that competes with antibody AT14-012 for binding to CD9 is used for treatment of melanoma. As described in the Examples, antibody AT14-012 was obtained from a melanoma patient in complete remission, demonstrating that AT14-012 is effective against melanoma. Antibodies that compete with AT14-012 for CD9 will therefore also be effective. Hence, administration of such antibodies to a melanoma patient will effectively counteract, and/or kill, melanoma cells. Some embodiments therefore provide an isolated, recombinant or purified antibody, or a functional part or a functional equivalent thereof, that competes with antibody AT14-012 for binding to CD9, for use as a medicament. Some embodiments provide a use of an isolated, recombinant or purified antibody, or a functional part or a functional equivalent thereof, that competes with antibody AT14-012 for binding to Cd9, for the preparation of a medicament.

Also provided is an isolated, recombinant or purified antibody, or a functional part or a functional equivalent thereof, that competes with antibody AT14-012 for binding to CD9, for use in a method for at least in part treating or preventing melanoma, as well as a use of an isolated, recombinant or purified antibody, or a functional part or a functional equivalent thereof, that competes with antibody AT14-012 for binding to CD9, for the preparation of a medicament against melanoma.

While the current application may describe features as part of the same embodiment or as parts of separate embodiments, the scope of the present invention also includes embodiments comprising any combination of all or some of the features described herein.

The invention is further explained in the following examples. These examples do not limit the scope of the invention, but merely serve to clarify the invention.

FIG. (1a). Schematic representation of human tetraspanin CD9

Tetraspanins are characterized by four spanning transmembrane regions and two extracellular loops: small extracellular loop 1 (EC1) and large extracellular loop 2 (EC2). The EC2 of CD9 is structurally and conformationally defined by two cysteine bonds (C152-C181 and C153-C167) and conserved adjacent residues (G154 and P168). Two highly variable regions among tetraspanin family members are located between amino acid positions 154-167 and 168-181.

FIG. (1b). Cartoon representation of the second extracellular loop.

Figure 5A:
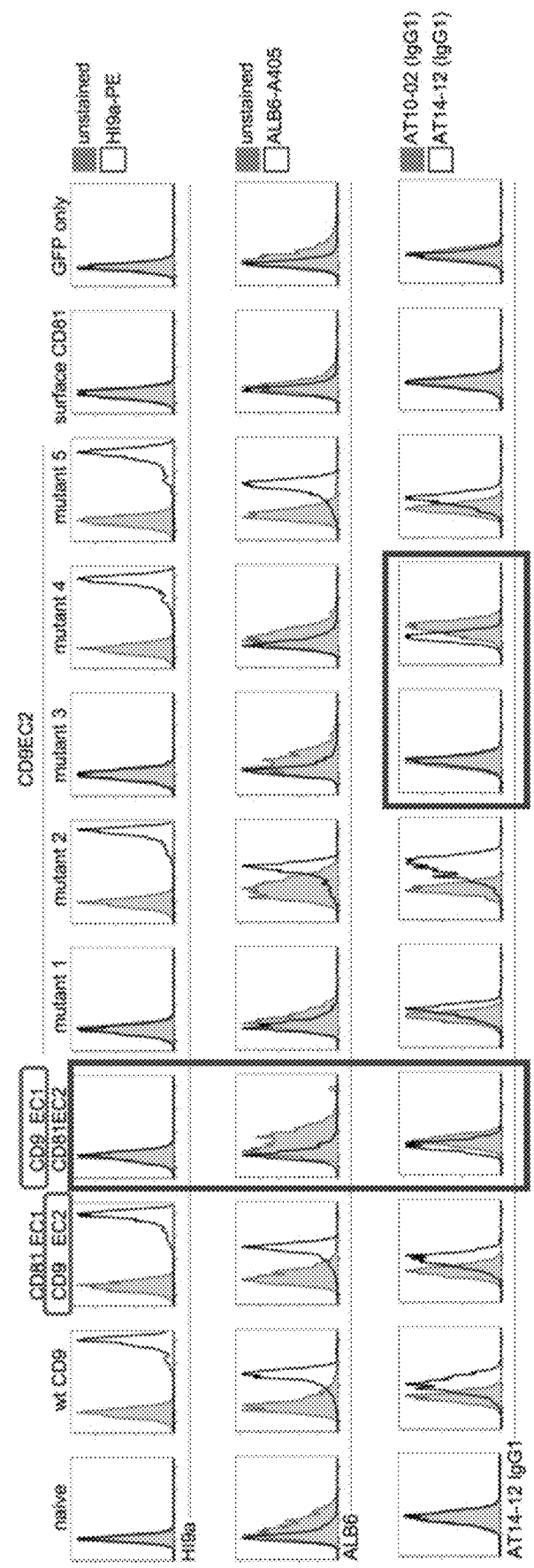

A cartoon representation of the second extracellular loop divided in 5 different regions and shown with corresponding amino acid numbers. These regions are chosen based on overlap with other tetraspanin family members such as CD81. These regions are further described in the epitope mapping studies (FIG. 5).

FIG. 2. Amino acid sequence of human CD9 (UniProt No. P21926)

FIG. 3. Amino acid and nucleotide sequences of antibody AT14-012. The CDR numbering is according to Kabat et al (1991).

FIG. 4. Target ID

FIG. (4a). AT14-012 reacts with an antigen of ~25 kDa size.

Western blots were probed for binding of AT14-012 towards lysates (50 ug) of Caco2, MelBLM and control HL-60 cell lines under non-reducing and reducing conditions (see Materials & Methods of Example 2). AT14-012 shows reactivity of towards a ~25 kDa size antigen and is lost when the samples are reduced, implying AT14-012 reacts towards a conformational epitope.

FIG. (4b). Mass spectrometric analysis of immunoprecipitation with AT14-012 on cancer cell lines indicates CD9 as the target.

Sortase biotin labeled AT14-012 or control AT10-002 were incubated with lysates of Caco2, MelBLM or control HL-60. Immunoprecipitated eluates were run on gel and stained with coommassie blue to reveal a visible band of ~25 kDa in size overlapping with western blot results. Mass spectrometric analysis revealed CD9 as the AT14-012 antigen. MS analysis identified precipitated CD9 for the Mel-BLM cell line as well whereas no CD9 was found for HL-60 eluates.

FIG. (4c). Confirmation of CD9 by commercial antibody ALB6.

IP eluates showed reactivity towards AT14-012 and anti-CD9 antibody ALB6 confirming CD9 to be the target antigen of AT14-012 whereas no reactivity was found for IP eluates of HL-60 lysates.

FIG. 5. Epitope mapping

FIG. (5a). Epitope mapping by hybrid or swapped mutants reveals extracellular loop 2 (EC2) and more specific region 154-180 as the main epitope for AT14-012.

Epitope mapping revealed the extracellular loop 2 to have epitopes of all anti-CD9 antibodies. AT14-012 showed loss of binding towards the variable CD9 loops m3 and m4.

FIG. (5b). Epitope mapping by alanine scanning of region m4 of the EC2.

Reactivity of HI9a, ALB6 and AT14-012 (-Alexa647 labeled) towards alanine mutants of region m4. HI9a was taken along as positive control. F176 was the only residue that showed loss of binding towards both antibodies. The additional 5 residues showed loss of binding towards AT14-012 (K169, D171, V172, L173 and T175).

FIG. 6. Tumor binding.

FIG. (6a). AT14-012 has broad binding reactivity against solid tumors. Flow cytometry analysis of AT14-012 versus AT10-002 antibody binding to a panel of solid tumor cell lines.

FIG. (6b). AT14-012 binds a selected number of Acute Myeloid Leukemia cell lines. Flow cytometry analysis of AT14-012 versus CD30 antibody binding to a panel of AML cell lines.

FIG. (6c). AT14-012 binds a selected number of Multiple Myeloma cell lines. Flow cytometry analysis of CD9 versus unstained and AT14-012 versus AT10-002 antibody binding to a panel of MM cell lines.

FIG. 7. Binding to healthy cells

Figure 7A:
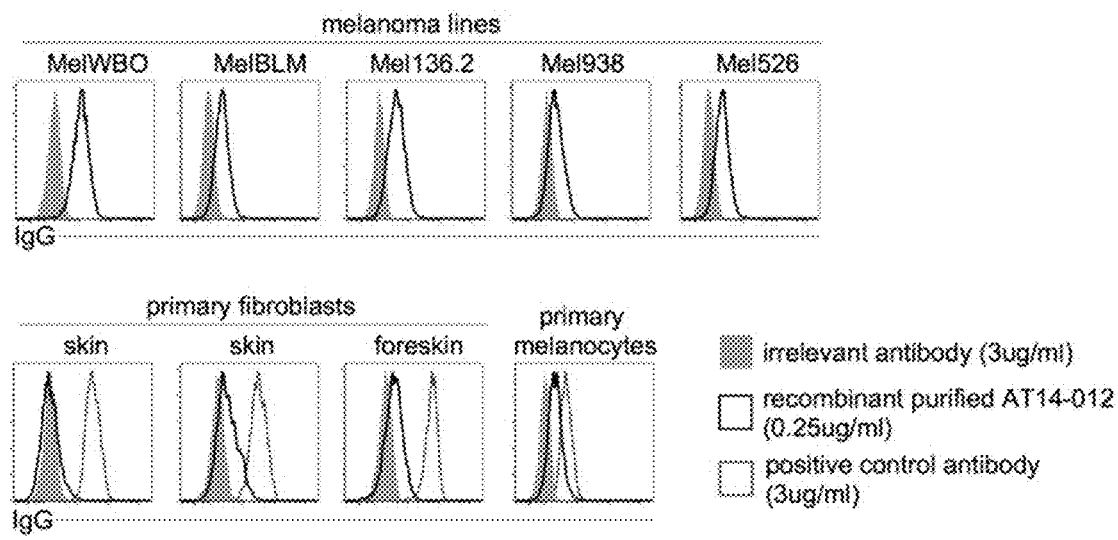

FIG. 7a. AT14-012 binds stronger to melanoma as compared to primary melanocytes. Analysis for AT14-012 binding to melanoma cell lines and primary melanocytes. AT10-002 (anti Influenza) was included as a negative control, Panitumumab (anti EGFR1) as a positive control for binding to healthy cells. After staining with the primary antibody, the cells were labelled with anti IgG-PE for visualization by flow cytometry.

Figure 7B:
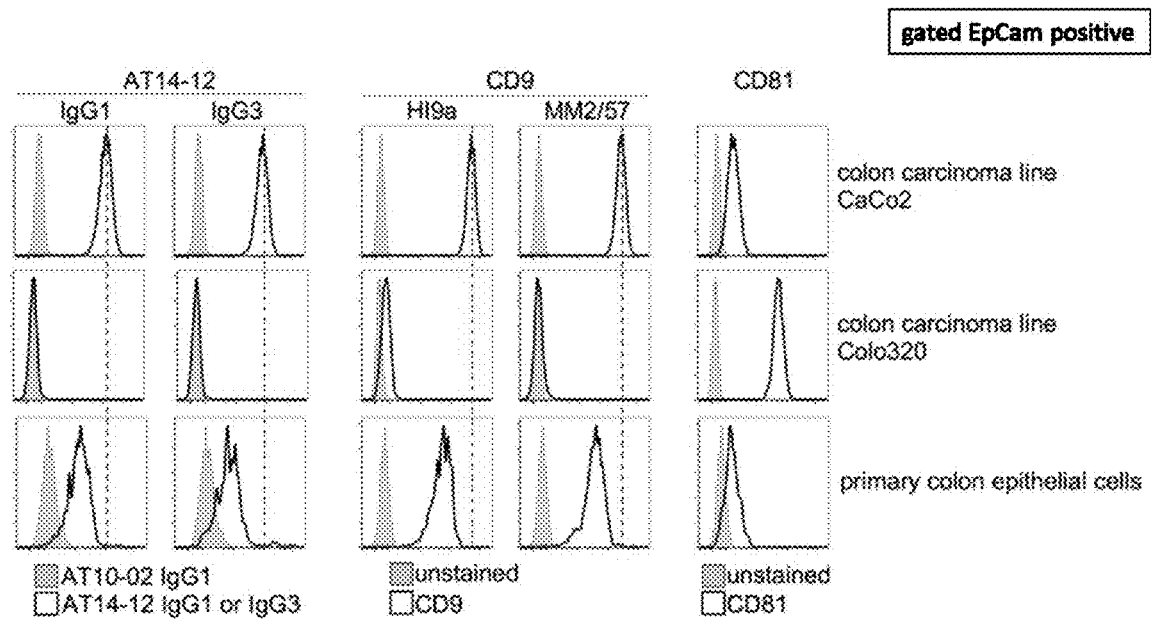

FIG. 7b. AT14-012 binds stronger to colon carcinoma as compared to primary colon epithelial cells. Flow cytometry analysis for CD9 PE and AT14-012 A647 binding to colon carcinoma cell lines and primary colon epithelial cells. AT10-002 A647 (anti Influenza) was included as a negative control, anti CD81 PE was included to confirm absence of CD9 expression on the Colo-320 cells.

Figure 7C:
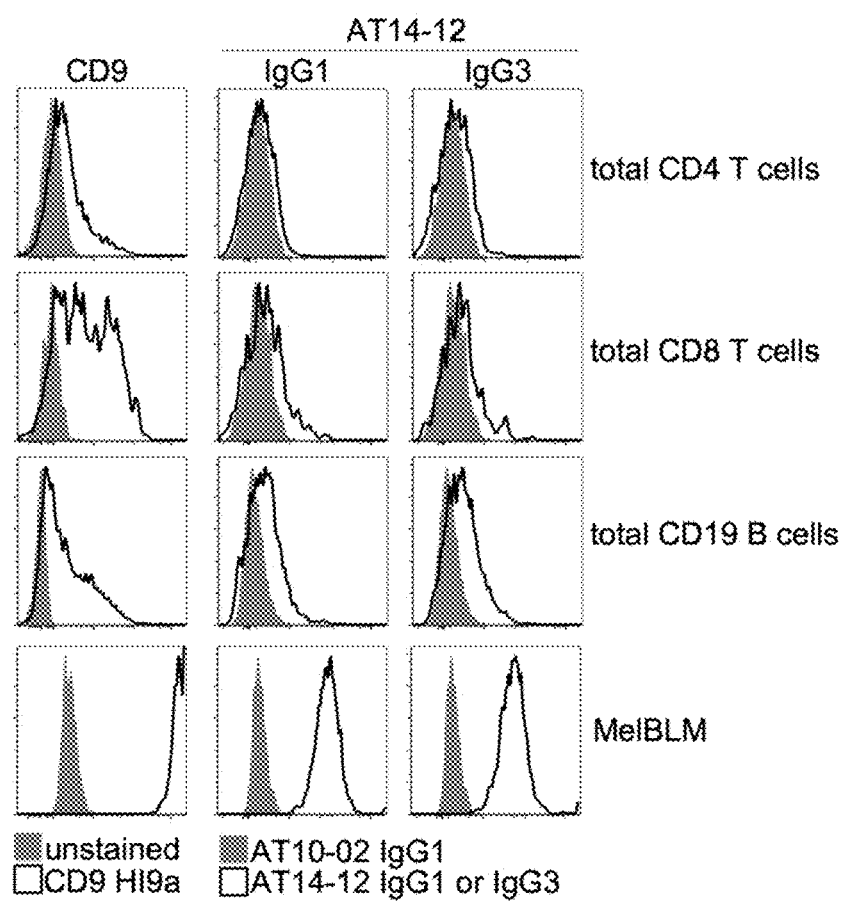

FIG. 7c. AT14-012 binds stronger to melanoma compared to primary tonsil lymphocytes. Tonsillar lymphocytes were stained with antibodies against CD4, CD8 and, CD9 to discriminate CD4 T, CD8 T and CD19 B cells respectively.

FIG. 8. Platelets

Figure 8A:
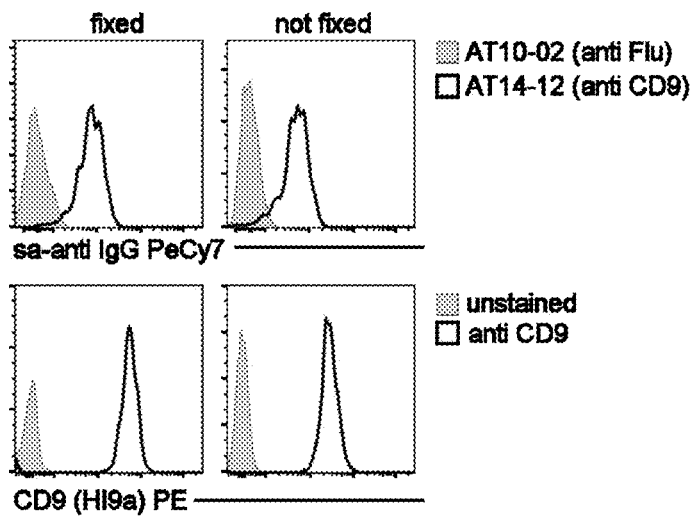

FIG. 8a AT14-012 binds human platelets. Fixed or non-fixed healthy human platelets were stained with CD41, CD9 or AT14-012 biotin/SA-PeCy7. Histograms are gated CD41 positive.

Figure 8B:
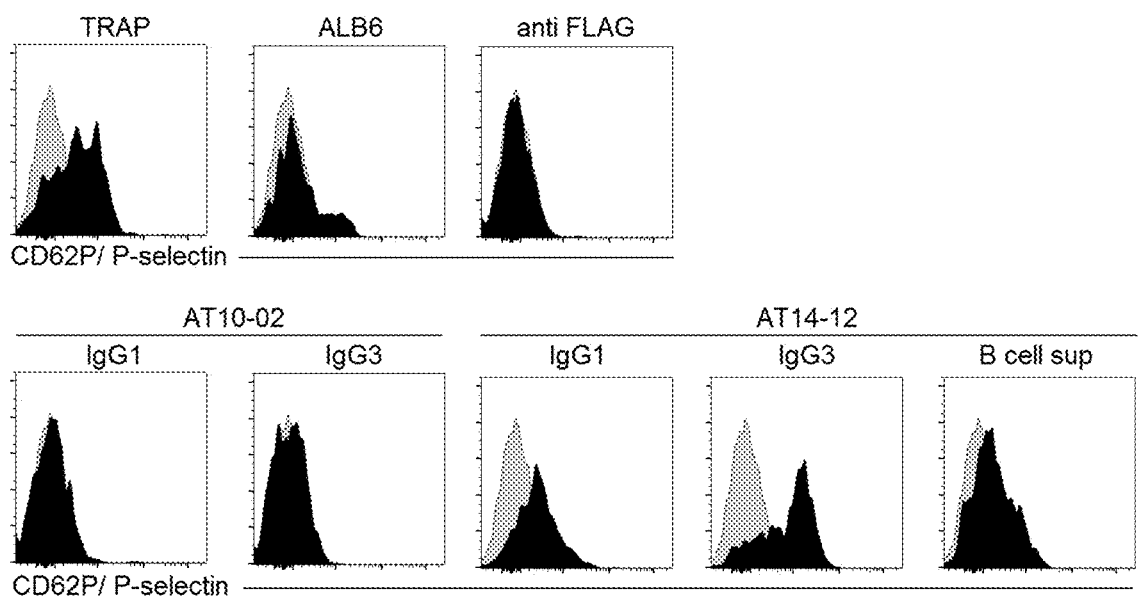

FIG. 8b AT14-012 activates healthy platelets. Surface CD62P expression was determined by flow cytometry on PRP incubated with TRAP (positive control peptide), ALB6 (positive control mouse IgG1 antibody), FLAG (negative control mouse IgG1 antibody), AT10-002 or AT14-012 antibodies.

Figure 8C:
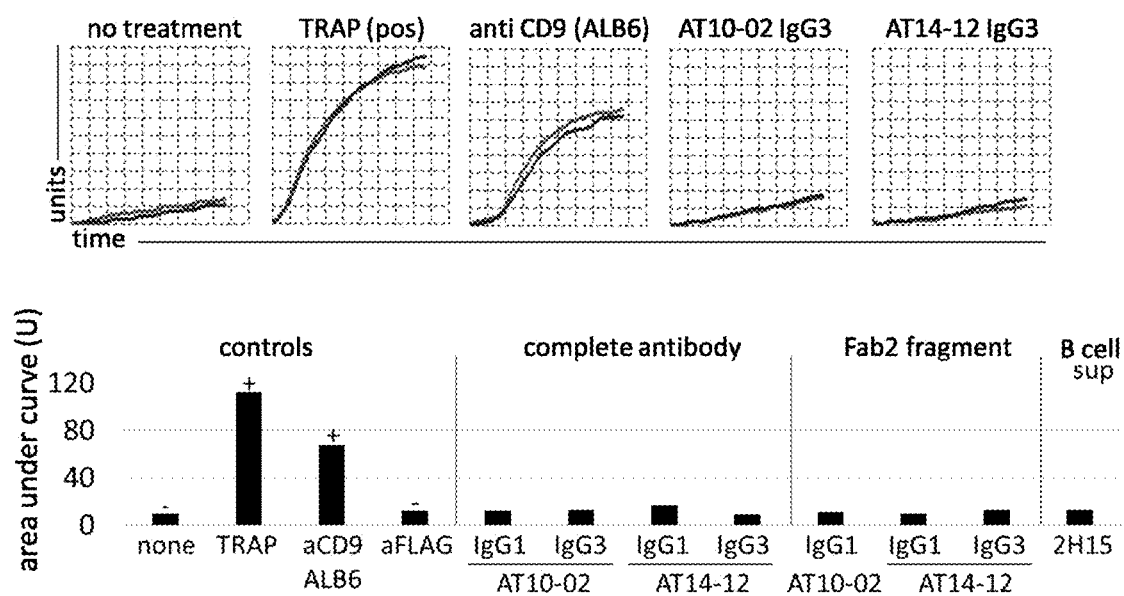

FIG. 8c. AT14-012 does not induce platelet aggregation. Whole blood was incubated with various stimuli and tested for the induction of platelet aggregation as measured using a Multiplate reader.

FIG. 9. In vivo experiments

Figure 9A:
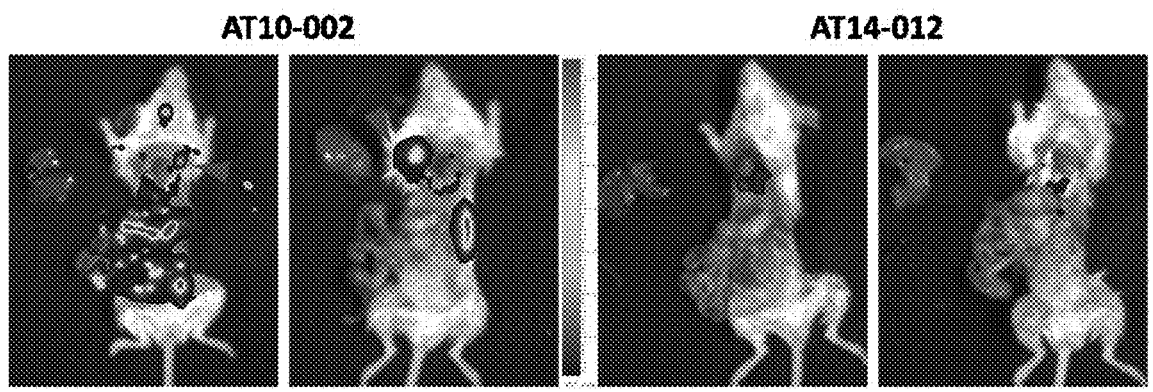

FIG. 9a AT14-012 inhibits lymph node metastasis in vivo. NSG mice subcutaneously grafted with 500.000 MelBLM GFP/luciferase melanoma cells on both flanks are treated with AT14-012 or AT10-002 control antibody. Lymph nodes metastasis indicated by the arrows were visualized using a Bioluminescence imager after luciferin injection and subsequent exposure of internal organs.

Figure 9B:
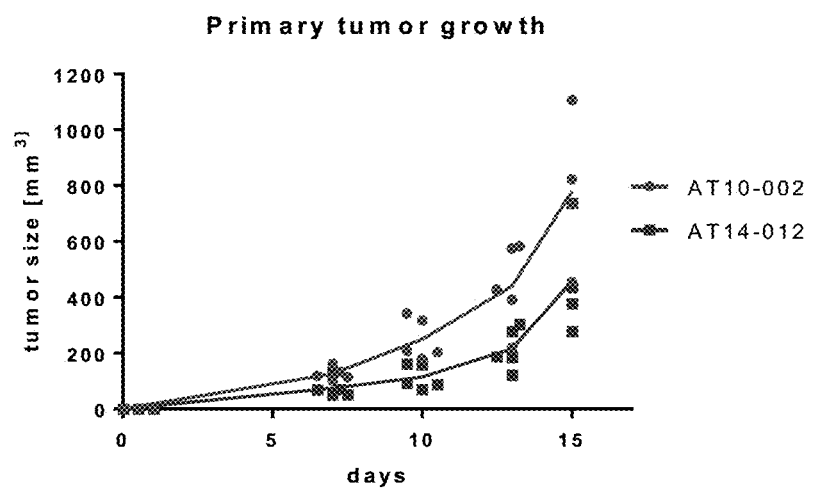

FIG. 9b AT14-012 impairs primary melanoma tumor growth in vivo. NSG mice subcutaneously grafted with 200.000 MelBLM GFP/luciferase melanoma cells on both flanks are treated with AT14-012 or AT10-002 control antibody from the start of the experiment. Tumor growth is determined by caliper measurement.

Figure 9C:
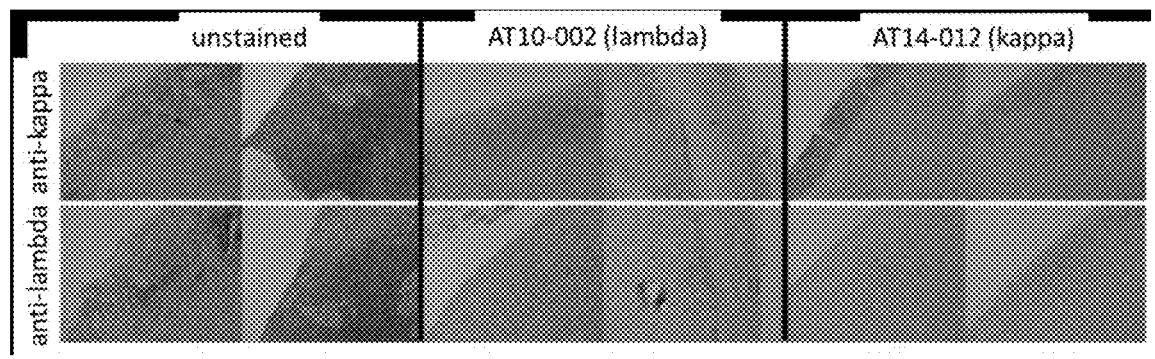

FIG. 9C AT14-012 recognizes melanoma tumors in vivo. MelBLM subcutaneous tumors harvested from NSG mice treated with either AT10-002 (anti Influenza) or AT14-012 or we left untreated were embedded in paraffin. For immunohistochemistry sections were stained with HRP labelled anti-lambda or anti-kappa antibodies.

Figure 9D:
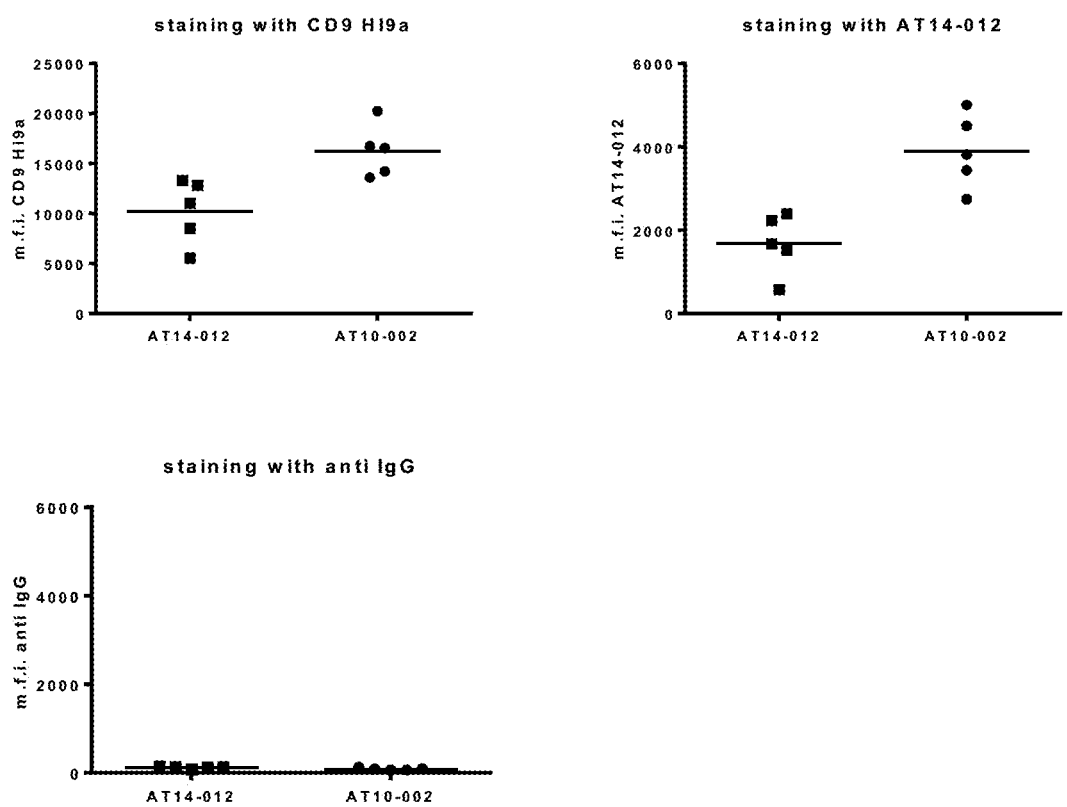

FIG. 9D Reduced surface CD9 levels after AT14-012 treatment. Subcutaneous MelBLM tumors harvested from NSG mice treated with AT14-012 or AT10-002 control antibody were digested and stained for flowcytometry with AT10-002-biotin, AT14-012-biotin followed by fluorescent labelled conjugated streptavidin, or direct labelled HI9a CD9 or anti IgG antibodies. Samples were measured on a Fortessa X20 (Becton Dickinson).

FIG. 9E-G AT14-012 impairs growth of SK-MEL-5 melanoma. NSG mice carrying subcutaneous SK-MEL-5 melanoma tumor are treated with AT14-012 or the AT10-002 control antibody. E. Tumor growth in time is determined by caliper measurement. Grey area indicates period of antibody treatment. F. Ex vivo isolated tumors are weighed. Weights are averaged per mouse. G. Tumors are digested by liberase treatment and stained for flowcytometry with CD9 HI9a-PE.

FIG. 10. AT14-012 binding correlates with CD9 expression on recently established tumor cell lines. Flowcytometry analysis for AT14-012 and CD9 HI9 binding to short term cultured melanoma cells. A. Histograms for the CD9 HI9a, AT14-012 and AT10-002 anti-Influenza (control) antibody staining of melanoma cells. B. Mean fluorescence intensities of the AT14-012 versus CD9 HI9a signals corrected for background staining Arrows indicate melanoma samples Mel06.07 and Mel05.18 derived from the original AT14-012 patient. C. Flowcytometry analysis for AT14-012 and CD9 HI9a binding to established cell lines (PANC01 and CAPAN2) and recent patient derived pancreas carcinoma tumor cells (53M and 193).

Figure 11A:
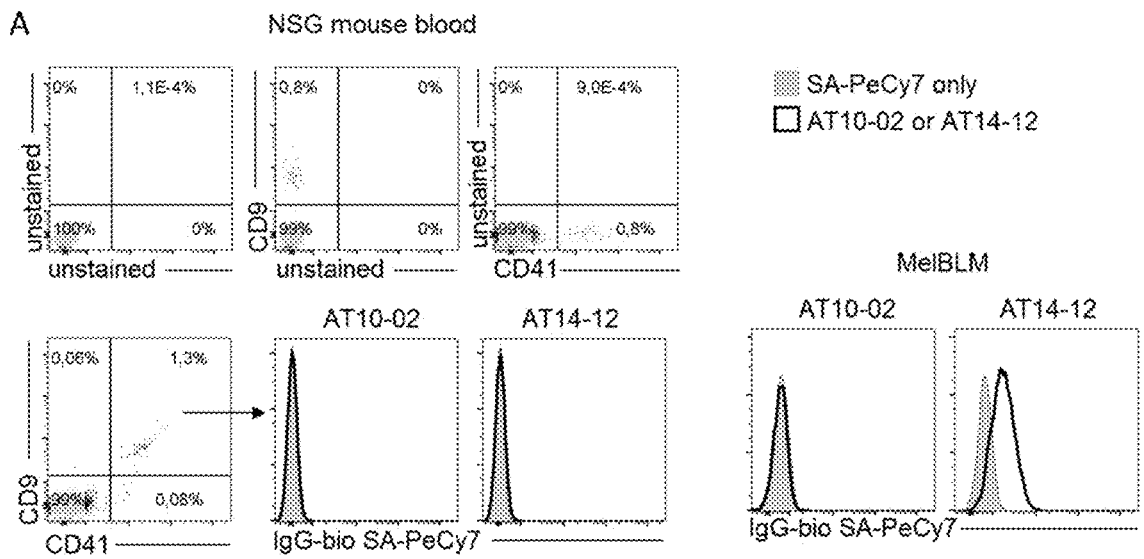
Figure 11B:
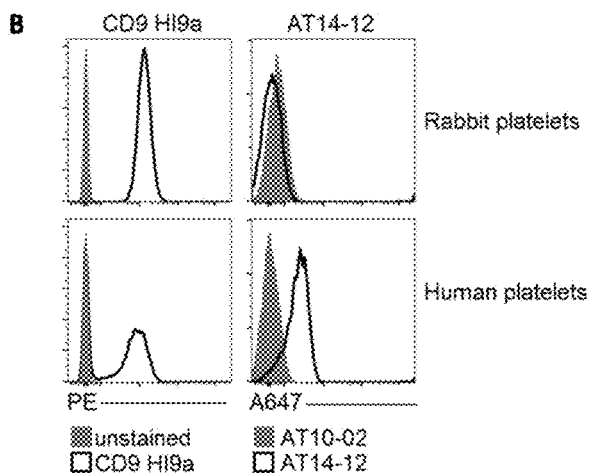
Figure 11C:
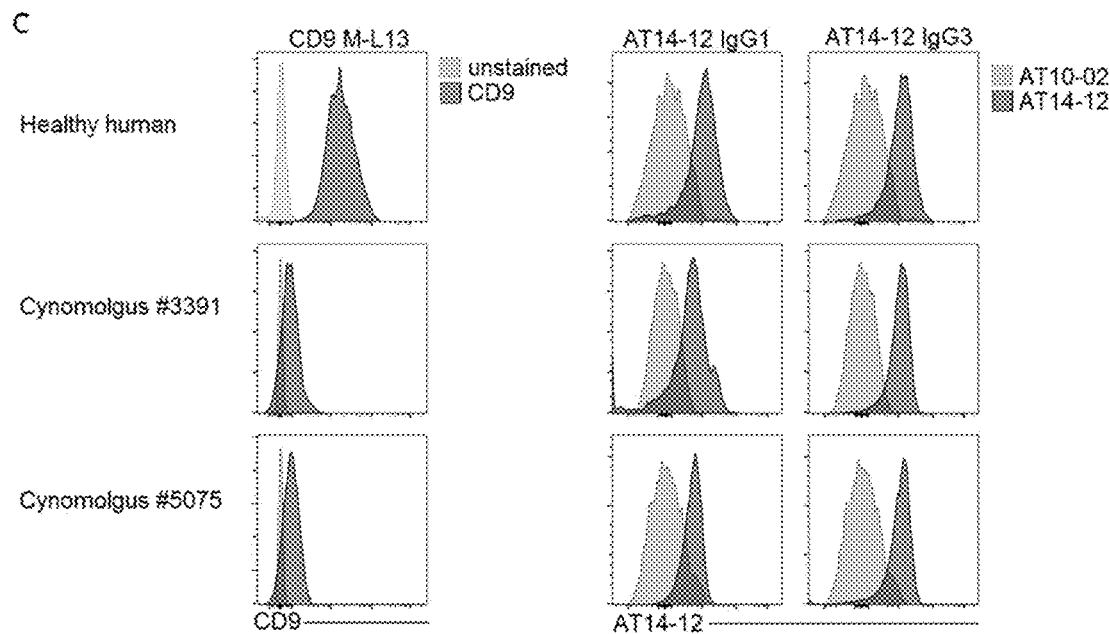

FIG. 11. AT14-012 binding is restricted to (non)-human primates. Platelet rich plasma isolated from A. NOD SCID γc-/- (NSG) mice; B. New Zealand White rabbits; C.

crab-eating macaque (cynomolgus monkeys) and a human was electronically gated for CD41 expressing platelets. Binding of AT10-002, AT14-012 and anti CD9 to platelets of the respective species was determined by flowcytometry.

FIG. 12. Antibody dependent cytotoxicity (ADCC). Chromium labeled A. MelBLM or Human Artery Endothelial Cells or B. primary short term cultured melanoma cells incubated with indicated antibodies were titrated against total human PBMCs. Cell death was determined by the release of Chromium in the supernatant.

Figure 13:
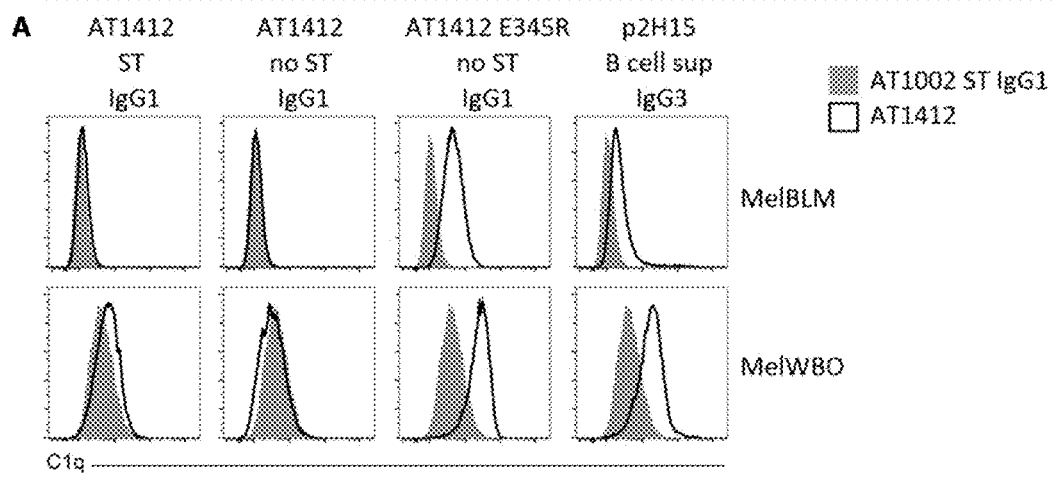
Figure 13B:
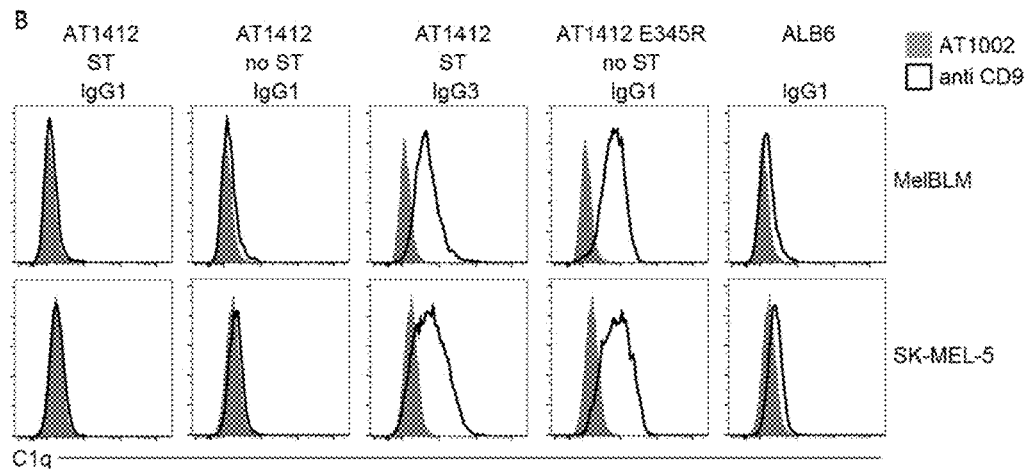

FIG. 13. AT14-012 triggers complement mediated tumor cell death. A, B. Melanoma cell lines are incubated with indicated antibodies and human serum and subsequently tested for C1q deposition by flow cytometry using an anti C1q antibody. Complement mediated cytotoxicity was determined by incubating C. suspension or D. overnight adhered melanoma cells with indicated antibodies and rabbit complement. E. Incubation of CD55 positive (MelBLM) and CD55 negative (Colo-205) with indicated antibodies and human serum. Percentage cell death of suspension of adhered cells is determined by DAPI by flow cytometry or TO-PRO3 by microscopy respectively.

Figure 14A:
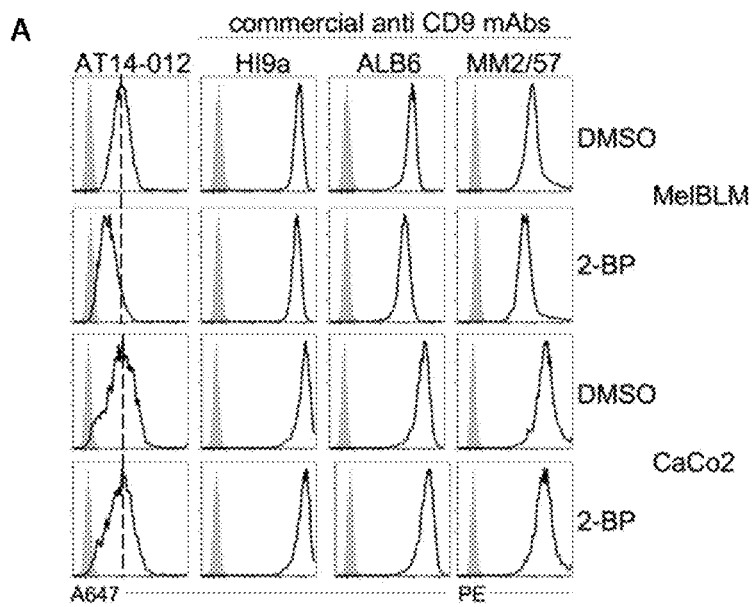
Figure 14B:
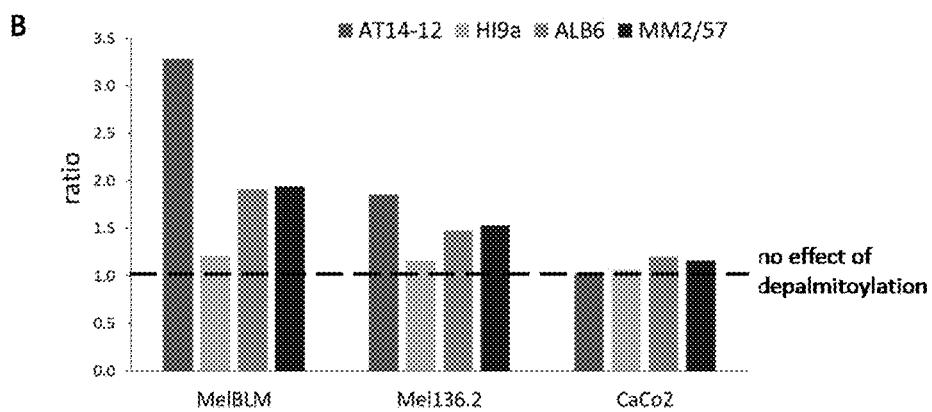

FIG. 14. AT14-012 favors binding to homoclustered CD9. Two melanoma and one colon carcinoma cell line were incubated with the inhibitor of palmitoylation 2-BP or DMSO only for 36 hours. A. Cells were detached and stained for flow cytometry with the AT10-002 influenza control antibody or different CD9 antibodies, AT14-012 or the commercially available HI9a and ALB6 clones. B. Mean fluorescence intensity of the histograms of the AT10-002 signals are deducted from the m.f.i. of the CD9 signals. Ratio is the Δm.f.i. values for the DMSO conditions divided over the corresponding Δm.f.i. 2-BP values and plotted against the different cell lines. A ratio of 1 indicates that antibody binding is not affected by de-palmitoylation.

Figure 15:
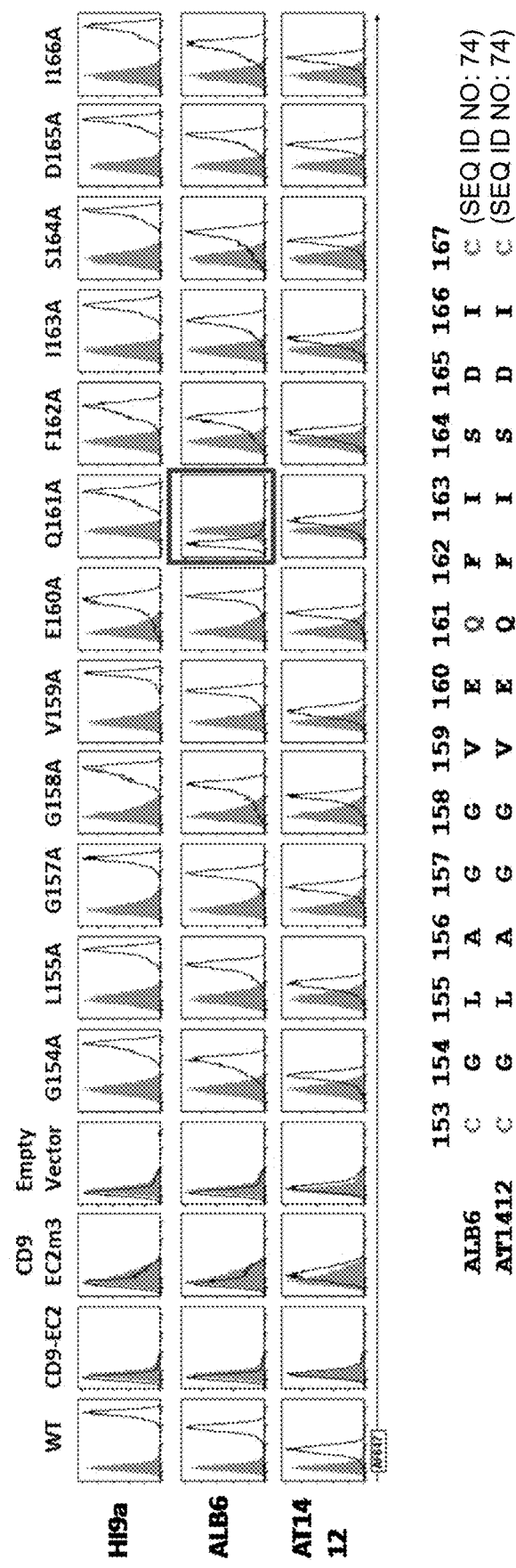

FIG. 15. Alanine scanning of region m3 expressed on HL60 cells did not show any loss of AT14-012 binding (n=2). Surprisingly, we determined that exchange of single amino acids in the m3 region did not disrupt AT14-012 binding. As a control, the CD9-WT, the CD9/CD81 EC2 hybrid mutant, the EC2 m3 CD9/CD81 hybrid mutant was included and the binding data shows overlap with previous reported data (FIG. 5).

FIG. 16. AT14-012 has lower affinity for CD9 as compared to commercial mouse anti-CD9 antibodies. A. CD9 binding of AT14-012 (+control AT10-002) and commercial abs HI9a and ALB6 (+controls anti-FLAG for detection of the presence of CD9 protein on the plate and OKT3) were compared. B. SPR curves showing binding of anti-CD9 antibodies AT14-012, ALB6 and HI9a for various injections of antibody for one single spotted CD9-3×FLAG-rabbitFc-Sortase-biotin protein. C. Affinity measurement of the different antibodies for human CD9 as determined by SPR. $k_a$ in $10^4$ $sec^{-1}$*$M^{-1}$, $k_d$ in $10^{-5}$ $sec^{-1}$, $K_D$ in pM. Shown are results on one CD9-spot coated with 7324 RU recombinant CD9-3×FLAG-rabbitFc-Sortase-biotin (0.5 µg/ml). To calculate binding kinetics, data from three duplicate injections were fitted to a 1:1 binding model. Shown are averages and standard deviations from measurements on three spots, coated with 0.5 or 1.0 µg/ml CD9-3×FLAG-rabbitFc-Sortase-biotin. *: When the apparent antibody dissociation rate ($k_d$) was too low for accurate fitting, a value of $0.1*10^{-5}$ is used. Shown are averages of two titrations on two spots, both coated with 0.5 µg/ml CD9-3×FLAG-rabbitFc-Sortase-biotin. To calculate the binding kinetics, data from three duplicate injections were used.

FIG. 17. K169, D171, V172, L173 and F176 are part of the AT14-012 epitope. A. ELISA data of AT14-012 (triangles, bottom line in all graphs), ALB6 (circles) and HI9a (squares) binding on recombinantly expressed m4 alanine mutants. B. AT14-012 epitope displayed onto a CD9 homology model (EC is extracellular and IC is intracellular orientation). Homology model was constructed using the I-Tasser server (Yang et al., 2015) using the CD81 homology model (2AVZ; Seigneuret et al., 2006). As of November 2016, a crystal structure was published (Zimmerman et al., 2016) and a newly constructed CD9 homology model based on this crystal structure did not show any chances with respect to the orientation of the residues related to the AT14-012 epitope. C. AT14-012 FACS binding data to cells from different species (see FIG. 11) and alignment of CD9 sequence (residues 23-228) from multiple species (here) strengthens the AT14-012 epitope. Sequences were retrieved from the ensembl.org website around June 2016. The first 22 residues were not well resolved for all found species and are therefore omitted here. AT14-012 is known to react with cynomolgus cells, whereas binding is lost when assayed for binding to rabbit or mouse cells. The alignment of region m4, flanked by C167 and C182 (green), is highlighted (light grey) and more specifically the 5 residues (dark grey) involved in AT14-012 binding. Apparently, the F176L mutation does not induce a loss of binding of AT14-012 (see AT14-012 binding to cynomolgus cells in FIG. 11C).

FIG. 18. Affinity improving AT14-012 using single cell sorted 2H15 B cells and SPR (IBIS). A. SPR curves of 8 sequential injections of recombinant AT14-012 at increasing concentrations (0-1.33-4.0-13.30-40.0-133.0- and 0 nM of protein). The green line is (no) binding reactivity towards CD81, orange binding to the anti-human IgG-Fc, grey the binding to anti-CH1 nanobody and blue binding to CD9. The ratio of the anti-IgG-Fc and aCH1 can be used to observe the concentration and integrity of the IgG in the B cell sup (see B). B. After screening of 800 clones in SPR as described in the materials and methods, we assayed newly grown B cell sups again for binding. Eight clones were increased (1D5, 1F5, 2D12, 4H10, 6E10, 9E5, 10B9 and 10D1) whereas 4 doubtful clones (1C9, 2H10, 9A9, 9D12) were eventually not. At the beginning and end there are injections of recombinant AT14-012 for reference. C. Sequence analysis of the found clones including affinities shows overlap in mutations related to their association/dissociation profiles. Group 1 shows faster association and slower dissociation, group2 faster association and dissociation and group3 no clear difference related to WT sequences (1G2, 1G3, 1G4, 1G5).

FIG. 19. Design, expression and analysis of AT14-012 higher affinity mutants binding on cells and SPR. A. As only the major mutations were located in the heavy chain, we only show the alignments of the heavy chain. Also, the combinations of group1 (red; H40Y and Y112F) and group2 (blue-cyan; D116H and T29N) and both groups together (H40Y, Y112F, D116H and T29N) were made. As a control, one mutation resulting in a lack of CD9 binding was added to verify the results (dark blue; G110D). The original AT14-012/2H15 hypermutations are highlighted in yellow. CDR numbering according to the IMGT numbering system (Lefranc 1997, Lefranc 1999 and Lefranc et al. 2003). B-C. MelWBO or short term cultured healthy melanocytes from two different donors' cells were incubated with CHO production supernatant of the different AT14-012 variants. Binding was detected by flow cytometry using a goat-anti-human IgG-PE secondary antibody. D-E. CHO production supernatant of the different AT14-012 variants was assayed on CD9 coated chip by SPR (shown in duplicates). #=CHO production supernatant. Affinities are in $k_a$ in $10^4$ sec$^{-1}$*M$^{-1}$, $k_d$ in $10^{-5}$ sec$^{-1}$, $K_D$ in pM. Shown are averages of two titrations on two spots, both coated with 0.5 μg/ml CD9-3× FLAG-rabbitFc-Sortase-biotin. Mutant samples were non-purified production sup, 1× diluted in PBST. -: no binding detected *: binding detected, but no good fit possible.

Figures 20, 21:
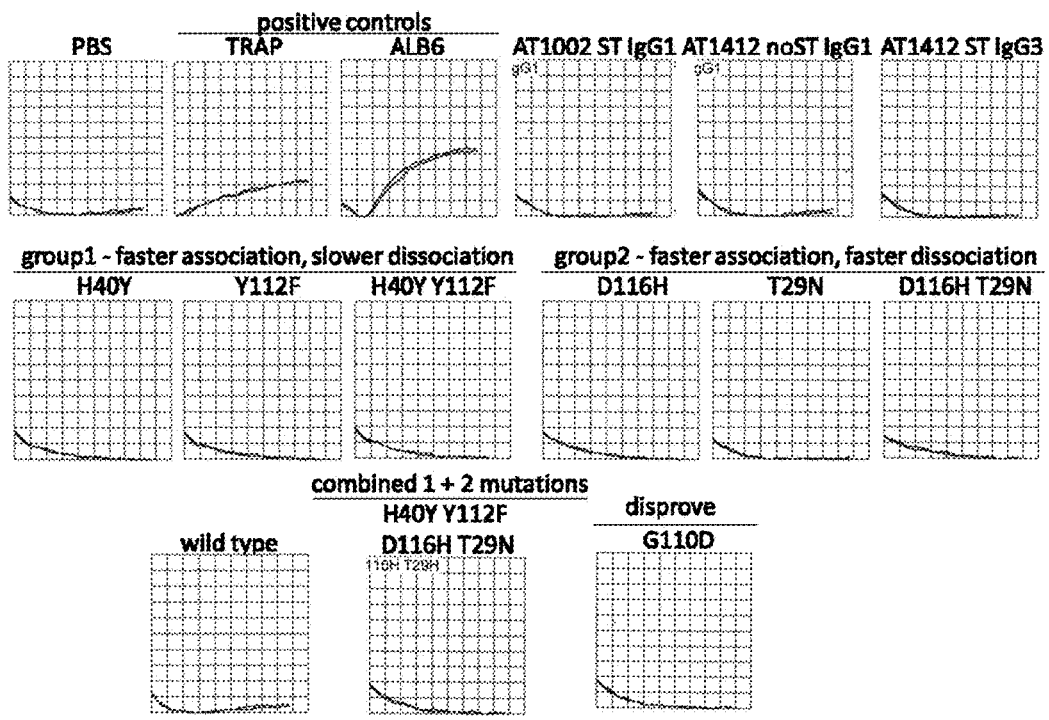

FIG. 20. Platelet aggregation assay using the AT14-012 high affinity mutants. As controls, TRAP, ALB6 and previously examined recombinant purified full length AT14-012 IgG1 and IgG3 including control AT10-002 IgG1 antibody were taken along.

FIG. 21. B cell produced AT14-012/2H15 antibody is of allotype IGHG3*16. mRNA was isolated from AT14-012/2H15 B cells. Figure is adapted from Vidarsson et al., 2014.

FIG. 22. AT14-012 combined with anti PD1 inhibits tumor growth in vivo. NSG mice carrying a human immune system are subcutaneous transplanted with SK-MEL-5 luciferase expressing melanoma tumor cells. Mice are treated twice per week with indicated antibodies. A. Tumor growth is determined by luciferase imaging. The grey area indicates the period of antibody treatment. B. The percentage tumor growth inhibition (TGI) is calculated based on the size of the tumors at the end of the experiment and the tumor size at the time of the first antibody injection.

EXAMPLES

Example 1—Isolation of AT14-012 B Cell Clone

MATERIALS & METHODS

Melanoma cell cultures. Melanoma cell lines MelBLM, Mel136.2 and MelWBO were obtained via Rosalie Luiten (Academic Medical Centre, Dept. of Dermatology) and maintained in IMDM (Life Technologies), 8% fetal calf serum using standard tissue culture techniques. For minimal disruption of cell surface proteins tumor cells were detached using Accutase (Life Technologies) or EDTA.

Melanoma donor PBMCs. Study protocols were approved by the Medical Ethical Committee of the Leiden University Medical Center. A stage IV melanoma patient was treated by adoptive transfer of autologous blood-derived tumor specific T cells in combination with IFNα (Verdegaal Cancer Immunol Immunother 2011). After treatment tumors regressed and the patient is the only long term survivor from its cohort. Blood was collected five years after treatment, PBMCs were isolated from a ficoll gradient and frozen to liquid nitrogen until B cell isolation.

B cell immortalization. Total IgG B cells were sorted from the thawed patient's PBMCs using a FACSAria (Becton Dickinson) and immortalized as described in Kwakkenbos Nat Med 2010. Briefly, total IgG B cells were cultured and activated during 36 hours on CD40L expressing L cells in the presence of recombinant mouse IL-21. By retroviral transduction our proprietary construct expressing Bcl6 and Bcl-xL and the marker gene GFP was introduced in the B cells rendering the B cell immortalized.

B cell culture. Immortalized B cells were maintained in IMDM (Gibco) supplemented with 8% FCS (HyClone), penicillin/streptomycin (Roche) and recombinant mouse IL-21 (50 ng/ml, in house produced). Gamma-irradiated (50Gy) CD40L expressing mouse fibroblasts were included as feeder cells. The cultures were routinely tested to be negative for the presence of *mycoplasma*.

Isolation of melanoma binding B cell clones. Immortalized IgG B cells were seeded at 25 cells per well of a 384 well plate and expanded using L-cells and mIL21. After approximately 2 weeks of culture antibody containing B cell supernatants were tested for binding to a mixture of melanoma cell lines. Positive binding was visualized by flow cytometry (FACS Canto and LSR Fortessa X20, Becton Dickinson) using an anti-human IgG-PE antibody (Southern Biotech). The positive minicultures were expanded and the procedure was repeated on single cell sorted B cells to retrieve the melanoma reactive B cell clone from the 25 cell miniculture. Panitumumab (anti EGFR1) was included as a positive control antibody.

Recombinant antibody production. To produce recombinant antibodies total RNA was isolated with the RNeasy® mini kit (Qiagen), generated cDNA, performed PCR and cloned the heavy and light chain variable regions into the pCR2.1 TA cloning vector (Invitrogen). To rule out reverse transcriptase or DNA polymerase induced mutation multiple clones were sequenced. The heavy and light variable regions of AT14-012 were cloned in frame with human IgG1 or IgG3 and Kappa constant regions into a pcDNA3.1 (Invitrogen) based vector. The resulting vector was transiently transfected 293T cells and recombinant antibody was purified from the culture supernatant using an AKTA purification system (General Electric Lifesciences). For control purposes an irrelevant control antibody (AT10-002) recognizing the HA antigen on influenza virus was included in the experiments.

Results

Identification and isolation of melanoma binding B cell clone. A patient with cutaneous melanoma and progressive metastatic disease stage IV was treated by adoptive transfer of autologous tumor-reactive T cells (Verdegaal Cancer Immunol Immunotherapy 2011). To this tumor tissue was obtained by surgery and used to establish an autologous melanoma cell line. Peripheral blood mononuclear cells were isolated from blood and put into co-culture with lethally irradiated autologous melanoma cells in T-cell medium. After 4 weeks of culture the tumor reactivity of the cultured T cells was confirmed in functional assays (Verdegaal Cancer Immunol. Immunotherapy 2011). The patient received two rounds of expanded autologous T cells and displayed a complete response and is still tumor free over 9 years after therapy.

From PBMCs isolated five years after the adoptive T cell therapy the total IgG B cell pool was retrovirally transduced with our proprietary Bcl6/Bcl-xL construct. Immortalized GFP positive cells were tested for the presence of melanoma binding antibodies by flow cytometry. An IgG3 B cell clone named AT14-012 displayed strong reactivity against both melanoma lines initially tested (MelBLM and MelWBO). Variable heavy and light chain sequences were determined (see FIG. 3) and DNA cloned in both an IgG1 and IgG3 backbone for recombinant antibody production in 293 or CHO cells.

Example 2—AT14-012 Target Antigen is CD9

MATERIALS & METHODS

AT14-012 Target Identification and Validation

Cells of the colon cancer cell line Caco2 (ATCC HTB-37), cells of the melanoma cell line MelBLM and cells of the human promyelocytic leukemia cell line HL-60 (negative control) were lysed (0.5% Triton X114 (Sigma), 150 mM NaCl, 10 mM Tris-HCL pH7.4, 1.5 mM MgCl2 supplemented with protease and phosphatase inhibitors (Roche)) and precleared with an irrelevant antibody (in-house generated RSV antibody D25), Protein-G and Streptavidin beads (Pierce) to remove non-specific binding proteins. For direct western blotting with AT14-012, we incubated purified recombinant AT14-012 for at least 1 hour at room temperature in TBS+5% BSA (Thermo Fisher) and 0.1% Tween20 (Sigma) on SDS-Page and blotted lysates. Blots were washed 3 times for 5 minutes in TBST and detected with a goat-anti-human-IgG (1:10.000 dilution HRP labeled; Jackson Laboratories) in TBST+5% BSA. Again, blots were washed 3 times for 5 minutes before development by chemiluminescence treatment. Precleared lysates were then incubated with bead-bound AT14-012 melanoma-specific antibody or with the influenza specific antibody AT10-002 as a negative control (3 hrs. at 4° C.). Antibody-incubated beads were washed three times in lysis buffer and bound proteins were eluted from the beads (0.1M Glycine pH10.5, 150 mM NaCl, 1% Triton X100, 1 mM EDTA) and neutralized with 1:10 volume of 2M Tris pH7.4. Again, samples were run on an SDS-PAGE gel. 85% of IP samples was run on SDS-PAGE and stained with Imperial protein stain (Pierce) to stain total proteins and excise specific bands for Mass Spectrometry. The rest of the immunoprecipitation (IP) samples were run on SDS-PAGE and transferred to PVDF membrane (Bio-Rad) for immunoblotting. The blot was incubated with AT14-012 or mouse-anti-CD9 (clone ALB6, Beckmann Coulter) for Western blot analysis to confirm the identity of CD9 (data not shown).

Epitope Mapping

Figure 1A:
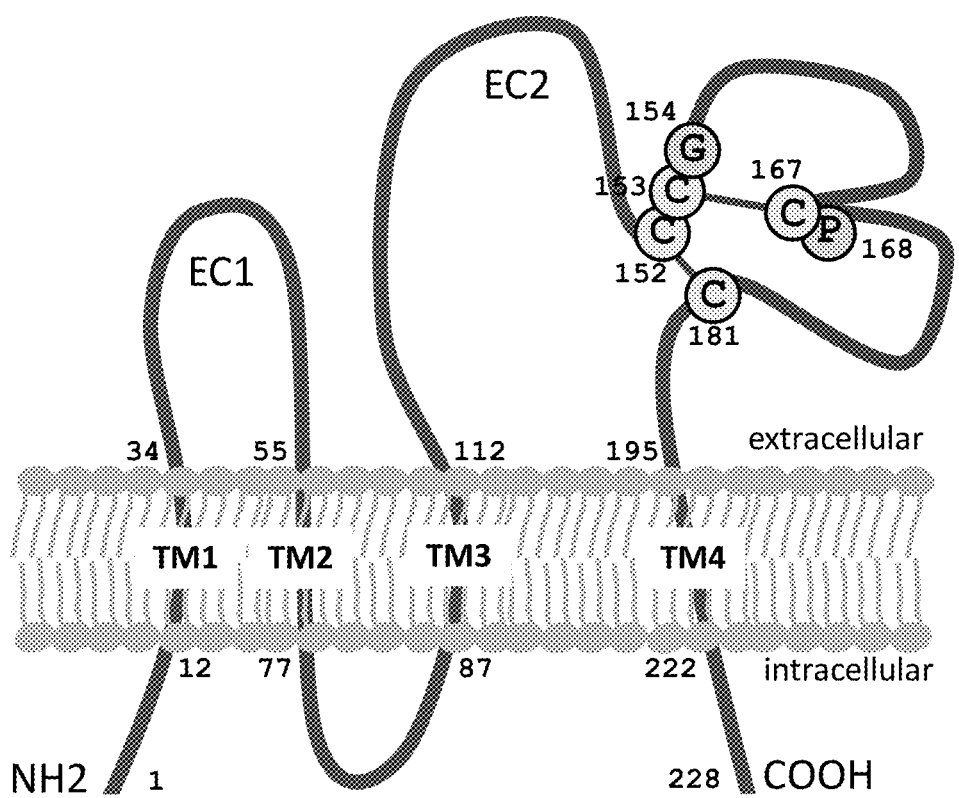
FIG. 1. Schematic structure of human CD9.

Epitope mapping was done initially by generating hybrid mutants of CD9 (vs CD81). There are two extracellular loops on CD9: the small EC1 (residues 34-58; or SEL) and large EC2 (residues 112-195; or LEL) which possibly serve as the binding partners for AT14-012 (FIG. 1a). In addition to the wildtype CD9 construct, we generated one swap mutant replacing the first smaller loop, and one swap mutant replacing the larger loop for the corresponding residues of CD81. To deconstruct the secondary loop even further, we proposed smaller swap mutants replacing predicted alpha helical stretches for the corresponding region of CD81 leading towards 5 swap mutants: m1 (residues 112-134 of CD9 replaced by the corresponding CD81 residues), m2 (residues 135-151 of CD9 replaced by the corresponding CD81 residues), m3 (residues 154-166 of CD9 replaced by the corresponding CD81 residues), m4 (residues 168-180 of CD9 replaced by the corresponding CD81 residues), and m5 (residues 182-195 of CD9 replaced by the corresponding CD81 residues), see FIG. 1b. The cysteines are conserved among tetraspanins (C152, C153, C167 and C181), and therefore the structural properties/fold will likely be intact after swapping the designated regions. Secondary structure predictions show that CD9 folds in a similar manner as other tetraspanins, indicating that this approach will work, as long as the cysteines are kept. All CD9 and swap variants were constructed by GeneArt (Thermo Fisher Scientific) of the CD9 gene and was C-terminal FLAG-tagged (3×FLAG: DYKDHDGDYKDHDIDYKDDDDK) (SEQ ID NO: 20) for possible detection on western blot. The CD9 cDNA was cloned into the pHEF-TIG third-generation lentiviral vector containing an IRES-GFP 3' of the CD9 cDNA; VSV-G lentiviral particles were produced in HEK293T cells. The multiple myeloma CD9 negative cell line HL-60 (ATCC; CCL-240) was transduced with these viruses in the presence of retronectin (Takara, Clontech, Japan) and sorted for GFP to obtain a pure population of CD9 overexpressing cells. Based on FACs binding results of 14-012 together with other commercial anti-CD9 antibodies (ALB6; Beckmann Coulter and HI9a; Biolegend), we generated alanine mutants of region m4 (residues K169A, K170A, D171A, V172A, L173A, E174A, T175A, F176A, T177A, V178A, K179A and S180A) to examine which specific amino acids in this m4 region were attributing to the epitope.

Epitope Mapping Using Alanine Scanning in the m3 Region of CD9

Figure 5B:
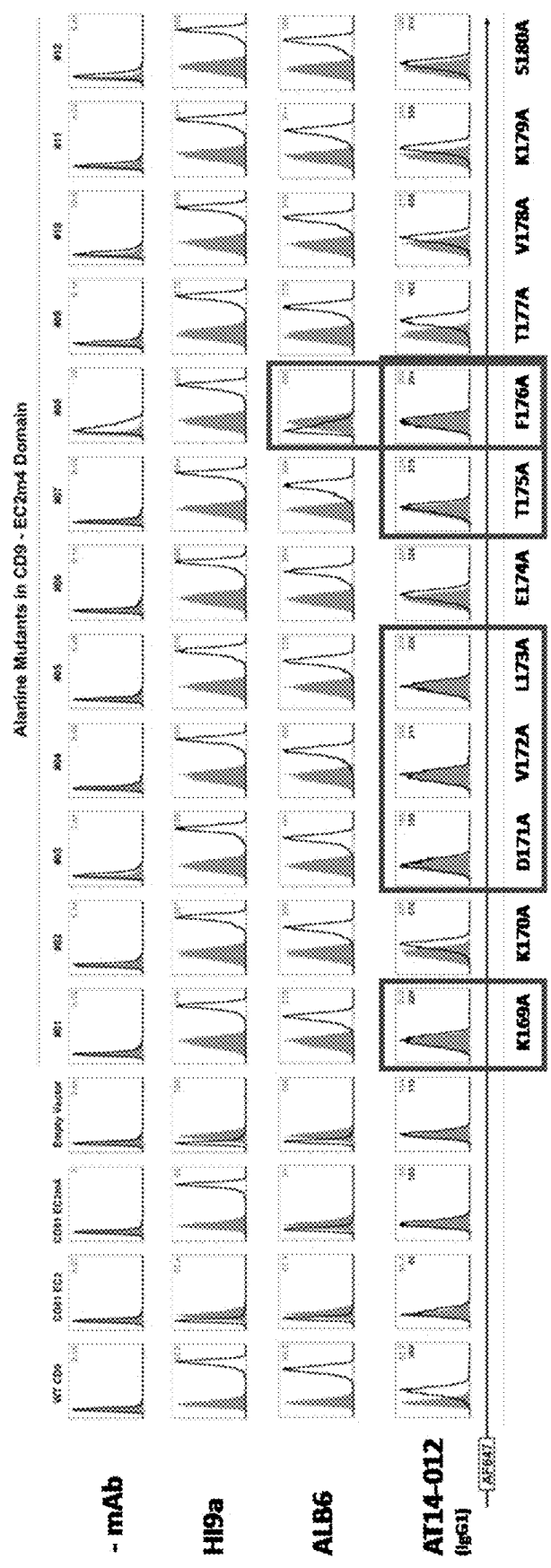

Alanine scanning was performed as described previously (see materials and methods belonging to FIG. 5B). The CD9 cDNA was cloned into the pHEF-TIG third generation lentiviral vector containing an IRES-GFP 3' of the CD9 cDNA; VSV-G lentiviral particles were produced in HEK293T cells. The multiple myeloma CD9 negative cell line HL-60 (ATCC; CCL-240) was transduced with these viruses in the presence of retronectin (Takara, Clontech, Japan) and sorted for GFP to obtain a pure population of CD9 overexpressing cells. Based on FACs binding results of AT14-012 together with other commercial anti-CD9 antibodies (ALB6 and HI9a), we generated alanine mutants of region m3 (residues G154A, L155A, G157A, G158A, V159A, E160A, Q161A, F162A, I163A, S164A, D165A, I166A) to examine which specific amino acids in this m3 region were attributing to the epitope.

Results

The Target of AT14-012 is CD9

Figure 4A:
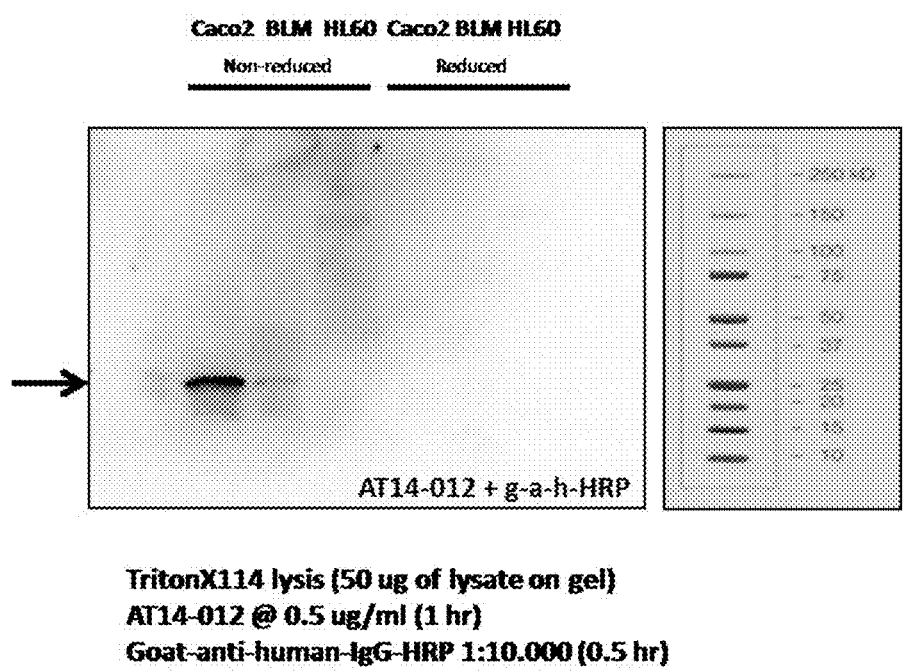
Figure 4B:
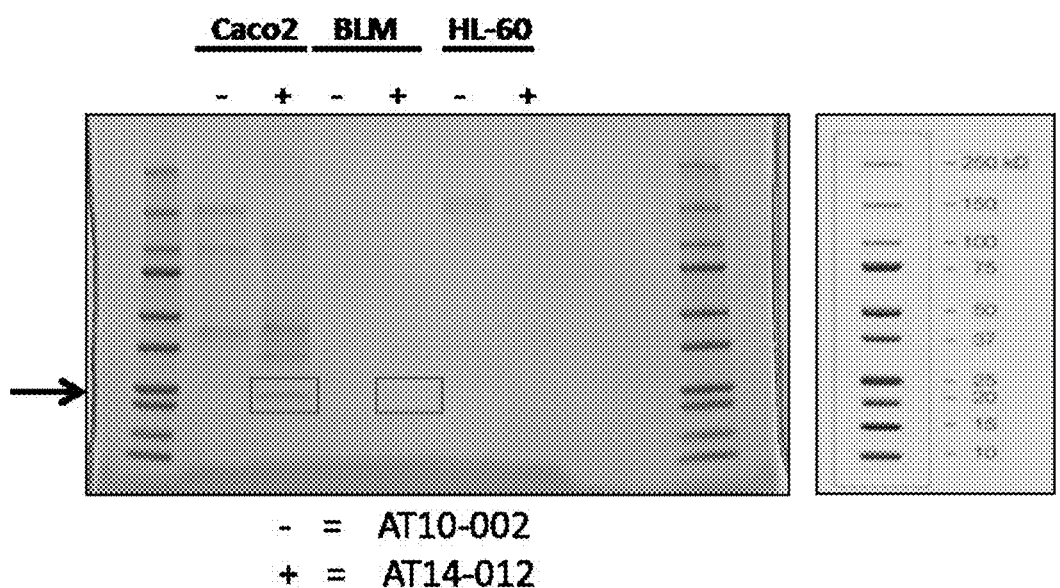
Figure 4C:
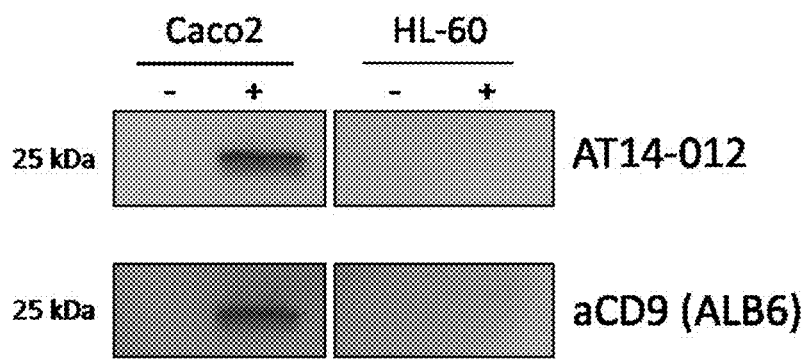

We identified the target of AT14-012 using colon cancer cells Caco2 (ATCC HTB-37) since the binding of AT14-012 was higher on FACs but confirmed in a similar manner on lysates of the melanoma cell line MelBLM. Western blots of SDS-Page run lysates of Caco2, MelBLM or HL-60 cells were probed for AT14-012 reactivity and detected with a polyclonal goat anti-human-IgG (HRP labeled; Jackson laboratories). The blot showed reactivity towards a ~25 kDa large protein (FIG. 4a). Reactivity or signal was lost when the lysates were run under reducing conditions, meaning that the antibody reacts with a conformational epitope constrained by cysteines. Immunoprecipitation (IP) of Caco2 or MelBLM lysates incubated with biotin-labeled sortase-tagged AT14-012 yielded also a ~25 kDa band (FIG. 4b). The band is specific as it was not seen in the AT10-002 IP of Caco2/MelBLM lysate nor in the HL-60 lysate IP. Mass-spectrometry (MS) analysis of the immunoprecipitation band revealed CD9 as the target protein. Although, no coommassie band was visible by eye for the IP on MelBLM cells, MS analysis showed to reveal the same precipitated CD9 antigen. Four extracellular peptides belonging to the extracellular loop 2 were identified, giving a 10% coverage of the protein. Transmembrane peptides were not identified since these are difficult to detect due to their hydrophobic nature. CD9 binding by AT14-012 was confirmed by western blot analysis (FIG. 4c). Briefly, Caco2 or HL-60 lysates were immunoprecipitated with AT14-012 or with the influenza-specific antibody AT10-002. Western blot analysis with again AT14-012 and the mouse-anti-CD9 (clone ALB6) confirmed CD9 as the binding target of AT14-012 (FIG. 4c).

CD9 is widely expressed on healthy and malignant cells. CD9-specific antibodies have been generated and are commercially available, such as ALB6 and HI9a. With these antibodies, we confirmed CD9 expression by Caco2 and BLM cells. Competition experiments with AT14-012 showed that all commercial antibodies were able to compete for binding of AT14-012 as well as AT14-012 itself (data not shown).

To more specifically identify the binding epitope of AT14-012, hybrid mutants were generated swapping protein regions of the CD9 homolog CD81 as described in the Materials & Methods section. Binding of antibodies AT14-

Figure 1B:
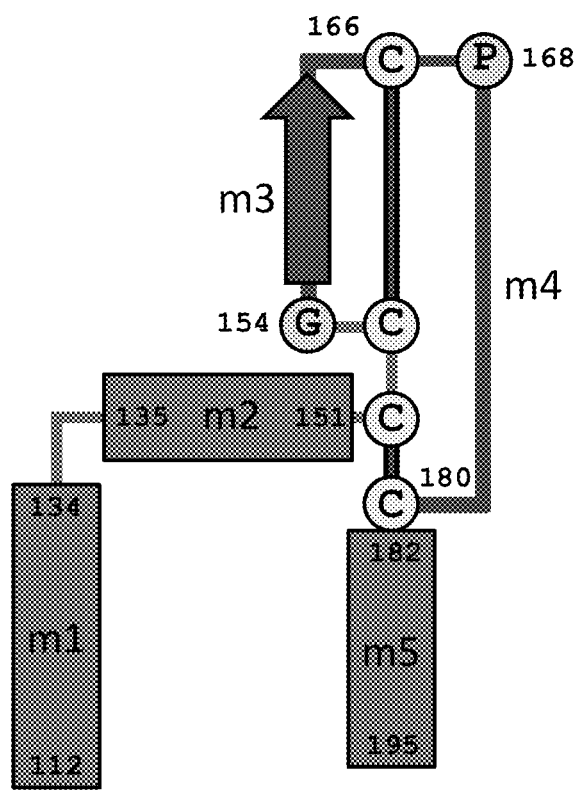

012, ALB6 and HI9a to these mutants was tested. We identified that all anti-CD9 antibodies bound to the extracellular loop 2 (EC2), showing loss of binding when the EC2 of CD81 was swapped, whereas binding was maintained when the first extracellular loop (EC1) was swapped. No binding was observed for all antibodies when HL60 cells were transduced with empty vector or non transduced cells. The epitope on the EC2 loop was further examined by hybrid mutants m1, m2, m3, m4 and m5, in which specific regions of CD9 were swapped for the corresponding regions of CD81 (FIG. 1b). Of note, the cysteines were left untouched in order to maintain the secondary structure. Swapping of the m2 and m5 region had no effect whatsoever on binding of any anti-CD9 antibody, showing that the epitope did not reside in these regions. We could show that binding of all antibodies was abrogated when region m3 was swapped, indicating that the epitope of all tested antibodies resides in this region. AT14-012 maintained binding to the m1 mutant whereas all commercial antibodies lost binding. ALB6 and AT14-012 showed loss of binding towards the m4 mutant whereas HI9a retained binding. These results indicate that the main epitope of AT14-012 resides in m3 and/or m4. This directed us to make alanine mutants in m4 at first (as described in the Materials & Methods section). Herein, HI9a was taken along as a positive control, controlling for expression of CD9 alanine mutants on the surface of transduced HL60 cells. ALB6 was taken along as a comparison, for examining whether this commercial widely used anti-CD9 antibody had a similar epitope. After FACs analysis, we showed that F176A was the only alanine mutant that showed loss of binding to ALB6. As for AT14-012, loss of binding was observed when residues K169, D171, V172, L173, T175 and F176 were substituted for an alanine. We thus showed that the epitope of AT14-012 overlaps with the epitope of ALB6 but differs in at least 5 additional amino acids.

AT14-012 epitope is linear and resides only in region m4. After the alanine scanning binding experiment of region m4, we pursued to examine the m3 region in more detail as binding was lost to the hybrid CD9/CD81 mutant (see FIG. 15). We constructed alanine mutants in region m3 spanning amino acids 154 to 166 with the exception of A156. We transduced the CD9 negative HL60 cell line and GFP bulk sorted the cells expressing CD9. AT14-012, ALB6 and HI9a binding to the cells was examined by FACS.

Surprisingly, no single alanine replacement in this region abolished binding of AT14-012 or HI9a. The EC2 and m3 CD9/CD81 hybrid mutant displayed a lack of binding for all antibodies and therefore, we have to postulate that this particular hybrid was probably wrongly folded. According to the crystal structure of CD81 and homology model of CD9 (see FIG. 15) the m3 region is "locked" in a position between m1, m2 and, m4. Therefore, it seems likely that the binding is lost for all anti-CD9 antibodies when any large exchange of amino acids is brought to this region. On a side note, ALB6 lost binding to the Q161A mutant and thereby, we solved the epitope for ALB6 as well (Q161 in m3 and F176 in m4). After analysis of the alanine scanning in region m3 and m4 we can hypothesize that AT14-012 targets a linear folded epitope which is conformationally held together or induced by other surrounding parts of CD9 (m2, m3 and m5 see homology model in FIG. 15).

AT14-012 favors binding to clustered CD9. The lab of Martin Hemler showed that the formation of CD9 homoclusters is favored by palmitoylation of CD9 and that levels of CD9 homoclusters are elevated on primary and in particular on metastatic tumor cells (Yang JBC 2006). To determine the dependence of AT14-012 on the palmitoylation status of CD9 tumor cells were cultured in presence of 2-bromo-palmitate (2-BP), a known inhibitor of palmitoylation. Melanoma BLM cells clearly show reduced binding of AT14-012 to 2-BP treated cells whereas binding of the commercially available CD9 HI9a antibody is not affected by depalmitoylation [FIG. 14A, B]. Of interest the observed effect was strongest on the highly aggressive MelBLM (Bartolome AJP 2009) and not seen on the non-metastatic colon carcinoma CaCo2 cells. This suggests that CD9 homoclusters are at higher levels in advanced disease, suggesting AT14-012 may be used to monitor tumor progression.

Example 3—Functional Characterization of AT14-012

Materials & Methods

Tumor cell lines. Melanoma (MelBLM, MelWBO, Mel136.2), Colon Carcinoma (CaCo2, Colo320, HT29, LSTR), Pancreas Carcinoma (PANC-1, CAPAN-2, MiaPACA, BxPC3), Esophagus Carcinoma (OE19, OE33) and, Acute Myeloid Leukemia (THP-1) cell lines were maintained under standard tissue culture conditions. For minimal disruption of cell surface proteins tumor cells were detached using Accutase (Life Technologies).

Flow cytometry and antibodies. Detached solid tumor cells and primary fibroblasts, non adherent tumor cells and other primary cells were prepared for flow cytometry analysis at 50,000 cells in a 96 well plate. Cells were incubated with commercial antibodies against CD4, CD8, CD9, CD19, CD41, CD62P, CD81 (Biolegend). In house generated AT10-002, anti CD30, or AT14-012 were either unlabeled, biotin or Alexa 647 labeled.

Unlabeled antibodies and biotin labelled antibodies were secondary stained with anti IgG-PE (Southern Biotech) or anti streptavidin PeCy7 (Becton Dickinson) respectively. Panitumumab (anti EGFR1) was included as a positive control antibody in some experiments. Samples were analyzed on a FACS Canto and LSR Fortessa X20 (Becton Dickinson).

Platelet activation. Blood collected from healthy volunteers in citrate containing blood collection tubes (Becton Dickinson) was spun for 10 minutes at 800 g. The top Platelet Rich Plasma fraction (PRP) was collected and used to test for platelet activation. Briefly 10 µl PRP was incubated for 20 min at room temperature with 10 µg/ml antibody, Fab2-fragments or the positive control Thrombin Receptor Activating Peptide (TRAMP). Samples were analysed by flow cytometry (LSR Fortessa X20, BD) for surface expression of CD41 and CD62P/P-selectin using direct conjugated antibodies (Biolegend). CD9 HI9a expression was determined on unstimulated platelets.

Platelet aggregation. Blood was collected from healthy volunteers in citrate containing blood collection tubes (Becton Dickinson). 300 µl whole blood mixed with 300 µl assay buffer was allowed to warm at 37° C. for 2 minutes. Positive control peptide or antibody (end concentration 10 µg/ml) was added and platelet aggregation was measured in time using a Multiplate analyser (Cobas/Roche).

Xenograft mice. Immunodeficient mice were transplanted subcutaneously with 200,000-500,000 luciferase/GFP expressing MelBLM cells in High Concentration Matrigel (Corning). AT14-012 or AT10-002 control antibody was given intravenously at 10 mg/kg mouse. Antibody treatment started at the day of tumor injection or tumors were allowed to grow for 3 weeks to determine growth of the primary subcutaneous tumor or outgrowth of metastasis respectively.

Subcutaneous tumor growth was determined both by caliper or luciferase imaging after luciferin (Promega) injection using a photon imager (Biospace lab). The presence of metastasis was visualized by eye and luciferase imaging at the end of the experiment.

Recently Established Tumor Cell Lines

Pieces of tumor tissue surgically removed from melanoma patient were digested and put into culture. Growing cells were maintained under standard tissue culture conditions. Tumor tissue obtained from pancreas carcinoma patients are too small to directly establish cell lines and are first grafted under the skin of NSG mice. Growing tumors are harvested, digested and maintained under standard tissue culture conditions. Human tumor cells and tumor infiltrating fibroblasts of mouse origin are separated by flowcytometry cell sorting based on EpCam expression.

Results

Figure 6A:
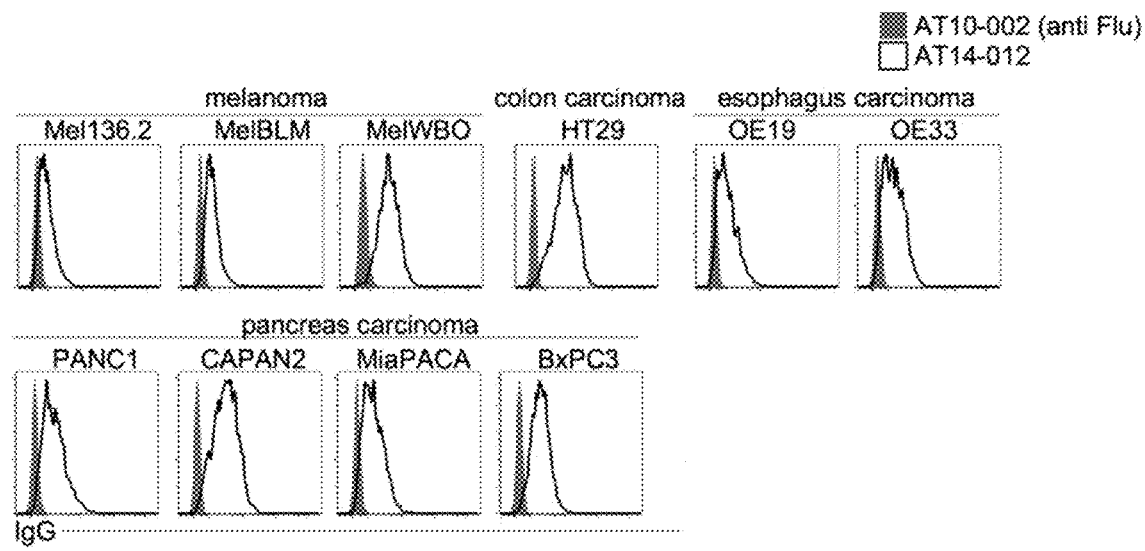
Figure 6B:
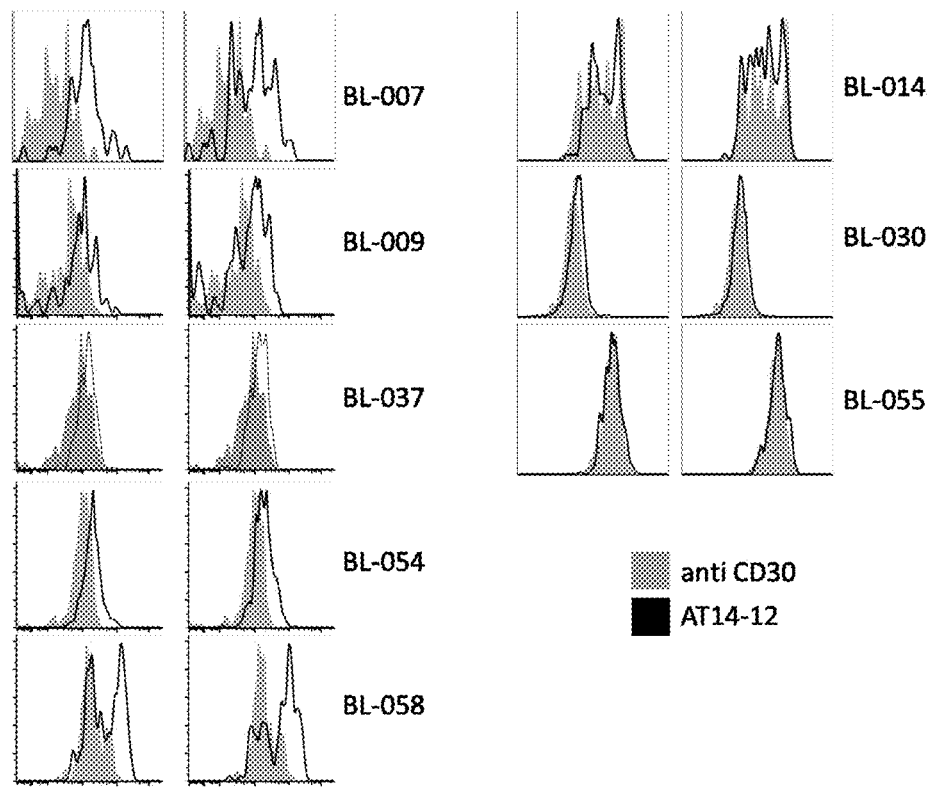
Figure 6C:
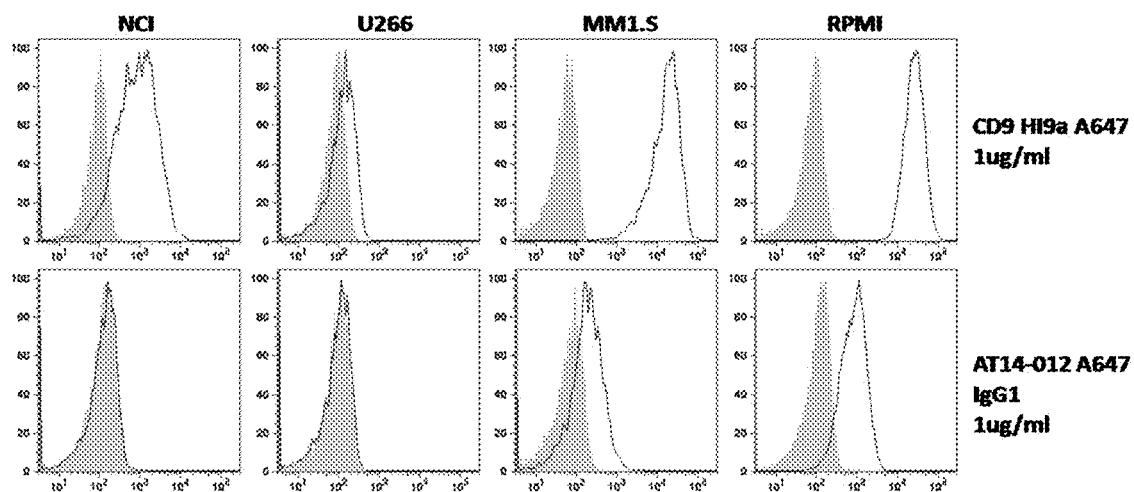

AT14-012 has broad tumor reactivity. AT14-012 was identified by binding to Melanoma cell lines MelBLM and MelWBO. Later it was found that AT14-012 displays binding reactivity to all melanoma cell lines tested (FIG. 6a and FIG. 7a). A relative large body of literature suggests that CD9 is broadly expressed and upregulated on a wide variety of solid tumor cells. In line with this we found that AT14-012 reacts with a panel of colon, esophagus and pancreas carcinoma cell lines (FIG. 6a and FIG. 7b). In our hands the only solid tumor cell line found thus far not to interact with AT14-012 is the CD9 negative Colo-320 colon carcinoma line (FIG. 7b). Although to a lesser extend CD9 has also been found expressed on hematopoietic cells. In FIG. 6b and FIG. 6c it is shown that AT14-012 is able to react to a selected number of Acute Myeloid Leukemia and Myeloid Leukemia cells (AT14-012 appears to bind BL-007, BL-009, BL-037, BL-054 and BL-058, whereas it does not bind BL-014, BL-030 and BL-055). Altogether this indicates that AT14-012 is useful for a much broader therapeutic application than melanoma only.

AT14-012 binds stronger to tumor than primary cells. None of the therapeutic antibodies for use of solid cancer treatment currently used in the clinic recognize antigens that are exclusively expressed on tumors. However, a therapeutic window for these antibodies presents itself when the antigen is higher expressed on tumor cells as compared to healthy cells. For example, Trastuzumab (Herceptin) is used to treat HER2 overexpressing breast cancer. Similar to this CD9 is known to be frequently upregulated on a wide variety of solid cancers. If AT14-012 reacts stronger to tumor cells as compared to healthy cells AT14-012 could be used in a therapeutic setting similar to Herceptin.

Indeed, we found that AT14-012 reacts stronger to melanoma cells than to primary melanocytes (FIG. 7a; all melanoma cell lines are bound by AT14-012, whereas primary fibroblasts are not bound. Primary melanocytes are bound by AT14-012, but to a lesser extent than most melanoma cell lines). Also, AT14-012 reacts stronger to colon carcinoma cells than to primary colon epithelial cells (FIG. 7b; AT14-012 binds CaCo2 (upper panel) stronger than primary colon epithelial cells (lower panel). Lastly, AT14-012 was found to bind stronger to the melanoma MelBLM cells than to primary tonsillar T and B lymphocytes (FIG. 7c; the lower images in the middle and right columns demonstrate stronger binding of AT14-012 to MelBLM as compared to the binding of AT14-012 to total CD4 T cells, total CD8 T cells and total CD19 B cells (upper images of the middle and right column)). These data indicate that AT14-012 is useful for a clinical setting currently used for antibody treatment of solid tumors.

AT14-012 binds and activates platelets but does not induce aggregation. It has been previously published that CD9 is highly expressed on platelets and that antibodies targeting CD9 can induce platelet activation and aggregation which potentially leads to thrombosis in patients treated with such anti CD9 antibody. Although the melanoma patient from which AT14-012 was isolated did not display any signs of thrombosis we needed to ensure that AT14-012 does not induce this serious side effect.

Firstly, the binding of AT14-012 to platelets was determined. Platelet rich plasma (PRP) from a healthy volunteer was incubated with a commercial antibody against CD9 or stained with AT14-012. Platelets were fixed to rule out any difference in cell surface expression of CD9 due to auto activation of the platelets. As expected from literature the commercial CD9 HI9a antibody strongly binds platelets (lower images of FIG. 8a). In line with this AT14-012 also showed strong interaction with the platelets (Upper images of FIG. 8a).

Next, we assessed whether the platelets would be activated upon interaction with AT14-012. Both Thrombin Receptor Activating Peptide (TRAP) and the commercial CD9 antibody ALB6 are known to stimulate the activation of platelets as visualized by cell surface upregulation of P-selectin/CD62P. PRP from a healthy volunteer incubated with TRAP or ALB6 indeed did show this surface induction of CD62P as compared to the unstimulated condition and the irrelevant ALB6 isotype matched FLAG antibody (FIG. 8b). Also, AT14-012 in both recombinant IgG1 and IgG3 formats as well as the antibody purified from the supernatant of the original B cell clone was able to activate the platelets (FIG. 8b).

Lastly it was determined whether AT14-012 induces the aggregation of platelets. For this whole blood was incubated with the same stimulants as before with the addition of Fab2 fragments of the AT10-002 and AT14-012 antibodies. As expected the TRAP peptide and ALB6 antibody induced strong aggregation of platelets (FIG. 8c). In contrast to the commercial CD9 ALB6 antibody, AT14-012 did not trigger the aggregation of platelets in any of the different formats (IgG1, IgG3, purified from B cell supernatant (2H15), or Fab2 fragment) (FIG. 8c). Altogether this shows that although AT14-012 binds and activates platelets, the interaction of AT14-012 with the platelets is not inducing platelet aggregation. These findings are in line with the observation that the AT14-012 donor did not display any signs of thrombosis. We therefore conclude that AT14-012 can be clinically used without involving thrombosis as a serious side effect.

AT14-012 impairs outgrowth of primary and secondary tumors. A tumor xenograft mouse model was set up to determine an anti tumor effect of AT14-012 in an in vivo setting. Immunodeficient mice are a suitable model for tumor engraftment. The mice received a subcutaneous transplant of 500,000 luciferase/GFP expressing MelBLM cells in Matrigel on both flanks. Tumors were allowed to grow for 3 weeks before the mice received intravenous injections of 10 mg/ml AT14-012 or our control anti influenza antibody (AT10-002) twice weekly for one or two weeks (depending on the size of the subcutaneous tumor). At 4 or 5 weeks after tumor cell graft, mice were sacrificed and internal organs exposed. In 3 out of 4 mice in the AT10-002 treated group, large luciferase positive lymph nodes were found suggesting that the MelBLM tumor cells are able to metastasize and develop secondary tumors in lymph nodes. In sharp contrast, none of the five mice that received the AT14-012 antibody showed any signs of lymph node metastasis (FIG. 9a). This demonstrates that AT14-012 is able to inhibit tumor metastasis.

In a follow up experiment mice received 200.000 MelBLM GFP/luciferase tumor cells on both flanks. This time antibody injection (twice weekly for 2 weeks 10 mg antibody per kg mouse) was initiated at the same time as tumor grafting. The size of the subcutaneous tumors was determined two times per week by caliper. As shown in FIG. 9b growth of tumors was reduced in the AT14-012- as compared to the control-treated mice. This shows that AT14-012 has a negative effect on tumor growth.

MelBLM subcutaneous tumors harvested from AT14-012 or AT10-002 control antibody treated mice were tested for presence of bound AT14-012 antibody by immunohistochemistry. Tumor tissue was imbedded in paraffin after which sections were incubated with HRP labelled anti-lambda or anti-kappa recognizing the light chain of the AT10-002 or AT14-012 antibodies respectively. As expected the AT10-002 anti-Influenza control antibody does not bind tumor tissue whereas AT14-012 clearly binds the outer layers of the tumor tissue and shows penetration to deeper layers (FIG. 9C). Single cell digests of MelBLM subcutaneous tumor cells harvested from AT14-012 or AT10-002 control antibody treated mice are tested for binding of CD9 antibodies AT14-012 and HI9a. Tumor cells harvested from AT14-012 treated mice show reduced binding of both AT14-012 and CD9 HI9a as compared to tumor cells from AT10-002 treated mice (FIG. 9D). The observed effect is not due to pre-occupation of the AT14-012 epitope by injected AT14-012 antibody as tumor cells from both treatment groups stain negative with an anti IgG antibody (FIG. 9D).

Of interest, in a repeat experiment with AT14-012 is also able to impair tumor growth of subcutaneously growing SK-MEL-5 melanoma tumors (FIG. 9E). The effect on tumor growth inhibition is more apparent when the weight of the tumor is determined. AT14-012 treated tumors clearly have a lower weight as their counterparts from AT10-002 treated mice (FIG. 9F). Of note, the reduction of CD9 levels on the tumors cells as observed on AT14-012 treated MelBLM tumors is confirmed when CD9 expression levels are determined in ex vivo isolated and digested SK-MEL-5 tumors (FIG. 9G).

Figure 10B:
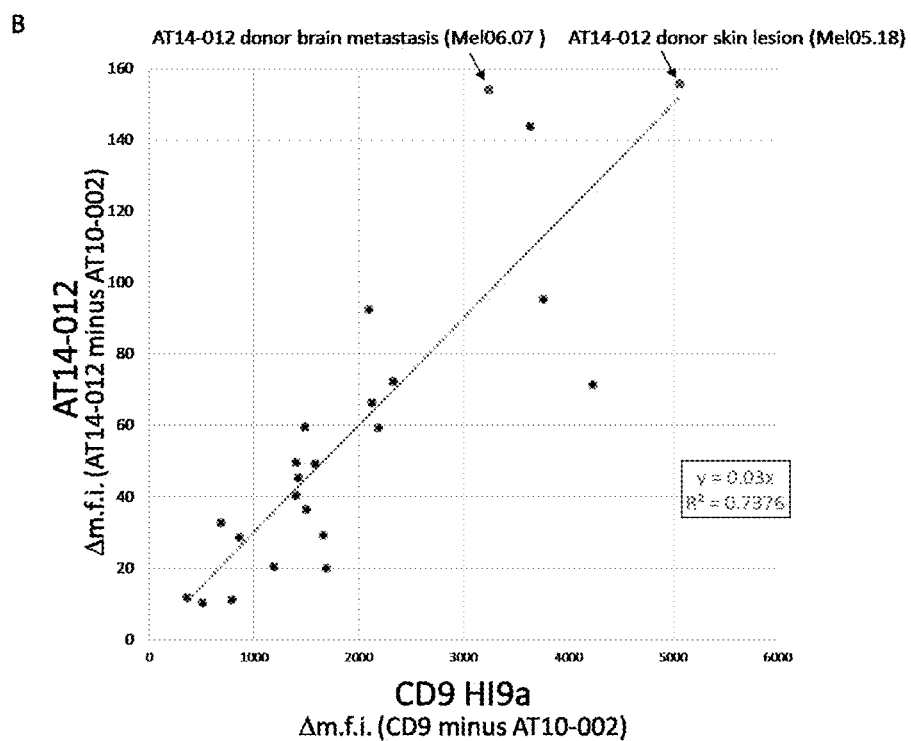
Figure 10C:
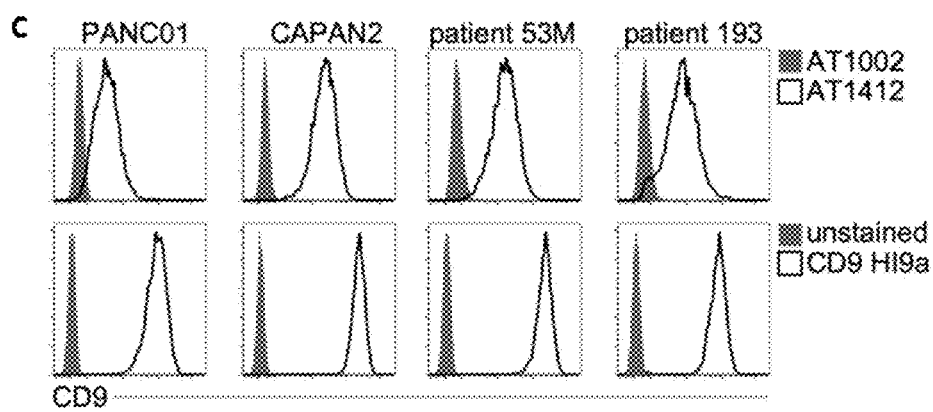

AT14-012 binds recent patient derived melanoma and pancreas tumor cells. AT14-012 is able to recognize a broad range of established solid tumor cell lines (FIG. 6A). Next is was tested if the AT14-012 binding reactivity also applies to tumor samples that were recently isolated from cancer patients. Short term cultured patient derived melanoma cells were tested for the binding of AT14-012. A positive signal with AT14-012 was observed on all primary melanoma samples tested (FIG. 10A-B). A strong correlation of AT14-012 binding and CD9 expression was observed (FIG. 10B). Of note, tumor cells derived from the melanoma patient from which AT14-012 was derived are the highest AT14-012 binders in the panel. Likewise, patient derived pancreas carcinoma tumor cells were subjected to binding of CD9 antibodies. In line with the efficient binding of AT14-012 to established pancreas carcinoma cell lines (FIG. 6A) AT14-012 display strong reactivity towards both patient derived pancreas carcinoma lines tested (FIG. 10C).

AT14-012 reactivity is restricted to primates. Tetraspanins in general and CD9 in particular are broadly expressed in a vast number of cells and tissues and have been suggested to be evolutionary conserved through distantly related species (Garcia-Espana, Genomics, 2008). Platelets of mice, rabbit, cynomolgus monkeys and a human are tested for binding of AT14-012. As expected CD9 is expressed on the platelets of all species tested. However, AT14-012 only reacts with platelets of the Cynomolgus monkeys and humans, binding to mice and rabbit was not observed (FIG. 11 A-C). Together this suggests that AT14-012 reactivity is restricted to primates.

Example 4—Complement and Antibody Depended Cytotoxicity

Materials & Methods
Complement Depended Cytotoxicity (CDC) Assay
Suspension or adhered melanoma cells were labelled for half an hour at room temperature with antibody. Subsequently cells were incubated with rabbit complement (S7764, Sigma) for 45 minutes at 37° C. Percentage cell death is determined by DAPI and flow cytometry (Fortessa X20, Becton Dickinson) or ToPRO3 and microscopy (Operetta, Perkin Elmer) for suspension and adhered cells respectively.

Antibody Dependent Cellular Cytoxicity (ADCC) Assay
Chromium-51 labelled target cells are incubated with 10 E g antibody for 30 min at 37° C. CD3 depleted PBMCs are added in a serial dilution followed by an additional 4 hours of incubation. The presence of Chromium-51 release in the supernatant is detected in LumaPlates (Perkin Elmer) using a Wallac-counter. Plotted values for antibody induced cell lysis are corrected for the spontaneous release of Chromium-51.

Figure 12A:
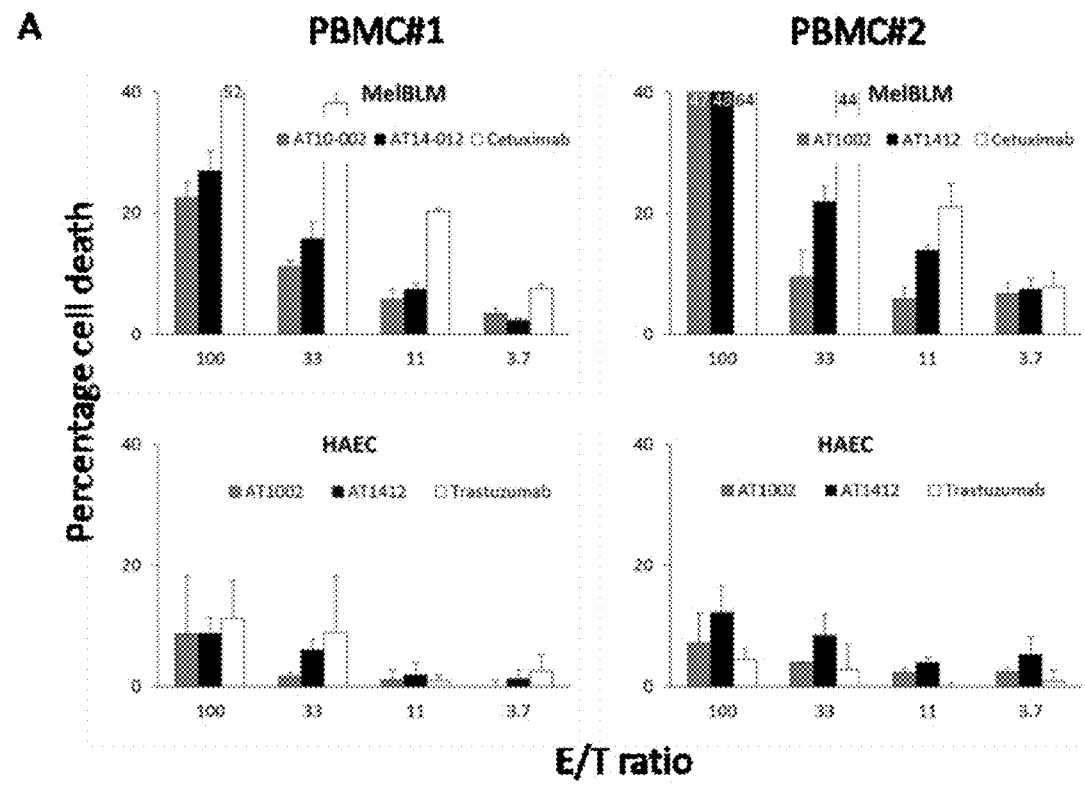
Figure 12B:
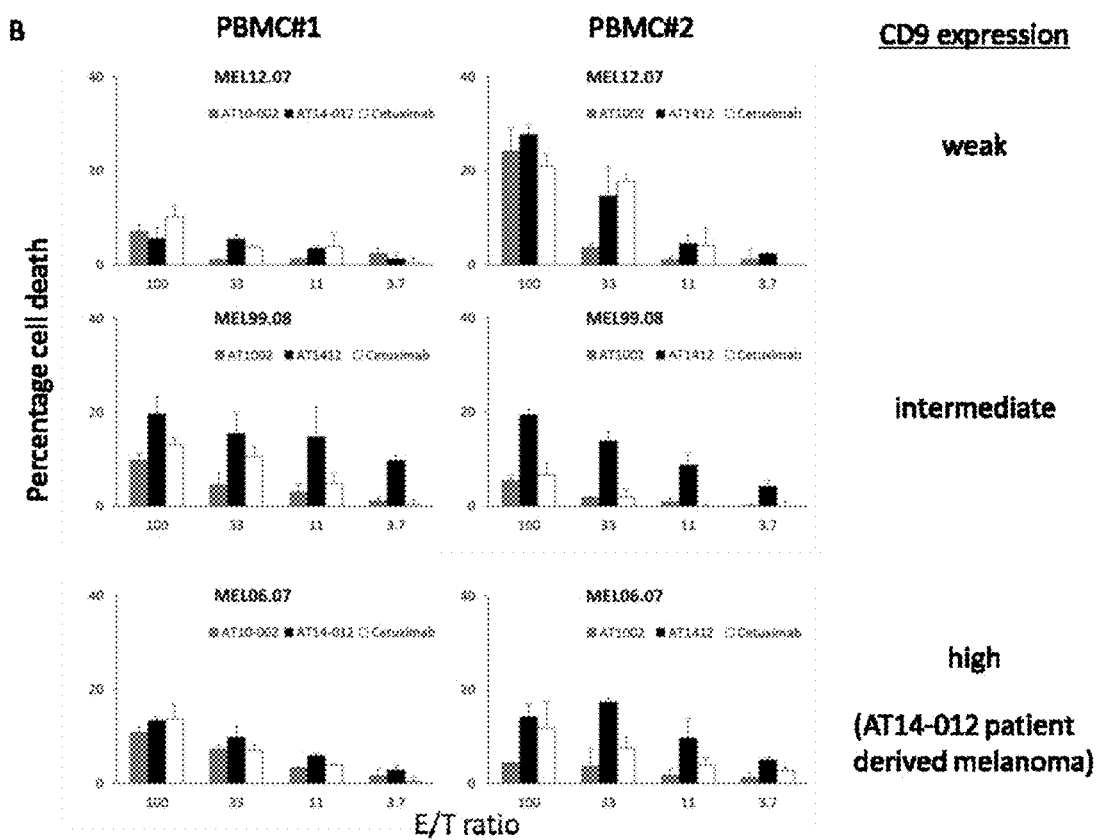

Results
AT14-012 triggers antibody dependent cytotoxicity (ADCC). To determine whether AT14-012 possess the ability to kill tumor cells via antibody dependent cytotoxicity (ADCC) tumor cells were labelled with radioactive Chromium and subsequently incubated with AT14-012, negative control AT10-002 (anti Influenza) or positive control (Cetuximab, anti EGFR1) antibodies. PBMC effector/melanoma target cell ratios were varied. The percentage cell death was determined by the release of Chromium from the dead cells in the medium. Less efficient than Cetuximab AT14-012 was able to kill MelBLM via ADCC while minimal cell death was observed when primary Human Artery Endothelial Cells (HAECs) were used as target cells (FIG. 12A). In parallel primary short termed cultured patient derived melanoma cells were tested for cell kill via ADCC by AT14-012. Although some variation between the different melanoma cells was observed AT14-012 was able to show ADCC activity over the AT10-002 control antibody (FIG. 12B). Altogether this suggests that the anti-tumor reactivity of AT14-012 is at least in part mediated via ADCC.

AT14-012 triggers complement dependent cytotoxicity (CDC). Several variants of the AT14-012 antibody were tested for their ability to trigger complement mediated cytotoxicity (CDC). 2H15 is the antibody derived from the original AT14-012 immortalized IgG3 B cell clone. The AT14-012 recombinant antibody based on 2H15 is produced in both an IgG1 or IgG3 backbone. In addition, we constructed a variant of the AT14-012 IgG1 antibody containing an E345R mutation in the Fc tail. This mutation has been shown to force hexamerization of a particular antibody on its target thereby efficiently triggering complement mediated cytotoxicity (CDC) (de Jong, PLOS Biology, 2016).

Figure 13C:
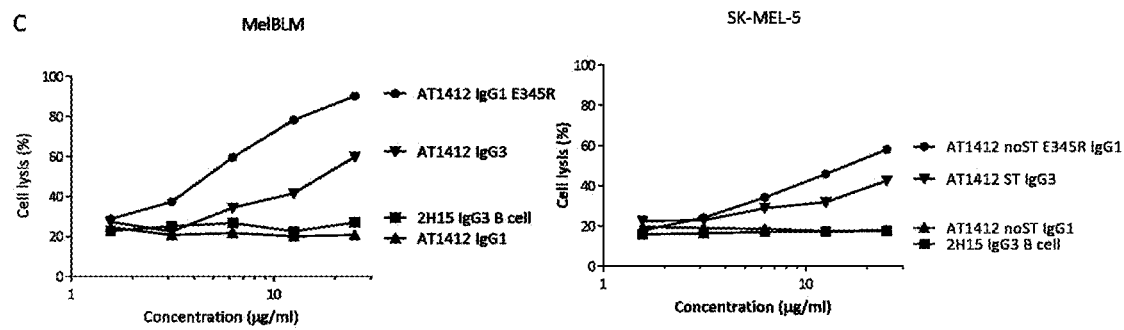
Figure 13D:
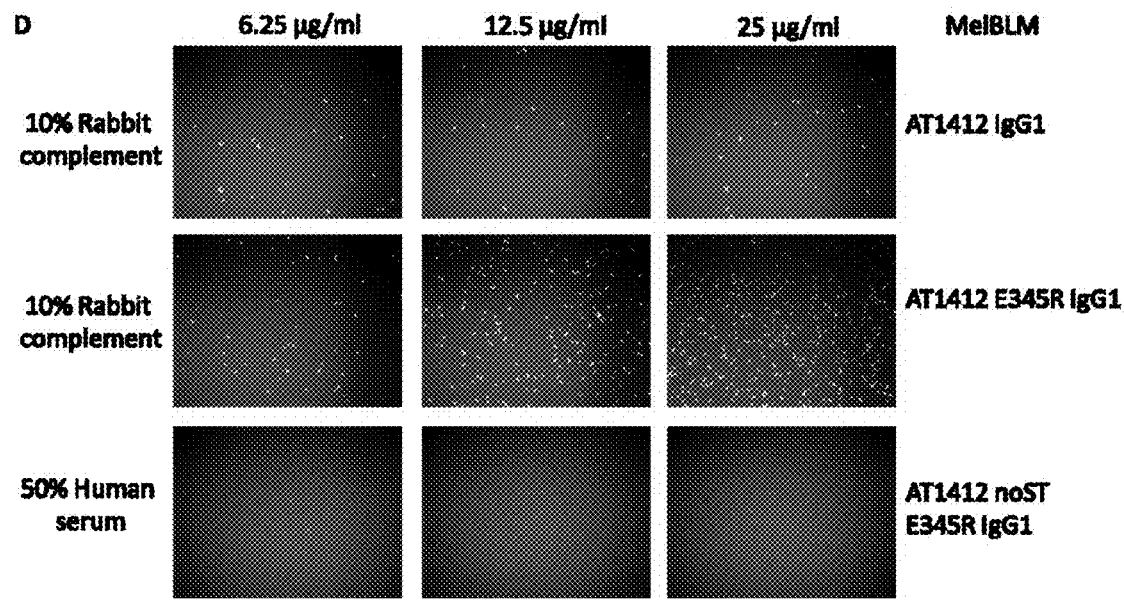
Figure 13E:
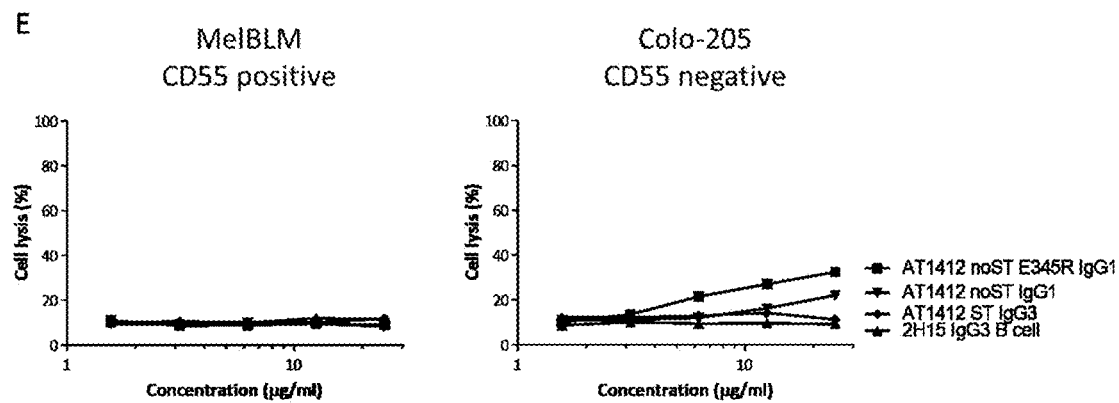

Melanoma lines in suspension were incubated with different AT14-012 variants in the presence of human serum and subsequently tested for the presence of C1q on the cell surface. As expected C1q deposition was observed with the AT14-012 hexamerization variant. In addition, C1q deposition was found with the 2H15 antibody purified from the original B cell clone and the recombinant produced AT14-012 IgG3. Of note AT14-012 engineered as an IgG1 did not attract C1q to the cells [FIG. 13A, B]. Suspension MelBLM or SK-MEL5 were incubated with the AT10-002 control anti Influenza antibody or any of the AT14-012 variants in the presence of rabbit complement. The AT14-012 IgG1 antibody does not induce any cytotoxicity similar to the anti Influenza negative control antibody [FIG. 13C]. In sharp contrast and in line with published observations [de Jong, PLOS Biology, 2016] introduction of the E345R mutation the antibody induces concentration dependent cell death via CDC [FIG. 13C]. These observations are comparable for suspension and adhered melanoma cells [FIG. 13 C, D]. Of interest AT14-012 recombinant produced as an IgG3 (thus without E345R mutation) is also able to trigger CDC [FIG. 13D]. Surprisingly, the original B cell produced 2H15 antibody does attract C1q, but does not induce complement mediated cell death [FIG. 13A, C]. AT14-012 E345R efficiently kills tumor cells by CDC in the presence of rabbit complement. While AT14-012 E345R is able to attract human C1q to the cell surface [FIG. 13A, B] the antibody is not able to trigger CDC mediated cell death in the presence of human complement factors [FIG. 13E]. We investigated whether the discrepancy of cell kill between rabbit and human complement is related to the expression of complement regulatory proteins (CRPs). Colo-205 which completely lack the expression of CD55, an inhibitor of C3 convertase formation, did allow antibody mediated CDC in the presence of human serum [FIG. 13E]. This suggests that AT14-012 may be able to induced complement dependent cell death of tumor cells when combined with a CD55 blocking antibody.

Example 5—Affinity Measurements

Materials & Methods
ELISA Binding AT14-012 Compared to Commercial Anti-CD9 Antibodies Binding of AT14-012 (IgG1) and control human AT10-002 antibody was assayed in an ELISA format to make a comparison to commercial antibodies ALB6, HI9a and mouse antibody controls anti-FLAG (for detection of CD9-3×FLAG-RabbitFc-Sort-biotin to the plate) and anti-CD3 OKT3 (muromonab). The ELISA setup is similar as described above to assay the amount of biotinylation of the CD9 molecules. The commercial abs were added in a serial dilution similar to that of AT14-012. The commercial abs were detected with a goat anti-mouse HRP labeled antibody (1:4000 from Jackson) whereas the human abs were detected with the goat anti-human HRP labeled antibody (1:4000 from Jackson). To compare the affinity differences in a better manner, we applied the antibodies in a surface plasmon resonance (SPR) assay on a CD9-3×FLAG-rabbitFc-Sortase-biotin coated SPR chip. EC50 values were calculated using GraphPad 7.0 software.

Affinity Measurement Using Surface Plasmon Resonance (SPR)

The chip for binding of the anti-CD9 antibodies was made in a similar manner as described for the AIMMprove detection (see below). Here, AT14-012 (+controls) affinity is measured in a 'classical' setup, regenerating the chip after each antibody injection. Binding was analyzed on the IBIS MX96 instrument by performing injections with dilution series of recombinant antibody diluted in binding buffer (PBS+0.05% Tween20+0.05% sodium azide+0.01% BSA) on the chip. In each injection, complexes were injected and incubated for 8 min, followed by 12 min thorough washing with system buffer (PBS+0.05% Tween20+0.05% sodium azide) to measure dissociation. Injections were repeated at least three times for every tested antibody and injections with blank binding buffer were used as reference. After each concatenated injection, the chip was regenerated with 10 mM glycine-HCl, pH 2.0+150 mM NaCl. Experimental data were processed with SPRintX software (IBIS Technologies) and kinetic constants were determined using Scrubber2 software (BioLogic).

Cloning, Expression, Purification and Sortase A Site Specific Biotinylation of CD9-EC2-3×FLAG-Rabbit-Fc-Sortase-HIS (+Control CD81-EC2-3×FLAG-Rabbit-Fc-SortaseHIS)

Freestyle cells (Thermo) were adapted and taken in culture for one week in serum free Freestyle medium (Gibco) in a 125 ml vent capped Corning flask on a shaker platform (140 rpm) at 37 degrees with 8% CO2. Transient transfection was performed using the pcDNA3.4 vector containing the CD9 sequence of the extracellular large loop 2 (amino acids 112-195; UniProt P21926) fused together with a 3×FLAG tag (-DYKDHDGDYKDHDIDYKDDDDK-) (SEQ ID NO: 20) and subsequently the Fc region (CH2-CH3) of a rabbit IgG1 protein (amino acids 108-322; UniProt P01870). The CD9 was spaced from the 3×FLAG tag by a -GGGT- linker, the 3×FLAG from the rabbit Fc by a -GSS- linker. The SortaseHIS tag (-LPETGGHHHHHH-stop) (SEQ ID NO: 34) was spaced from the Fc part by a -GGGS- linker. The insert was cloned into the pcDNA3.4 vector using the NcoI and PmeI restriction enzymes (NEB) and a large DNA preparation was isolated using a Qiagen plasmid maxi kit. DNA (3 ug of plasmid) and 6 μl of ExtremeGene9 (Sigma) solution in Optimem (Gibco) was incubated separately for 10 minutes in 100 μl Optimem. The 100 μl Optimem-ExtremeGene9 solution mix was added to the 100 μl Optimem-DNA mix and incubated for another 30 minutes before adding dropwise to a 3 ml culture having $0.5\times10^{\wedge}6$ cells/ml. Two days later, the medium was fed with another 2 ml of fresh Freestyle medium. The medium was harvested after 5-7 days of culture and put into a −80° C. freezer for further use. Culture conditions were scaled up if necessary for larger productions. Protein production was measured using a quantitative rabbit IgG ELISA (Jackson). Medium was defrosted and filtered before being applied to a 5 ml of protein G column (GE Healthcare) at a flow rate of 1 ml/min on an AKTA Explorer system (GE). The column was pre-equilibrated with PBS until a stable UV280/215 nm baseline was achieved. After application of the sample, the column was again washed with at least 5 column volumes PBS and until a stable UV280/215 nm baseline was kept. Bound protein was eluted with 0.2M Glycine+150 mM NaCl pH2.5. Top protein fractions were neutralized with 1:10 v/v 1M Tris pH9.0. The fractions were combined and applied onto a Superdex 200 16/60 column (GE) which was equilibrated with PBS. The monomeric peak was collected and quantified on a nanodrop 1000 system with the appropriate extinction/size settings for this protein. The protein was aliquoted for further use and stored at −20° C. for short term storage. The enzyme Sortase A (see Wagner et al., 2014 for preparation) was used in a 1:1 molar ratio together with a 10 times molar ratio of the GGG-biotin nucleophile to enzymatically attach a biotin moiety to the molecule in which the HIS tag was removed by the enzymatic Sortase A reaction. The reaction occurred in 25 mM Tris, 150 mM NaCl pH7.5 and 2 mM $CaCl_2$) for 4 hours at 37° C. with occasional gentle vortexing. The reaction was stopped by 1 mM EDTA. The biotinylated CD9 protein was separated from Sortase A and smaller components (free GGG-biotin nucleophile and free HIS tag) on a PBS equilibrated Superdex200 16/60 column. Top fractions were collected. The amount of biotinylation was checked via ELISA. In short, 5 ug/ml streptavidin was coated overnight in PBS onto a 96 well high binding ELISA plate (Costar). The biotinylated CD9 was applied to the wells in a serial two-step dilution with start concentration of 10 ug/ml in PBS+2.5% BSA for one hour. AT14-012 was added in a serial dilution as well to obtain a grid to examine the optimal signal for one hour in PBST+2.5% BSA. AT14-012 was detected by incubation of a goat-anti-human HRP labeled antibody (1:4000 dilution from Jackson) in PBST+2.5% BSA and developed using a TMB/$H_2O_2$ acidic solution. The reaction was stopped using 1M H2SO4 and measured using 450 nM on a Perkin Elmer Envision plate reader. The protein was sufficiently biotinylated and optimal concentrations were between 2.5 and 5 ug/ml. All the steps above were repeated for the control protein CD81-EC2-3×FLAG-rabbit-Fc-Sortase-HIS, as the coding region of CD9 was replaced for the EC2 coding region of CD81 (amino acids 113-201; UniProt P60033). The integrity and biotinylation of this protein was checked by ELISA using the anti-CD81 antibody clone JS81 (BD) and detected with a goat-anti-mouse HRP labeled antibody (Jackson).

Epitope Mapping of AT14-012 Using Soluble CD9-EC2-FLAG-Rabbit-Fc Protein in ELISA Alanine mutants of region m4 (amino acids 169-180) were cloned into the pcDNA3.4 vector mentioned above. The proteins were expressed in small scale (3 ml) and quantified using the rabbit IgG ELISA. To examine AT14-012, ALB6 and HI9a binding, we coated anti-FLAG antibody (Sigma) at 5 ug/ml overnight in PBS. Unpurified serum free supernatants were subjected to binding to the FLAG antibody at 1 ug/ml for 1 hour in PBST+2.5% BSA. After washing the random biotinylated HI9a, ALB6 and AT14-012 were subjected to binding to the captured CD9-FLAG-rabbit-Fc-SortaseHIS molecules. Bound antibody was detected with streptavidin-HRP (1:10.000 dilution from Thermo). ELISA was developed as described earlier. Random biotinylation of the antibodies was carried out using the EZ-Link NHS-Biotin kit (Thermo). Purified antibodies in PBS were subjected by an incubation of a 10-fold molar ratio of biotin label for 30 minutes at room temperature. The reaction was stopped by size exclusion. The biotinylated antibody was separated from the free label by applying the sample (1 ml at 1 mg/ml) on a PBS pre-equilibrated Superdex 200 16/60 column.

Construction of an m4 Circular Peptide.

The m4 region of CD9 (167-PKKDVLETFTVKS-180) was synthetically made by a peptide synthesis lab, analyzed by LCMS and purified by RP-HPLC using an Acetonitrile gradient. The peptide was lyophilized until completion. The peptide was flanked by two additional serines to mimic the space that the cysteine knot creates (see crystal structure of CD81) and followed by two cysteines that would make the peptide circular. For detection or capture purposes, a biotin moiety was placed at the N-terminus which was spaced by a single PEG2 group biotin-PEG(2)-CSPKKDVLETFTVKSSC (SEQ ID NO: 36) (cysteines are linked).

Results

AT14-012 is a medium affinity antibody. First, the amount of hypermutations brought to the heavy (4 amino acid replacements) and light chain (3 amino acid replacements) of AT14-012 might be an indication that the immune system was not adequately challenged in the patient to bring additional hypermutations to the variable domain sequences. Second, we could show that AT14-012 does not induce platelet aggregation whereas commercial antibodies developed by others did induce platelet aggregation. Also, the patient did not develop any thrombotic or thrombocytopenic symptoms (low platelets counts due to antibody mediated platelet destruction or aggregation) and was not treated with any agents that could have resolved this undiagnosed issue. The main question is whether the lower affinity of AT14-012 is beneficial to the properties of a "type" of anti-CD9 antibody that causes the optimal platelet phenotype or the usage of the unique epitope on CD9 (m4) targeted by AT14-012 results in an optimal non-aggregative platelet state. The binding of AT14-012 was tested in an ELISA setup using the recombinant expressed second extracellular loop of CD9 (EC2) to examine the differences in binding affinities with common used commercial murine anti-CD9 antibodies. We determined before (FIG. 5) that the epitope for all tested anti-CD9 antibodies resides in the EC2 loop. Although the two ELISA setups are different (detection with different secondary antibodies) between the human and mouse (commercial) antibodies, we could estimate that the EC50 of AT14-012 was significantly lower (EC50 ~250 ng/ml) compared to the commercial HI9a (EC50 ~20 ng/ml) and ALB6 (EC50 ~13 ng/ml). To make a better estimate in the affinity of AT14-012 compared to the commercial antibodies, we employed a label free detection setup using surface plasmon resonance (SPR). Three separate injections were employed over a CD9 layered SPR chip. The averaged affinity of AT14-012 in this setup was in the nM range (~44 nM) and the commercial antibodies were ~145 pM for ALB6 and HI9a ~2.33 pM (FIG. 16). The dissociation rate for AT14-012 measured is 700 times higher compared to HI9a which means that AT14-012 is able to detach from CD9 quite easily. HI9a is 19,000 higher affinity due to its low dissociation rate ($k_d$). We did not examine longer dissociation times for HI9a or ALB6 as the result for AT14-012 was obvious. ALB6 is still able to dissociate in a slow fashion after binding (~22 higher dissociation compared to HI9a) and contributes to the somewhat lower but still very high affinity when compared to HI9a.

Figure 17A:
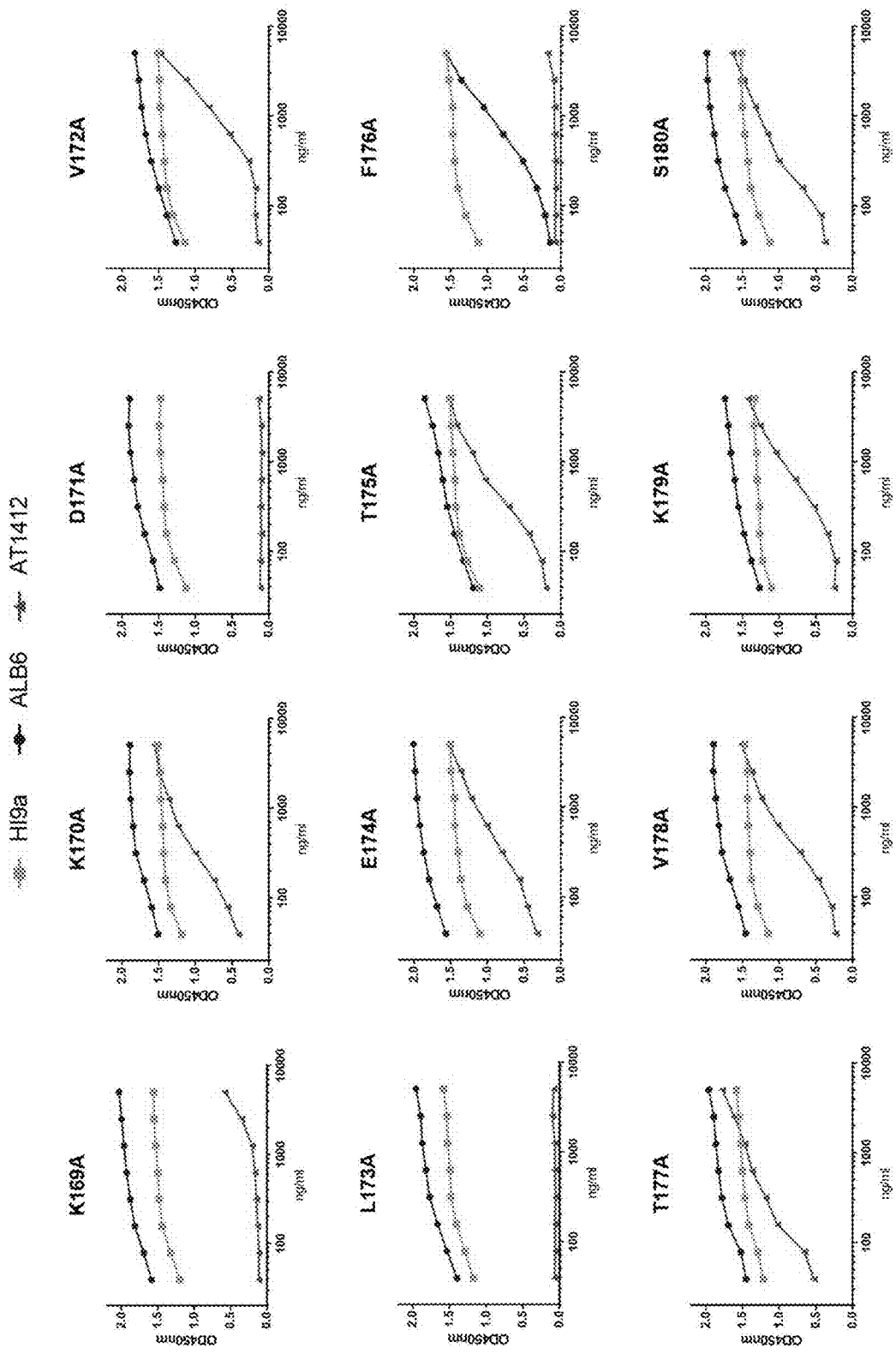

Epitope confirmation of AT14-012 using recombinantly expressed CD9-EC2 m4 alanine mutants. The epitope was investigated in further detail using an ELISA setup by incubation of random biotinylated anti-CD9 antibodies onto FLAG-tag captured CD9-EC2-3×FLAG-rabbitFc protein. The alanine mutants (amino acids K169A to S180A described in FIG. 5 were cloned and expressed as described in the materials and methods. Binding for AT14-012 is lost totally when alanine mutants are made at positions K169A, D171A, L173A, F176A and a significant decreased binding can be observed for V172A (FIG. 17A) which is line with previous FACS data (FIG. 5). ALB6 showed decreased binding to the F176A mutant as observed previously. HI9a does not lose any reactivity to any mutant and is an internal control for the presence of CD9 protein on the ELISA plate. Therefore, we can conclude that the epitope for HI9a does not reside in m3 or m4 or that a single alanine mutation brought to these regions does not abolish binding as the affinity of HI9a is of a significantly high value in this SPR setup. The epitope was mapped (highlighted by red) on the constructed homology of CD9 (FIG. 17B) and was located on the edge of the extracellular part of the protein. The alanine scan of m3 on FACs did not reveal any loss of binding to AT14-012 and we could not show any binding to a circular constructed m4 peptide in ELISA or SPR (data not shown). Therefore, we hypothesize that the correct folding of the m4 region is strongly influenced by other CD9 regions (m3 and m5) which leads to an AT14-012 conformational linear epitope. A co-crystal is required to confirm the epitope mapping data in further detail and to examine the contribution of every single amino acid on the CD9 epitope as well as the AT14-012 paratope. The epitope mapping data was further confirmed using the binding of AT14-012 to various species like cynomolgus, mouse and rabbit cells (FIG. 11). AT14-012 was able to react with cynomolgus cells, whereas binding was lost when assayed for binding to rabbit or mouse cells. The 5 residues contributing to the epitope of AT14-012 are aligned in FIG. 17C (highlighted in dark/red). Apparently, AT14-012 binding is lost when too many residues are varied as observed for the rabbit and mouse CD9 m4 sequences. Presumably, rabbit mutations (V172I, T175S, F176I and T177Q) and mouse mutations (D172Q, V172L, T175S and T177Q) in region m4 causes a major conformational change or shift of the AT14-012 epitope that might explain the lack of AT14-012 binding. On a side note, the F176L mutation alone does not induce a loss of binding of AT14-012 to cynomolgus cells (FIG. 17C).

Example 6—Affinity Improving AT14-012

Materials & Methods

Affinity Improving AT14-012 Using Single Cell Sorted 2H15 B Cells and SPR

The original identified B cell clone of AT14-012 (2H15; IgG3) was single cell sorted using a BD FACs ARIA III in ~20×384 well plates with appropriate culturing conditions. B cell outgrowth (~70%) was monitored via an Operetta confocal machine (Perking Elmer) observing Bcl6/Bcl-xL transduced GFP positive cells. Wells with positive signal were transferred to a fresh 96 well plate (8 plates in total) and cultured up to 1-2 weeks before the supernatant was harvested (100 ul) in a 96 well PCR plate and diluted 1:1 with PBS+0.05% Tween20+0.05% sodium azide and sealed frozen in a −80° C. freezer until further usage. Two wells were attributed to control supernatants of the original 2H15 clone and a control IgG3 B cell supernatant of an anti-HRV clone that does not bind to CD9 or CD81. SPR was performed on an IBIS Mx96 instrument (IBIS Technologies). Proteins are immobilized on an SPR chip pre-coated with streptavidin (G-STREP H825-065 (Sens Technologies) using a CFM microfluidics spotter device (Wasatch Microfluidics). Biotinylated anti-human CH1 nanobody (Thermo) and biotinylated full length anti-human Fc antibody (Jackson) were spotted at various concentrations for quantitation (examine the IgG concentration) as well as qualitative measures (IgG integrity). CD9- and CD81-3×FLAG-rabbitFc-Sortase-Biotin was also spotted at various concentrations to examine CD9 binding compared to a serial dilution of recombinant AT14-012 (IgG1) antibody. The binding was examined for all spots as such that similar amounts of spotted CD9 and CD81 could be compared. Binding of IgGs was monitored using the IBIS surface plasmon resonance imager described earlier and after each concatenated injection, the chip was regenerated with 10 mM glycine-HCl pH2.0+150 mM NaCl. The total amount of injections per plate in detail were as follows: (1) two injections with PBST to enforce a baseline, (2) one injection with anti-rabbit to check whether CD9 and CD81 were still on the chip and did not degrade over time/usage because of the extensive stripping, (3) one injection with PBST, (4) a serial dilution of recombinant AT14-012 IgG1 to measure the RU's for IgG concentration as well as CD9 binding (CD81 as control binding)-1.33-4.0-13.30-40.0-133.0 nM of protein, (5) two rows of B cell sups (A1 to A12 and B1 to B12), (6) one injection of recombinant AT14-012 IgG1, (7) two rows of B cell sups (C1 to C12 and D1 to D12), (8) one injection of recombinant AT14-012 IgG1 (9) one injection with PBST, (10) two rows of B cell sups (E1 to E12 and F1 to F12), (11) one injection of recombinant AT14-012 IgG1, (12) dependent on the plate a well was sacrificed to include a control B cell sup (IgG3 HRV clone plate 1=G1, plate 2=G2 etc.), (13) one row of B cell sups (G X? to G X? depends on the plate which numbers), (14) dependent on the plate a well was sacrificed to include a control B cell sup (2H15; IgG3 original clone, plate 1=G1, plate 2=G2 etc.), (15) one row of B cell sups (H X? to H X? depends on the plate which numbers), (16) one injection of recombinant AT14-012 IgG1, (17) a serial dilution of recombinant AT14-012 IgG1 to measure the RU's for IgG concentration as well as CD9 binding CD81 as control binding) -1.33-4.0-13.30-40.0-133.0 nM of protein to check for difference in RU's in the beginning of the run and after, (18) one injection with anti-rabbit to check whether CD9 and CD81 were still on the chip and did not degrade over time/usage because of stripping, (19) one final injection with PBST. In total, there were 117 injections and control checks (PBST and recombinant AT14-012 IgG1) with an association time of 8 minutes and dissociation time of 8 minutes which led to a total run time of ~50 hours per plate. Data is processed with SPRintX software (IBIS Technologies). B cell sub clone RNA isolation, cDNA amplification and sequencing were executed as described previously (Kwakkenbos et al., 2010).

Expression and analysis of the AT14-012 high affinity mutants CHO1-KSV cell line was taken up in culture for one week in CD CHO medium and refreshed every 2 to 3 days. Cells were transiently expressed (adapted from Rajendra et al., 2015) with the designated single mutants (H40Y, Y112F, D116H and T29N), combination double mutants (H40Y/Y112F and D116H/T29N) and combined quadruple mutant (H40Y/Y112F/D116H/T29N) including WT AT14-012 and control mutant (G110D), which does not show CD9 binding. In short, $4.0 \times 10^6$ cells/ml (10 ml) were taken up in CD CHO media supplemented with 0.25% DMA (Sigma). Cultures were added with 3.2 ug/ml DNA (pXC39 vector expressing both heavy and light chains) subsequently with PEImax (Sigma). After two days, a feed of 10 ml of fresh medium was added. Medium was harvested after 7 days and IgG expression was quantified using the IgG quantification ELISA (Jackson). Cell culture supernatants were tested for binding to MelWBO cultured cells (see elsewhere) in FACS and in a similar manner using the same SPR chip setup used for the AIMMprove method. Alignments were made using Seaview software (Gouy et al., 2010).

Results

Development of high affinity AT14-012 variants using SPR. As mentioned before, the main question for development of AT14-012 antibody would be whether a higher affinity variant (as comparable affinity to ALB6) would lead to platelet aggregation.

Figure 18A:
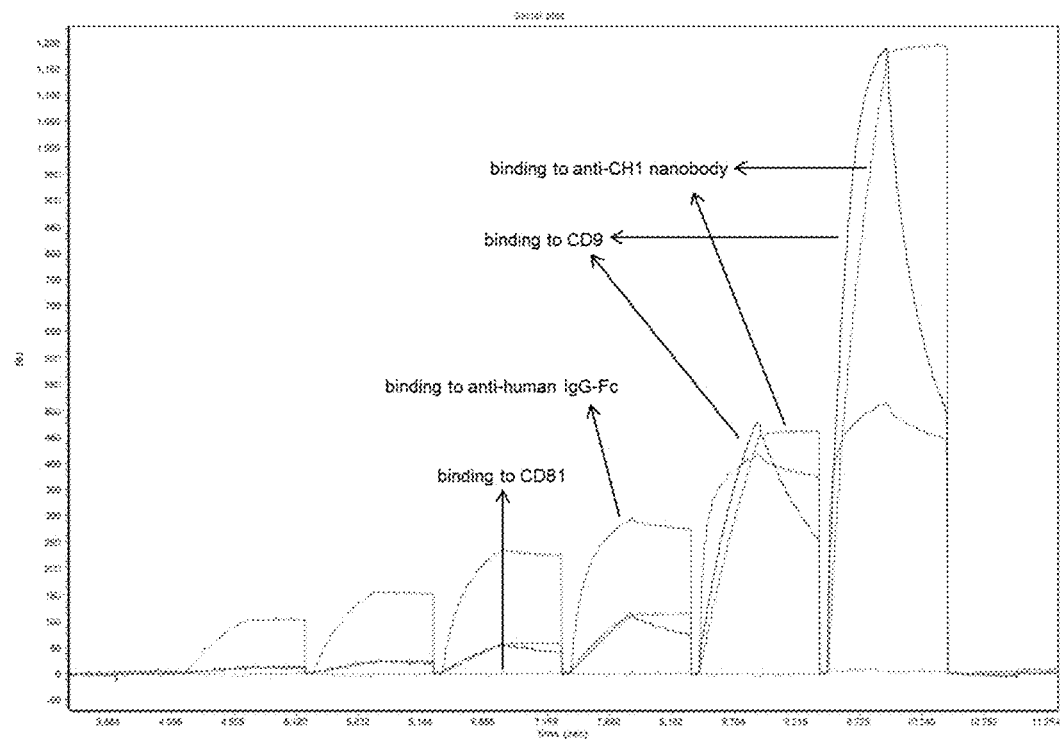
Figure 18B:
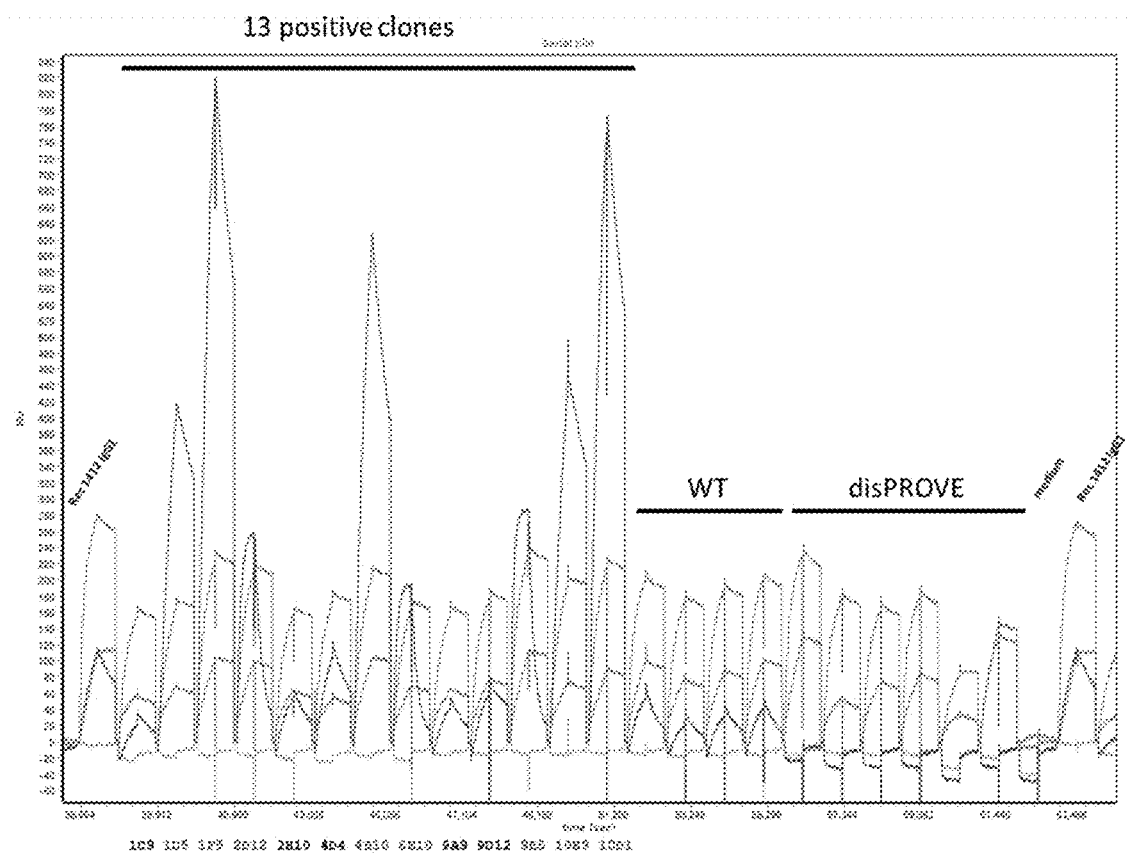

Alternatively, does AT14-012 target such a unique epitope in which the affinity would not make any difference? Activation-induced cytidine deaminase, also known as AID, is still expressed and active in the immortalized B cell repertoire. Expression of AID did not result in genetic instability leading to growth arrest and cell death, as 63% of wells that were seeded showed robust expansion (Kwakkenbos et al., 2010). Thus, AID is still able to induce mutations randomly or preferably at a mutational hotspot. One approach to identify mutations which lead to a higher affinity antibody/antigen binding, would be to sort single B cells that would bind fluorescently labeled soluble CD9 protein and compare it with the IgG expression. In short, we were not able to find any setup to have soluble CD9 either in a single, tetramer (using streptavidin-PE) or multimerized form (using PE labeled dextramers) to bind the 2H15 B cells (data not shown). This is probably due to the cis-type binding of the 2H15 B cell receptor to CD9 expressed on the surface of the B cell itself. Therefore, we used a similar setup to single cells sort the original 2H15 B cells but now test the binding of the produced IgG to a recombinant CD9-EC2 protein in SPR (similar CD9 protein as used for the AT14-012 affinity determination). The 2H15 single B cells are able to produce sufficient amounts of IgGs to be tested especially if a mutation induces increased binding. Initially, we examined optimal SPR settings using the bulk 2H15 cultured IgGs in supernatant and compared it to increasing concentrations of recombinant AT14-012 (FIG. 18A) as a control. After validation of a proper association and dissociation phase of the 2H15 IgGs, we employed a setup in which the observed concentration and integrity of the IgG in the B cell supernatant could be related to the binding of recombinant purified AT14-012 at properly determined IgG concentrations (see FIG. 18A). The ratio related to the binding to the anti-human Fc and the anti-CH1 showed a good correlation between concentration and stably produced antibody. The SPR curves of the anti-human Fc increase in a linear manner whereas the SPR curves for the anti-CH1 increase in an exponential manner. We were able to identify 13 clones with enhanced or altered binding pattern after examination of eight 96 well plates (~800 clones) and ~400 hours of SPR run time (raw data not shown). These clones were taken into culture and examined again on a newly generated SPR chip (FIG. 18B). Out of the initial 13 clones only 8 still showed significantly enhanced binding. There were 3 different groups designated in which group 1 showed faster association and slower dissociation (clones 1D5, 1F5, 4H10, 10B9 and 10D1). Group 2 clones showed a faster association but also a faster dissociation (clones 2D12, 4D4, 6E10 and 9E5) and group 3 did not show any difference (clones 1C9, 2H10, 9A9 and 9D12). Enhanced binding of the high affinity clones was also examined and detected on two different melanoma cell lines (data not shown). Again, group 1 clones showed the best cell population shift on FACs. One single mutation in the heavy chain of the clone attributes to the enhanced binding pattern in SPR and on cells (see FIG. 18C). Surprisingly, one clone 4D4 was the only clone to have light chain mutations and no heavy chain mutations. We also examined a few clones that did show IgG expression but no CD9 binding (referred to as "disPROVE", clones 1E3, 1E4, 1E5, 1F12, 2A3 and 5B1). And, we included a few clones (1G2, 1G3, 1G4 and 1G5) that showed a consensus binding pattern among all 800 analyzed clones. It was established that these clones were most germline (FIG. 18C). The most important mutations were the H40Y (4×) and Y112F (1×) (group 1) and the D116H (2×) and T29N (1×) (group 2). The L120V mutation (clone 4H10) as well as the S28N (clone 9E5), both located in the light chain, were omitted because of other clones having the same mutation in the heavy chain and also equal CD9 affinities.

Figures 19A, 19B:
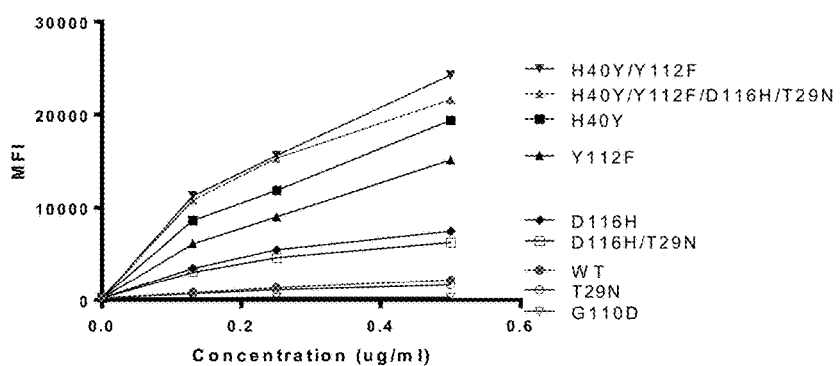
Figures 19D, 19E:
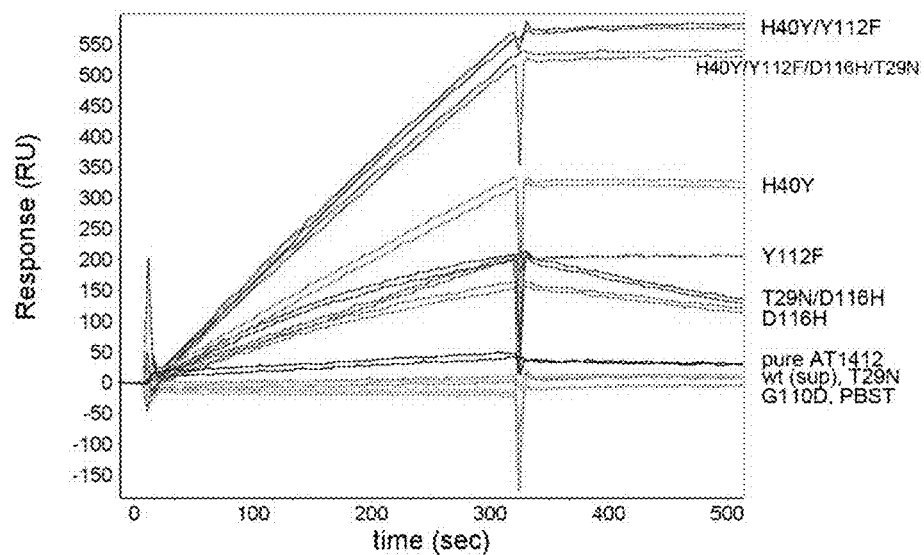

Examination of the high affinity mutants and combination thereof in recombinant AT14-012 background. The high affinity mutations were transiently expressed as single, double or quadruple variants in CHO cells (see FIG. 19A) for the positions and alignments). WT AT14-012 and the mutant G110D, which resulted in a lack of CD9 binding, were taken along as controls. The antibodies were assayed for integrity and break down products on SDS-page and western blot. No obvious abnormalities could be detected when the antibodies were detected with a rabbit anti-human IgG heavy/light chain antibody (data not shown). Production supernatant was used at a serial dilution on melanoma cells to examine CD9 cell surface binding (FIG. 19B). The G110D mutant, which resulted in a lack of CD9 binding, was genuinely interfering with the binding to CD9. The T29N did not have a major impact on improved binding as observed for the B cell supernatant screening. The D116H does show an expected improved binding. The combination of these two group 2 mutations did not attribute to an even higher signal compared to the single D116H binding. Again, this result explains the lack of impact the T29N mutation has in recombinant form. Fortunately, the binding of the group 1 mutations was increased significantly better with the H40Y to have the most impact of all single mutations. As for the double group 1 mutant (H40Y/Y112F) the effect became even more enhanced. The quadruple variant did not show any beneficial effect over the double group 1 mutant. In line with the binding pattern observed for WT AT14-012 (FIG. 7A) also the high affinity variants show enhanced binding to melanoma cells as compared to short term cultured healthy melanocytes (FIG. 19C). An exact binding profile was achieved using the CD9 SPR setup (FIG. 19D). The contribution to the higher binding was nicely explained by the overview of the association and dissociation constants (FIG. 19E). All single mutants, except for T29N, contributed to an enhanced binding affinity. The H40Y mutant showed a 100 times enhancement, as for Y112F 50 times and D116H 10 times. The combination group 1 mutant contributed to a 250 times higher affinity compared to WT AT14-012 (~220 pM). Surprisingly, the quadruple mutant twice less high (~455 pM) compared to the group 1 double mutant. This leads to an antibody with a comparable affinity range as ALB6. This mouse anti-CD9 antibody is known to induce platelet aggregation and is used as a positive control in the platelet aggregation assay. Now, we have comparable binding affinities to answer the question whether the platelet aggregation is affinity or epitope related.

Affinity improved AT14-012 mutants do not aggregate platelets. In line with literature we observed that the commercially available anti CD9 antibody ALB6 antibody induces the aggregation of platelets. In sharp contrast incubation of whole blood with the anti CD9 antibody AT14-012 does not cause platelets to aggregate. Importantly, when the high affinity mutants were tested in our platelet aggregation assay none of the AT14-012 affinity improved variants was able to induce the aggregation of platelets (FIG. 20). The ALB6 antibody was included in the assay as a positive control for aggregation of platelets. The affinity of the double group 1 mutant is approximately the same as the affinity of the ALB6 antibody (FIG. 16C). This indicates that the affinity of AT14-012 is not linked to the absence of platelet aggregation, but instead the crucial characteristic is the recognition of a unique epitope on CD9.

Example 7—IgG Iso- and Allotype

Materials & Methods

Sequencing of the CD9 Open Reading Frame from Patient Derived Tumour Material and Cancer Cell Lines In short, mRNA was isolated using Trizol reagent and cDNA amplification was performed using random primers. CD9 was amplified by PCR using CD9 specific primers described in Huang et al., 1998. CD9 sequences was analyzed from frozen cell pellets of two short term cultured primary tumor material sources (AT14-012 derived) designated Mel05.18 from a skin lesion and Mel06.07 from a brain lesion. Two other short term cultured primary tumor material, both AT14-012 binding positive from other melanoma patients were taken along as controls. Furthermore, melanoma cell lines MelBLM, MelWBO, A375 and Jurkat T cell line (negative for CD9 binding) as well as AML cell line HL-60 were used to examine the CD9 sequence. The B cell clone 2H15 and IgG3 anti-HRV B cell clone were also analyzed. Sequencing was carried out on the PCR products itself (CD9-fw 5'-TGCATCTGTATCCAGCGCCA-3' (SEQ ID NO: 37) and CD9-rev 5'-CTCAGG-GATGTAAGCTGACT-3') (SEQ ID NO: 38).

Sequencing of the IgG3 2H15 Allotype

The IgG3 constant region of the 2H15 B cell clone was determined by isolation of RNA using the Trizol method (Kwakkenbos et al., 2010). cDNA was made using random primers. A PCR reaction was performed using CH1 forward (5'-CACCAAGGGCCCATCGGTCTTC-3') (SEQ ID NO: 39) and CH3 reverse primers (5'-TCATTACCCGGA-GACAGG-3') (SEQ ID NO: 40). Primers were constructed based on the human IgG3 sequences found at the IMGT website (www.imgt.org/IMGTrepertoire/Proteins/alleles/index.php?species=Homo %20sapiens&group=IGHC&gene=IGHG3). Sequencing was carried out on the PCR products itself (fw and rev) to determine the allotype according to Vidarsson et al., 2014.

Sequencing of AT14-012 IgG Specific Heavy and Light Chains from the Patient B Cell Repertoire The variable heavy and light chains of AT14-012 were amplified separately from cDNA that was constructed from the isolated RNA pool of the total B cell repertoire of the patient of the time of B cell screening. RNA was isolated by the Trizol method and cDNA was made as previously described (Kwakkenbos et al., 2010). First, to amplify the heavy chain, a pre-amplification step was performed using a mix of two VH3 family specific forward primers VH3-9L (5'-CCATGGAGTTGGGACTGAGC-3') (SEQ ID NO: 41) and VH3LB (5'-CACCATGGARYTKKGRCTBHGC-3') (SEQ ID NO: 42) and IgG specific reverse primers OCG1 (5'-GTCCACCTTGGTGTTGCTGGGCTT-3' (SEQ ID NO: 43), OCG2 (5'-CTGCTGAGGGAGTAGAGTCC-3') (SEQ ID NO: 44) and OCG3 (5'-GGTGTGCACGCCGCTGGTCAG-3') (SEQ ID NO: 45). The PCR product was harvested from the DNA gel by the Qiagen gel extraction kit. A secondary amplification step was performed to amplify AT14-012 specific sequences. Four different PCR reactions were performed using one AT14-012 specific heavy chain forward primer (5'-GTGTCCAGTGTGAAGTGCAGG-3') (SEQ ID NO: 46) and 4 different reverse primers AT14-012Hrev A (5'-GG-GATAATAACCACTCACGGC-3') (SEQ ID NO: 47), AT14-012Hrev B (5'-GTAGGGATAATAACCACTCAC-3') (SEQ ID NO: 48), AT14-012Hrev C (5'-GTCAAAGTAGG-GATAATAAC-3') (SEQ ID NO: 49) and AT14-012Hrev D (5'-CCAGTAGTCAAAGTAGGG-3') (SEQ ID NO: 50) that recognize the rearranged HCDR3 region in a stepwise manner to cover the widest VDJ rearranged sequence. Hereby, framework 4 is not sequenced. The final PCR products from A, B, C and D PCRs were all combined and one single DNA mix was ligated into the pCR2.1 TA cloning vector (Thermo). There was no need to perform the analysis for all reverse reactions separately because of the stepwise annealing on the HCDR3 region. Hereby, we could identify by sequencing which product was amplified by which reverse primer. The inserts were sequenced using the generic M13 reverse and M13 forward primers. To amplify the AT14-012 light chain, a similar protocol was executed. The forward primers to amplify the VK4 family step were VK4L-Fw-leader-ATG: 5'-ACCATGGTGTTGCA-GACCCAG-3' (SEQ ID NO: 51) and VK4L 5'-TYYCT-SYTSCTYTGGATCTCTG-3' (SEQ ID NO: 52) and the reverse primer OCK 5'-ACACTCTCCCCTGTT-GAAGCTCTT-3' (SEQ ID NO: 53). For the second AT14-012 specific amplification step the forward primer was Fw1-1412L 5'-CAGTCTCCAGACTCCCTGT-3' (SEQ ID NO: 54) whereas the three LCDR3 specific reverse primers were AT14-012Lrev A (5'-GGCCGAAGGTG-GAAGGAGTAG-3') (SEQ ID NO: 55) AT14-012Lrev B (5'-GTCCCTTGGCCGAAGGTGGAAG-3') (SEQ ID NO: 56) and AT14-012rev C (5'-TGTCCCTTGGCCGAAGGTGG-3') (SEQ ID NO: 57). Again, the framework 4 of the light chain is not resolved by this PCR method.

Results

AT14-012 recognizes non-mutated CD9. To confirm that the epitope on CD9 recognized by AT14-012 is non-mutated, sequence analysis was performed on a panel of different cell types. Tumor cells including melanoma cells derived from the original patient as well as the AT14-012/2H15 original B cells were subjected to RT-PCR. None of the cells tested showed mutations in the AT14-012 epitope confirming that AT14-012 recognizes a wild type sequence on CD9. Also, these data show that respective CD9 domain on expressed on Bcl6/xL immortalized B cells is the wild type sequence.

The B cell derived 2H15/AT14-012 antibody is of allotype IGHG3* 16. The original patient derived AT14-012/2H15 B cell is of the IgG3 isotype. To determine the allotype of the produced antibody mRNA of the B cells was isolated and subjected to RT-PCR using primers specific to the Fc region. The obtained sequence together with published data (Vidarsson et al., 2014) reveal that the AT14-012 patient derived B cell clone is of allotype IGHG3*16 (FIG. 21). The impact this IgG3 allotype has on the antibody that AT14-012 is and should be is currently unknown. No published work shows the side by side comparison of all allotypes in an effector function assay such as CDC.

The AT14-012 Heavy and Light Chain Sequences are Able to be Retrieved from the Total B Cell Repertoire Our aim here was to investigate whether the AT14-012 sequence was present in the patients' total B cell repertoire. Using a PCR approach applying a pre-amplification step on the variable heavy (VH3) and light chain (VK4) IgG family, we succeeded to acquire proper AT14-012 sequences with the introduced hypermutations during a secondary AT14-012 specific PCR (see materials and methods). The framework region 4 for both chains was not able to be resolved due to the limitations of this approach. There were no obvious additional or less hypermutations found (data not shown) in the heavy chain but at position T109 of the light chain (IMGT numbering), we found that not all sequences had the introduced hypermutation. The original germline sequence contains a serine and this hypermutation is rather conserved in its properties and should not have a major impact on the overall structure or CD9 binding (not tested).

Example 8—Combination with Anti-PD1 Antibodies

Materials & Methods

Generation of human immune system mice (van Lent, Methods Mol Biol, 2010) Sublethally irradiated (350 cGy) neonatal (<1 wk old) NSG mice were injected intrahepatically with human $CD34^+CD38^-$ hematopoietic progenitor cells. Mice that are reconstituted well and produce human immune cells are determined to be suitable for xenograft experiments.

Results

Strong inhibition of in vivo melanoma growth by AT14-012 in combination with anti PD1. Antibodies blocking the PD1-PDL1 axis, in particular those binding PD1, are now widely used to treat a wide variety of late stage cancer patients. Response rates differ per type of cancer, in general only a minor fraction of patients respond well to the treatment. Many clinical trials are being performed to test anti PD1 antibodies in combination with new or registered compounds. We tested the efficacy of AT14-012 in eradication of tumor cells in the presence of Nivolumab (Opdivo, Bristol-Myers Squibb) in a humane immune system (HIS) mouse model. HIS mice are generated by grafting human hematopoietic stem cells in NSG mice (van Lent, Methods Mol Biol, 2010). After an immune system had formed, as characterized by the presence of human immune in the circulation, the mice received a subcutaneous graft of luciferase expressing melanoma cells. Tumors were allowed to grow for 4 weeks to about 100 mm$^3$ in size before the start of treatment. Mice are randomized over 4 different treatment groups receiving intraperitoneal antibodies injections twice per week.

AT10-002 (15 mg/kg)+PBSAT10-002 (15 mg/kg)+Nivolumab (2.5 mg/kg)

AT14-012 (15 mg/kg)+PBSAT14-012 (15 mg/kg)+Nivolumab (2.5 mg/kg)

Figure 22A:
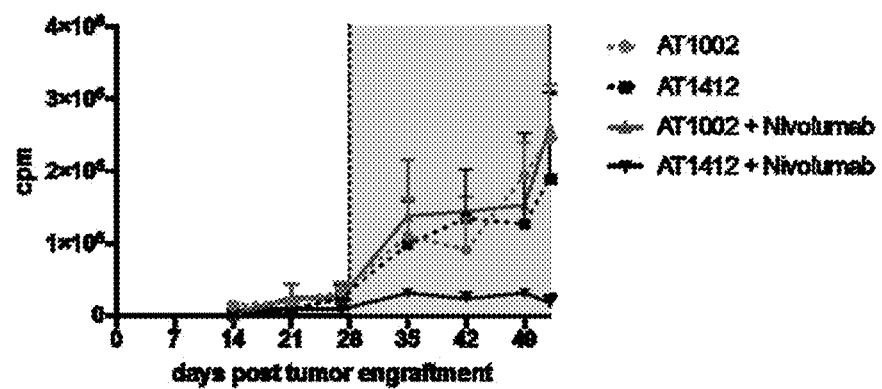
Figure 22B:
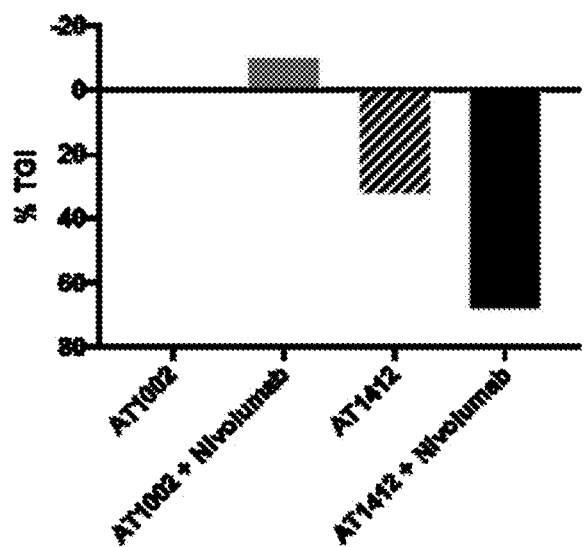

As determined by luciferase imaging mice receiving the AT14-012 antibody alone showed delayed tumor growth as compared to the mice in the AT10-002 (anti Influenza) group (FIG. 22A, B). Interestingly, when the administration of AT14-012 was combined with the anti-PD1 antibody the inhibition of tumor growth was strongly enhanced in comparison the other antibody regimen (FIG. 22A). Calculating the tumor size at the day of sacrifice in relation to the size at the start of the treatment revealed that the combination AT14-012+Nivolumab reduced the size of the tumor with almost 70% (FIG. 22B). These data clearly show that combining the AT14-012 anti-CD9 antibody with a T-cell stimulating antibody holds great potential in eradication of tumor cells.

TABLE 1

Antibody AT14-012

| | |
|---|---|
| Heavy chain CDR1 | DYAMH (SEQ ID NO: 2) |
| Heavy chain CDR2 | GISWNSGSIVYADSVKG (SEQ ID NO: 4) |
| Heavy chain CDR3 | AVSGYYPYFDY (SEQ ID NO: 6) |
| Light chain CDR1 | KSSQSVLYSSNNKNYLG (SEQ ID NO: 8) |
| Light chain CDR2 | WASTRES (SEQ ID NO: 10) |
| Light chain CDR3 | QQYYTTP (SEQ ID NO: 12) |
| Heavy chain | EVQVVESGGGLVQPGRSLRLSCAASGFTFDDYAMHWVRQA PGKGLEWVSGISWNSGSIVYADSVKGRFTISRDNAKNSLY LQLNSLRAEDTAFYYCAKAVSGYYPYFDYWGQGILVTVSS (SEQ ID NO: 14) |
| Light chain | DIVMTQSPDSLSVSLGERATINCKSSQSVLYSSNNKNYLG WYQQKPGQPPKLLIYWASTRESGVPDRFSGSGSGTDFTLT ISSLQAEDVAVYYCQQYYTTPSTFGQGTRLEIK (SEQ ID NO: 16) |
| Heavy chain CDR1 | gat tat gcc atg cac (SEQ ID NO: 1) |
| Heavy chain CDR2 | ggt att agt tgg aat agt ggt agc ata gtc tat gcg gac tct gtg aag ggc (SEQ ID NO: 3) |
| Heavy chain CDR3 | gcc gtg agt ggt tat tat cm tac ttt gac tac (SEQ ID NO: 5) |
| Light chain CDR1 | aag tcc agc cag agt gtt tta tac agc tcc aac aat aag aac tac tta ggt (SEQ ID NO: 7) |
| Light chain CDR2 | tgg gca tct acc cgg gaa tcc (SEQ ID NO: 9) |
| Light chain CDR3 | cag caa tat tat act act cct (SEQ ID NO: 11) |
| Heavy chain | gaa gtg cag gtg gtg gag tct ggg gga ggc ttg gta cag cct ggc agg tcc ctg aga ctc tcc tgt gca gcc tct gga ttc acc ttt gat gat tat gcc atg cac tgg gtc cgg caa gct cca ggg aag ggc ctg gag tgg gtc tca ggt att agt tgg aat agt ggt agc ata gtc tat gcg gac tct gtg aag ggc cga ttc acc atc tcc aga gac aac gcc aag aac tcc ctg tat ctg caa ctg aac agt ctg aga gct gag gac acg gcc ttc tat tac tgt gca aaa gcc gtg agt ggt tat tat ccc tac ttt gac tac tgg ggc cag gga att ttg gtc acc gtc tcc tca (SEQ ID NO: 13) |
| Light chain | gac atc gtg atg acc cag tct cca gac tcc ctg tct gtg tct ctg ggc gag agg gcc acc atc aac tgc aag tcc agc cag agt gtt tta tac agc tcc aac aat aag aac tac tta ggt tgg cag cag aaa cca gga cag cct cct aag ctg ctc att tac tgg gca tct acc cgg gaa tcc ggg gtc cct gac cga ttc agt ggc agc ggg tct ggg aca gat tca act ctc acc atc agc agc |

TABLE 1-continued

Antibody AT14-012 ctg cag gct gaa gat gtg gca gtt tat tac tgt cag caa tat tat act act
cct tcc acc ttc ggc caa ggg aca cga ctg gag att aaa (SEQ ID NO: 15)

REFERENCES de Jong, et al. A Novel Platform for the Potentiation of Therapeutic Antibodies Based on Antigen-Dependent Formation of IgG Hexamers at the Cell Surface. PLoS Biol. 2016 Jan. 6; 14(1)

Gouy et al. SeaView version 4: A multiplatform graphical user interface for sequence alignment and phylogenetic tree building. Mol Biol Evol. 2010 February; 27(2):221-4.

Hanly et al. Review of polyclonal antibody production procedures in mammals and poultry. ILAR Journal (1995); Vol. 37, Number 3: 93-118

Hattori et al. Downregulation of rheumatoid arthritis-related antigen RA-A47 (HSP47/colligin-2) in chondrocytic cell lines induces apoptosis and cell-surface expression of RA-A47 in association with CD9. J. Cell Physiol. (2005); 202(1): 191-204

Huang et al. Correlation of reduction in MRP-1/CD9 and KAI1/CD82 expression with recurrences in breast cancer patients. Am J Pathol. 1998 September; 153(3):973-83.

Iwai et al. Abundant expression of tetraspanin CD9 in activated osteoclasts in ovariectomy-induced osteoporosis and in bone erosions of collagen-induced arthritis. Rheumatol. Int. (2008); 28(3): 225-231

Jin et al. Statins decrease lung inflammation in mice by upregulating tetraspanin CD9 in macrophages. PLoS One (2013); September 9; 8(9): e73706.

Kabat et al. Sequences of Proteins of Immunological interest, 5th Ed. Public Health Service, National Institute of Health, Bethesda, Md. (1991).

Kawakatsu et al. Antithrombotic effect of an anti-glycoprotein IIB/IIIA antibody in primate lethal thrombosis. Thromb Res. 1993 May 1; 70(3):245-54.

Kwakkenbos M J et al. Generation of stable monoclonal antibody-producing B cell receptor-positive human memory B cells by genetic programming. Nat Med. 2010. 16(1):123-8.

Lee, E. C. et al. Complete humanization of the mouse immunoglobulin loci enables efficient therapeutic antibody discovery. Nature Biotechnology (2014); 32(4): 356-363.

Lefranc M P, "Unique database numbering system for immunogenetic analysis" Immunology Today, 18, 509 (1997). PMID: 9386342.

Lefranc M P, "The IMGT unique numbering for immunoglobulins, T cell Receptors and Ig-like domains", The Immunologist. 1999; 7, 132-136.

Lefranc M P, et al. "IMGT unique numbering for immunoglobulin and T cell receptor variable domains and Ig superfamily V-like domains" Dev. Comp. Immunol., 27, 55-77 (2003).

Musunuri et al. Increased Levels of Extracellular Microvesicle Markers and Decreased Levels of Endocytic/Exocytic Proteins in the Alzheimer's Disease Brain. J Alzheimers Dis. 2016 October 18; 54(4):1671-1686.

Rajendra et al. A high cell density transient transfection system for therapeutic protein expression based on a CHO GS-knockout cell line: process development and product quality assessment. Biotechnol Bioeng. 2015 May; 112(5):977-86.

Seigneuret et al. Complete predicted three-dimensional structure of the facilitator transmembrane protein and hepatitis C virus receptor CD81: conserved and variable structural domains in the tetraspanin superfamily. Biophys J. 2006 January 1; 90(1):212-27.

Takeda et al. Preventive role of tetraspanin CD9 in systemic inflammation of COPD. Am. J. Respir. Cell Mol Biol. (2015); 53(6):751-760

Van Lent et al. In vivo modulation of gene expression by lentiviral transduction in "human immune system" Rag2-/- gamma c -/- mice. Methods Mol Biol. 2010; 595:87-115.

Verdegaal et al. Successful treatment of metastatic melanoma by adoptive transfer of blood-derived polyclonal tumor-specific CD4+ and CD8+ T cells in combination with low-dose interferon-alpha. Cancer Immunol Immunother (2011); 60(7): 953-963.

Vidarsson et al. IgG subclasses and allotypes: from structure to effector functions. Front Immunol. 2014 October 20; 5:520.

Wagner et al. Budesonide treatment of patients with collagenous colitis restores normal eosinophil and T-cell activity in the colon. Inflamm Bowel Dis. (2010); 16(7); 1118-1126.

Wagner et al. Bispecific antibody generated with sortase and click chemistry has broad antiinfluenza virus activity. Proc Natl Acad Sci USA. 2014 Nov. 25; 111(47):16820-5.

Yang et al., Protein Structure and Function Prediction Using I-TASSER. Curr Protoc Bioinformatics. 2015 Dec. 17; 52:5.8.1-15.

Zimmerman et al. Crystal Structure of a Full-Length Human Tetraspanin Reveals a Cholesterol-Binding Pocket. Cell. 2016 Nov. 3; 167(4):1041-1051.e 11.

The invention claimed is:

1. A synthetic or recombinant IgG1 antibody or a functional part or functional equivalent thereof that is specific for an epitope of CD9 comprising at least one amino acid selected from the group consisting of K169, D171, V172 and L173 of the CD9 sequence as depicted in SEQ ID NO:19, and that comprises:
   a heavy chain CDR1 sequence that has at least 80% sequence identity with the sequence DYAMH (SEQ ID NO:2); and
   a heavy chain CDR2 sequence GISWNSGSIVY-ADSVKG (SEQ ID NO:4); and
   a heavy chain CDR3 sequence that has at least 80% sequence identity with the sequence AVSGYYPYFDY (SEQ ID NO:6); and
   a light chain CDR1 sequence KSSQSVLYSSNNKNYLG (SEQ ID NO:8); and
   a light chain CDR2 sequence that has at least 85% sequence identity with the sequence WASTRES (SEQ ID NO:10); and
   a light chain CDR3 sequence QQYYTTP (SEQ ID NO:12).

2. The synthetic or recombinant antibody or functional part or functional equivalent according to claim 1, that comprises:
   a heavy chain CDR1 sequence DYAMH (SEQ ID NO:2) or DYAMY (SEQ ID NO:21); and
   a heavy chain CDR2 sequence GISWNSGSIVY-ADSVKG (SEQ ID NO:4); and
   a heavy chain CDR3 sequence AVSGYYPYFDY (SEQ ID NO:6) or AVSGYFPYFDY (SEQ ID NO:22) or AVSGYYPYFHY (SEQ ID NO:23) or AVSGYFPYFHY (SEQ ID NO:24); and
   a light chain CDR1 sequence KSSQSVLYSSNNKNYLG (SEQ ID NO:8); and
   a light chain CDR2 sequence WASTRES (SEQ ID NO:10) or WASIRES (SEQ ID NO:25); and
   a light chain CDR3 sequence QQYYTTP (SEQ ID NO:12).

3. A synthetic or recombinant antibody or functional part or functional equivalent thereof, that comprises:
   a heavy chain CDR1 sequence that has at least 80% sequence identity with the sequence DYAMH (SEQ ID NO:2); and
   a heavy chain CDR2 sequence GISWNSGSIVY-ADSVKG (SEQ ID NO:4); and
   a heavy chain CDR3 sequence that has at least 80% sequence identity with the sequence AVSGYYPYFDY (SEQ ID NO:6); and
   a light chain CDR1 sequence KSSQSVLYSSNNKNYLG (SEQ ID NO:8); and
   a light chain CDR2 sequence that has at least 85% sequence identity with the sequence WASTRES (SEQ ID NO:10); and
   a light chain CDR3 sequence QQYYTTP (SEQ ID NO:12);
   wherein the antibody or functional part or functional equivalent is coupled to another compound.

4. The synthetic or recombinant antibody or functional part or functional equivalent according to claim 3, wherein said other compound is a detectable label, a chemotherapeutic drug, a toxic moiety, an immunomodulatory molecule, another CD9-specific binding compound, or a radioactive compound.

5. A synthetic or recombinant antibody or a functional part or a functional equivalent thereof, that comprises:
   a heavy chain CDR1 sequence that has at least 80% sequence identity with the sequence DYAMH (SEQ ID NO:2); and
   a heavy chain CDR2 sequence GISWNSGSIVYADSVKG (SEQ ID NO:4); and
   a heavy chain CDR3 sequence that has at least 80% sequence identity with the sequence AVSGYYPYFDY (SEQ ID NO:6); and
   a light chain CDR1 sequence KSSQSVLYSSNNKNYLG (SEQ ID NO:8); and
   a light chain CDR2 sequence that has at least 85% sequence identity with the sequence WASTRES (SEQ ID NO:10); and
   a light chain CDR3 sequence QQYYTTP (SEQ ID NO:12);
   wherein the synthetic or recombinant antibody, or functional part or functional equivalent thereof, is a variant of AT14-012.

6. The synthetic or recombinant antibody or functional part or functional equivalent according to claim 5, that comprises:
   a heavy chain CDR1 sequence DYAMH (SEQ ID NO:2) or DYAMY (SEQ ID NO:21); and
   a heavy chain CDR2 sequence GISWNSGSIVYADSVKG (SEQ ID NO:4); and
   a heavy chain CDR3 sequence AVSGYYPYFDY (SEQ ID NO:6) or AVSGYFPYFDY (SEQ ID NO:22) or AVSGYYPYFHY (SEQ ID NO:23) or AVSGYFPYFHY (SEQ ID NO24); and
   a light chain CDR1 sequence KSSQSVLYSSNNKNYLG (SEQ ID NO:8); and
   a light chain CDR2 sequence WASTRES (SEQ ID NO:10) or WASIRES (SEQ ID NO:25); and
   a light chain CDR3 sequence QQYYTTP (SEQ ID NO:12).

7. The synthetic or recombinant antibody or functional part or functional equivalent according to claim 5, comprising a heavy chain variable region sequence having at least 90% sequence identity with the sequence EVQVVESGGGLVQPGRSLRLSCAASGFTFDDYAMHWVRQAPGKGLEWVSGISWNSGSI VYADSVKGRFTISRDNAKNSLYLQLNSLRAEDTAFYYCAKAVSGYYPYFDYWGQGILV TVSS (SEQ ID NO:14).

8. The synthetic or recombinant antibody or functional part or functional equivalent according to claim 5, comprising a light chain variable region sequence having at least 90% sequence identity with the sequence DIVMTQSPDSLSVSLGERATINCKSSQSVLYSSNNKNYLGWYQQKPGQPPKLLIYWAST RESGVPDRFSGSGSGTDFTLTISSLQAEDVAVYYCQQYYTTPSTFGQGTRLEIK (SEQ ID NO:16).

9. The synthetic or recombinant antibody or functional part or function equivalent according to claim 5 comprising:
   a heavy chain variable region sequence EVQVVESGGGLVQPGRSLRLSCAASGFTFDDYAMHWVRQAPGKGLEWVSGISWNSGSI VYADSVKGRFTISRDNAKNSLYLQLNSLRAEDTAFYYCAKAVSGYYPYFDYWGQGILV TVSS (SEQ ID NO:14), or EVQVVESGGGLVQPGRSLRLSCAASGFTFDDYAMYWVRQAPGKGLEWVSGISWNSGSI VYADSVKGRFTISRDNAKNSLYLQLNSLRAEDTAFYYCAKAVSGYFPYFDYWGQGILV TVSS (SEQ ID NO:26) or EVQVVESGGGLVQPGRSLRLSCAASGFTFDDYAMHWVRQAPGKGLEWVSGISWNSGSI VYADSVKGRFTISRDNAKNSLYLQLNSLRAEDTAFYYCAKAVSGYFPYFDYWGQGILV TVSS (SEQ ID NO:27) or EVQVVESGGGLVQPGRSLRLSCAASGFTFDDYAMHWVRQAPGKGLEWVSGISWNSGSI VYADSVKGRFTISRDNAKNSLYLQLNSLRAEDTAFYYCAKAVSGYFPYFHYWGQGILV TVSS (SEQ ID NO:28) or EVQVVESGGGLVQPGRSLRLSCAASGFTFDDYAMYWVRQAPGKGLEWVSGISWNSGSI VYADSVKGRFTISRDNAKNSLYLQLNSLRAEDTAFYYCAKAVSGYFPYFDYWGQGILV TVSS (SEQ ID NO:29) or EVQVVESGGGLVQPGRSLRLSCAASGFTFDDYAMYWVRQAPGKGLEWVSGISWNSGSI VYADSVKGRFTISRDNAKNSLYLQLNSLRAEDTAFYYCAKAVSGYYPYFDYWGQGILV TVSS (SEQ ID NO:30) or EVQVVESGGGLVQPGRSLRLSCAASGFTFDDYAMYWVRQAPGKGLEWVSGISWNSGSI VYADSVKGRFTISRDNAKNSLYLQLNSLRAEDTAFYYCAKAVSGYFPYFHYWGQGILV TVSS (SEQ ID NO:31) and/or
   a light chain variable region sequence DIVMTQSPDSLSVSLGERATINCKSSQSVLYSSNNKNYLGWYQQKPGQPPKLLIYWAST RESGVPDRFSGSGSGTDFTLTISSLQAEDVAVYYCQQYYTTPSTFGQGTRLEIK (SEQ ID NO:16) or DIVMTQSPDSLSVSLGERATINCKSSQSVLYSSNNKNYLGWYQQKPGQPPKLLIYWASIR ESGVPDRFSGSGSGTDFTLTISSLQAEDVAVYYCQQYYTTPSTFGQGTRLEIK (SEQ ID NO:32).

10. The synthetic or recombinant antibody or functional part or functional equivalent according to claim 5, that is a human antibody or functional part or functional equivalent thereof.

11. The synthetic or recombinant antibody or functional part or functional equivalent according to claim 5, that is able to bind melanoma cells, colon carcinoma cells, pancreas carcinoma cells and esophagus carcinoma cells.

12. The synthetic or recombinant antibody or functional part or functional equivalent according to claim 5, wherein said antibody is of the IgG isotype, preferably IgG1 or IgG3.

13. The synthetic or recombinant antibody or functional part or functional equivalent according to claim 12 comprising an arginine at amino acid position 345.

14. A composition comprising the synthetic or recombinant antibody or functional part or functional equivalent according to claim 5.

15. A kit of parts comprising the synthetic or recombinant antibody or functional part or functional equivalent according to claim 5 and a therapeutic agent useful in the treatment of a disorder associated with CD9-expressing cells.

16. The kit of parts according to claim 15, wherein the therapeutic agent is useful in the treatment of a CD9 positive cancer.

17. The synthetic or recombinant antibody or functional part or functional equivalent according to claim 5, wherein the variant is an IgG1 antibody or functional part or functional equivalent thereof.

18. The synthetic or recombinant antibody or functional part or functional equivalent according to claim 6, wherein the variant is an IgG1 antibody or functional part or functional equivalent thereof.

19. A method for determining whether CD9-expressing cells are present in a sample, the method comprising:
contacting said sample with an antibody or functional part or functional equivalent according to claim 5, and
allowing said antibody or functional part or functional equivalent to bind CD9-expressing cells, if present, and
determining whether or not CD9-expressing cells are bound to said antibody or functional part or functional equivalent, thereby determining whether or not CD9-expressing cells are present in said sample.

20. The method according to claim 19, wherein said CD9 expressing cells are CD9 positive tumor cells.

21. A method for producing an antibody or functional part or functional equivalent according to claim 5, the method comprising providing a cell with a nucleic acid molecule encoding the antibody or functional part or functional equivalent according to claim 5, and allowing said cell to translate said nucleic acid molecule, thereby producing said antibody or functional part or functional equivalent according to claim 5, the method optionally further comprising harvesting, purifying and/or isolating said antibody or functional part or functional equivalent according to claim 5.

22. A method for treating a disorder associated with CD9-expressing cells, comprising administering to an individual in need thereof a therapeutically effective amount of an antibody or functional part or functional equivalent according to claim 5.

23. The method according to claim 22 wherein said disorder is selected from the group consisting of CD9 positive cancer, osteoporosis, arthritis, lung inflammation, COPD, colitis, and a disorder associated with innate lymphoid cells.

24. The method according to claim 23, wherein said CD9 positive cancer is selected from the group consisting of melanoma, colorectal cancer, pancreatic cancer, esophageal cancer, lung cancer, breast cancer, ovarian cancer, stomach cancer, squamous cell carcinoma, AML, multiple myeloma, gastric cancer, liver cancer, brain cancer, Kaposi sarcoma, carcinoma mucoepidermoid, choriocarcinoma, fibrosarcoma, cervical carcinoma, glioma, adenocarcinoma, lung adenocarcinoma, non-small-cell lung carcinoma, bladder cancer and small cell lung cancer.

25. The method according to claim 22 whereby said antibody or functional part or functional equivalent is combined with a therapeutic agent useful in the treatment of a disorder associated with CD9-expressing cells.

26. The method according to claim 25, wherein said disorder is a CD9 positive cancer.

27. The method according to claim 25 wherein said therapeutic agent is an agent capable of stimulating C3 convertase formation or capable of counteracting inhibition of C3 convertase formation.

28. The method according to claim 27 wherein said agent is a CD55 blocking antibody.

29. The method according to claim 25 wherein said therapeutic agent is a blocking antibody specific for a co-inhibitory T cell molecule.

30. The method according to claim 29 wherein said antibody is selected from the group consisting of an anti-CTLA4 antibody, an anti-PD-1 antibody, an anti-PD-L1 antibody, an anti-PD-L2 antibody, an anti-SIRPα antibody, an anti-TB/13 antibody, an anti-LAG3 antibody, an anti-CD276 antibody, an anti-CD272 antibody, an anti-KIR antibody, an anti-A2AR antibody, an anti-VISTA antibody and an anti-IDO antibody.

31. An ex vivo method for determining whether an individual is suffering from a CD9-positive cancer, the method comprising:
contacting tumor cells from said individual with an antibody or functional part or functional equivalent according to claim 5,
allowing said antibody or functional part or functional equivalent to bind CD9-expressing cells, if present, and
determining whether or not CD9-expressing cells are bound to said antibody or functional part or functional equivalent, thereby determining whether or nor said individual is suffering from a CD9-positive cancer.

* * * * *

UNITED STATES PATENT AND TRADEMARK OFFICE
CERTIFICATE OF CORRECTION

PATENT NO. : 11,136,407 B2
APPLICATION NO. : 16/068742
DATED : October 5, 2021
INVENTOR(S) : Hergen Spits et al.

It is certified that error appears in the above-identified patent and that said Letters Patent is hereby corrected as shown below:

On the Title Page

Item (73) Assignee:
Please delete "AIMM Therapeutics B.V., Amsterdam Zuidoost (NL)"
And insert:
--Kling Biotherapeutics B.V., Amsterdam (NL)--

Signed and Sealed this
Twenty-fourth Day of May, 2022

Katherine Kelly Vidal
*Director of the United States Patent and Trademark Office*